(12) United States Patent
Griswold-Prenner et al.

(10) Patent No.: US 8,980,270 B2
(45) Date of Patent: *Mar. 17, 2015

(54) METHODS OF TREATING A TAUOPATHY

(71) Applicant: iPierian, Inc., South San Francisco, CA (US)

(72) Inventors: Irene Griswold-Prenner, South San Francisco, CA (US); Nancy E. Stagliano, South San Francisco, CA (US); Vu Dang, South San Francisco, CA (US)

(73) Assignee: iPierian, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/154,954

(22) Filed: Jan. 14, 2014

(65) Prior Publication Data

US 2014/0234214 A1 Aug. 21, 2014

Related U.S. Application Data

(60) Provisional application No. 61/754,085, filed on Jan. 18, 2013, provisional application No. 61/781,823, filed on Mar. 14, 2013.

(51) Int. Cl.
*A61K 39/00* (2006.01)
*A61K 39/395* (2006.01)
*C07K 16/18* (2006.01)
*G01N 33/68* (2006.01)

(52) U.S. Cl.
CPC ............ *C07K 16/18* (2013.01); *G01N 33/6896* (2013.01); *G01N 2333/4709* (2013.01); *A61K 2039/505* (2013.01); *C07K 2317/92* (2013.01); *Y10S 424/80* (2013.01)
USPC ................... 424/139.1; 514/17.7; 424/133.1; 424/172.1; 424/800; 424/135.1

(58) Field of Classification Search
None
See application file for complete search history.

(56) References Cited

U.S. PATENT DOCUMENTS

| | | |
|---|---|---|
| 5,492,812 A | 2/1996 | Vooheis |
| 5,535,663 A | 7/1996 | Yamashita et al. |
| 5,600,392 A | 2/1997 | Sakamoto et al. |
| 5,666,808 A | 9/1997 | Yamashita et al. |
| 5,733,734 A | 3/1998 | Trojanowski et al. |
| 5,811,310 A | 9/1998 | Ghanbari et al. |
| 5,843,779 A | 12/1998 | Vandermeeren et al. |
| 5,861,257 A | 1/1999 | Vandermeeren et al. |
| 6,008,024 A | 12/1999 | Vandermeeren et al. |
| 6,010,913 A | 1/2000 | Vandermeeren et al. |
| 6,121,003 A | 9/2000 | Vanmechelen et al. |
| 6,232,437 B1 | 5/2001 | Vandermeeren et al. |
| 6,238,892 B1 | 5/2001 | Mercken et al. |
| 6,500,674 B1 | 12/2002 | Vandermeeren et al. |
| 6,680,173 B2 | 1/2004 | Vanmechelen et al. |
| 6,900,293 B2 | 5/2005 | Mercken et al. |
| 7,387,879 B2 | 6/2008 | Vanmechelen et al. |
| 7,427,392 B1 | 9/2008 | Seubert et al. |
| 7,446,180 B2 | 11/2008 | Novak |
| 7,466,180 B2 | 12/2008 | Slawecki |
| 8,012,936 B2 | 9/2011 | Sigurdsson et al. |
| 8,163,873 B2 | 4/2012 | Mercken et al. |
| 8,409,584 B2 | 4/2013 | Wisniewski et al. |
| 2001/0018191 A1 | 8/2001 | Mercken et al. |
| 2002/0001857 A1 | 1/2002 | Vandermeeren et al. |
| 2002/0019016 A1 | 2/2002 | Vanmechelen et al. |
| 2003/0138972 A1 | 7/2003 | Vandermeeren et al. |
| 2003/0143760 A1 | 7/2003 | Vandermeeren et al. |
| 2003/0147811 A1 | 8/2003 | Wisniewski et al. |
| 2003/0194742 A1 | 10/2003 | Vanmechelen et al. |
| 2004/0014142 A1 | 1/2004 | Vanmechelen et al. |
| 2004/0038430 A1 | 2/2004 | Vandermeeren et al. |
| 2004/0072261 A1 | 4/2004 | Kostanjevecki et al. |
| 2004/0091942 A1 | 5/2004 | Vanmechelen et al. |
| 2004/0110250 A1 | 6/2004 | Wischik et al. |
| 2004/0265919 A1 | 12/2004 | Vanderstichele et al. |
| 2005/0014821 A1 | 1/2005 | Tsai et al. |
| 2005/0181460 A1 | 8/2005 | Ohno et al. |
| 2005/0191685 A1 | 9/2005 | Vanmechelen et al. |
| 2005/0196844 A1 | 9/2005 | Lee et al. |
| 2005/0221391 A1 | 10/2005 | Davies |
| 2005/0255113 A1 | 11/2005 | Huston et al. |
| 2005/0260697 A1 | 11/2005 | Wang et al. |

(Continued)

FOREIGN PATENT DOCUMENTS

| | | |
|---|---|---|
| WO | 96/20218 A1 | 7/1996 |
| WO | WO 98/22120 | 5/1998 |
| WO | WO 02/45743 | 6/2002 |
| WO | WO 03/014960 | 2/2003 |
| WO | WO 2004/007547 | 1/2004 |
| WO | WO 2005/010044 | 2/2005 |
| WO | WO 2005/120166 | 12/2005 |
| WO | WO 2011/013034 | 3/2011 |
| WO | WO 2011/026031 | 3/2011 |
| WO | WO 2011/056300 | 5/2011 |

(Continued)

OTHER PUBLICATIONS

Bartos et al. 2012 "Patients with Alzheimer disease have elevated intrathecal synthesis of antibodies against tau protein and heavy neurofilament" J Neuroimmunology 252:100-105.*

(Continued)

*Primary Examiner* — Gregory S Emch
*Assistant Examiner* — Adam M Weidner
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure provides methods of treating a tauopathy, involving administering an anti-Tau antibody. The present disclosure also provides anti-Tau antibodies, and formulations comprising same, for use in the methods.

50 Claims, 33 Drawing Sheets

(56) References Cited

U.S. PATENT DOCUMENTS

| | | |
|---|---|---|
| 2005/0261475 A1 | 11/2005 | Tseng et al. |
| 2006/0008853 A1 | 1/2006 | Mercken et al. |
| 2006/0122122 A1 | 6/2006 | Kobayashi et al. |
| 2006/0167227 A1 | 7/2006 | Kontsekova |
| 2007/0218491 A1 | 9/2007 | Vasan et al. |
| 2008/0050383 A1* | 2/2008 | Sigurdsson et al. ....... 424/141.1 |
| 2008/0057593 A1 | 3/2008 | Vanderstichele et al. |
| 2008/0213834 A1 | 9/2008 | Reed et al. |
| 2008/0220449 A1 | 9/2008 | Vasan et al. |
| 2008/0261889 A1 | 10/2008 | Vanmechelen et al. |
| 2009/0137051 A1 | 5/2009 | Mercken et al. |
| 2009/0317805 A1 | 12/2009 | Wang et al. |
| 2010/0055722 A1 | 3/2010 | Nayak et al. |
| 2010/0063250 A1 | 3/2010 | Kontsekova |
| 2010/0284909 A1 | 11/2010 | Wisniewski et al. |
| 2010/0297108 A1 | 11/2010 | Henco et al. |
| 2010/0316564 A1 | 12/2010 | Sigurdsson |
| 2010/0323343 A1 | 12/2010 | Egan et al. |
| 2011/0027817 A1 | 2/2011 | Arancio et al. |
| 2011/0143380 A1 | 6/2011 | Holtzman et al. |
| 2011/0143443 A9 | 6/2011 | Mercken et al. |
| 2011/0177109 A1 | 7/2011 | Smith et al. |
| 2011/0201098 A1 | 8/2011 | Laureyn et al. |
| 2011/0250237 A1 | 10/2011 | O'Hagan et al. |
| 2011/0312059 A1 | 12/2011 | Moe et al. |
| 2011/0318358 A1 | 12/2011 | Sigurdsson et al. |
| 2012/0029169 A1 | 2/2012 | Moe et al. |
| 2012/0087861 A1 | 4/2012 | Nitsch et al. |
| 2012/0142602 A1 | 6/2012 | Brady et al. |
| 2012/0183599 A1* | 7/2012 | Pfeifer et al. ................. 424/450 |
| 2012/0244146 A1 | 9/2012 | Chain |
| 2012/0244174 A1 | 9/2012 | Chain |
| 2012/0276009 A1 | 11/2012 | Pfeifer et al. |
| 2013/0028914 A1 | 1/2013 | Kayed |
| 2013/0156783 A1 | 6/2013 | Wisniewski et al. |
| 2013/0266514 A1 | 10/2013 | Nitsch et al. |
| 2013/0266585 A1 | 10/2013 | Nitsch et al. |
| 2013/0266586 A1 | 10/2013 | Nitsch et al. |
| 2013/0287838 A1 | 10/2013 | Hickman et al. |
| 2013/0288280 A1 | 10/2013 | Ladenson et al. |
| 2013/0295021 A1 | 11/2013 | Chen et al. |
| 2013/0310541 A1 | 11/2013 | Bohrmann et al. |
| 2014/0056901 A1 | 2/2014 | Agadjanyan et al. |
| 2014/0086921 A1 | 3/2014 | Griswold-Prenner et al. |
| 2014/0099303 A1 | 4/2014 | Griswold-Prenner et al. |
| 2014/0099304 A1 | 4/2014 | Griswold-Prenner et al. |

FOREIGN PATENT DOCUMENTS

| | | |
|---|---|---|
| WO | WO 2012/045882 | 4/2012 |
| WO | WO 2012/049570 | 4/2012 |
| WO | WO 2012/054008 | 4/2012 |
| WO | WO 2012/106363 | 8/2012 |
| WO | WO 2013/007839 | 1/2013 |
| WO | WO 2013/041962 | 3/2013 |
| WO | WO 2013/044147 | 3/2013 |
| WO | WO 2013/050567 | 4/2013 |
| WO | WO 2013/063086 | 5/2013 |
| WO | WO 2013/096380 | 6/2013 |
| WO | WO 2013/151762 | 10/2013 |
| WO | WO 2014/008404 | 1/2014 |
| WO | 2014/028777 A2 | 2/2014 |
| WO | WO 2014/031694 | 2/2014 |

OTHER PUBLICATIONS

Ksiezak-Reding, et al., "Repid Communication, Mapping of the Alz 50 Epitope in Microtubule-Associated Proteins Tau", Journal of Neuroscience Research, 1990, vol. 25, pp. 412-419.

Johnson, et al. "The τ Protein in Human Cerebrospinal Fluid in Alzheimer's Disease Consists of Proteolytically Derived Fragments", Journal of Neurochemistry, 1997, 68(1): pp. 430-433.

Meredith, et al. "Characterization of Novel CSF Tau and ptau Biomarkers for Alzheimer's Disease", PLoS One, 2013, vol. 8, Issue 10, pp. 1-14.

Ghoshal, et al., "Tau Conformational Changes Correspond to Impairments of Episodic Memory in Mild Cognitive Impairment and Alzheimer's Disease", Experiments Neurology, 2002, No. 177, pp. 475-493.

Horowitz, et al., "Early N-Terminal Changes and Caspase-6 Cleavage of Tau in Alzheimer's Disease", Journal of Neuroscience, 2004, 24(36), pp. 7895-7902.

Yanamandra, et al., "Anti-Tau Antibodies that Block Tau Aggregate Seeding in Vitro Markedly Decrease Pathology and Improve Cognition in Vivo", (2013) Neuron, vol. 80, pp. 402-414.

Kanaan, et al. "Pathogenic Forms of Tau Inhibit Kinesin-Dependent Axonal Transport through a Mechanism Involving Activation of Axonal Phosphotransferases", The Journal of Neuroscience, 2011, 31(27): pp. 9858-9868.

Jicha et al. "Sequence requirements for formation of conformational variants of tau similar to those found in Alzheimer's disease" (1999) J. Neurosci. Res. vol. 55, pp. 713-723.

Yamamori et al. "Tau in cerebrospinal fluid: a sensitive sandwich enzyme-linked immunosorbent assay using tyramide signal amplification" (2007) Neurosci. Lett. 418:186.

Chai, et al. "Passive Immunization with Anti-Tau Antibodies in Two Transgenic Models", The Journal of Biological Chemistry, 2011, vol. 286, No. 39: pp. 34457-34467.

Boutajangout, et al. "Passive Immunization Targeting Pathological Phosphor-tau Protein in a Mouse Model Reduces Functional Decline and Clears tau Aggregates from the Brain", Journal of Neurochemistry, 2011, 118(4): pp. 658-667.

Sigurdsson, "Immunotherapy Targeting Pathological Tau Protein in Alzheimer's Disease and Related Tauopathies", J. Alzheimer's Dis. Oct. 2008, 15(2):157-168.

NCBI, GenBank Accession No. CAI54295.1, Apr. 15, 2005.

NCBI, GenBank Accession No. NP_058525.1, Jun. 27, 2012.

Arnesen, "Towards a Functional Understanding of Protein N-Terminal Acetylation", PLoS Bio., 2011, vol. 9, Issue 5, pp. 1-5.

Asuni, et al. "Immunotherapy Targeting Pathological Tau Conformers in a Tangle Mouse Model Reduces Brain Pathology with Associated Functional Improvements", Journal of Neuroscience, 2007, 27(34): pp. 9115-9129.

Bi, et al. "Tau-Targeted Immunization Impedes Progression of Neurofibrillary Histopathology in Aged P301L Tau Transgenic Mice", PLoS One, 2011, vol. 6, Issue 12, pp. 1-7.

Binder, et al. "Tau, Tangles, and Alzheimer's Disease", Biochimica et Biophysica Acta 1739, 2005, pp. 216-223.

Borroni, et al. "Pattern of Tau Forms in CSF is Altered in Progressive Supranuclear Palsy", Neurobiology of Aging, 2009, 30(1): pp. 34-40.

Braak, et al. "Staging of Alzheimer's Disease-Related Neurofibrillary Changes", Neurobiology of Aging, 1995, vol. 16, No. 3: pp. 271-284.

Brunden, et al., "Advances in Tau-focused Drug Discovery for Alzheimer's Disease and Related Tauopathies", Nat. Rev. Drug. Discov., 2009, 8(1), pp. 783-793.

Carmel, et al. "The Structural Basis of Monoclonal Antibody Alz50's Selectivity for Alzheimer's Disease Pathology", The Journal of Biological Chemistry, 1996, vol. 271, No. 51: pp. 32789-32795.

Chow, et al. "Aminopeptidases Do Not Directly Degrade Tau Protein", Molecular Neurodegeneration, 2010, 5:48, pp. 1-10.

De Strooper, "Proteases and Proteolysis in Alzheimer Disease: A Multifactorial View on the Disease Process", Physiol Rev. ,2010, 90(2): pp. 465-494.

Demeule, et al., "Identification and Design of Peptides as a New Drug Delivery System for the Brain", The Journal of Pharmacology and Experimental Therapeutics, 2008, vol. 324, No. 3: pp. 1064-1072.

Fagan, et al. "Cerebrospinal Fluid Biomarkers of Alzheimer's Disease", Biomark Med. , 2010, 4(1): pp. 51-63.

Ghoshal, et al., "Tau-66: Evidence for a Novel Tau Conformation in Alzheimer's Disease", Journal of Neurochemistry, 2001, 77, pp. 1372-1385.

Guillozet-Bongaarts, et al., "Tau Truncation During Neurofibrillary Tangle Evolution in Alzheimer's Disease", Neurobiology of Aging, 2005, 26, pp. 1015-1022.

(56) References Cited

OTHER PUBLICATIONS

Gu, et al., "Two Novel Tau Antibodies Targeting the 396/404 Region Are Primarily Taken Up by Neurons and Reduce Tau Protein Pathology", Journal of Biological Chemistry, 2013, vol. 288, No. 46, pp. 33081-33095.

Hu, et al. "Biomarker Discovery for Alzheimer's Disease, Frontotemporal Lobar Degeneration, and Parkinson's Disease", Acta Neuropathol., 2010, 120(3): pp. 385-399.

Ishiguro, et al. "Phosphorylated Tau in Human Cerebrospinal Fluid is a Diagnostic Marker for Alzheimer's Disease", Neuroscience Letters, 1999, 270(2): pp. 91-94.

Israel et al., "Probing Sporadic and Familial Alzheimer's Disease Using Induced Pluripotent Stem Cells", Nature, 2012, 482(7384): pp. 216-220.

Kanaan, et al., "Phosphorylation in the Amino Terminus of Tau Prevents Inhibition of Anterograde Axonal Transport", Neurobiology of Aging, 2012, 33(4):826, pp. 15-30.

Kim, et al. "Secretion of Human Tau Fragments Resembling CSF-tau in Alzheimer's Disease is Modulated by the Presence of the Exon 2 Insert", FEBS Letters, 2010, 584(14): pp. 3085-3088.

Kfoury, et al., "Trans-cellular Propagation of Tau Aggregation by Fibrillar Species", The Journal of Biological Chemistry, vol. 287, No. 23, 2012 pp. 19440-19451.

Lewis, et al., "Neurofibrillary Tangles, Amyotrophy and Progressive Motor Disturbance in Mice Expressing Mutant (P301L) Tau Protein", Nature Genetics, 2000, vol. 25, pp. 402-405.

Lin, et al. "Filamentous Tau in Oligodendrocytes and Astrocytes of Transgenic Mice Expressing the Human Tau Isoform with the P301L Mutation", American Journal of Pathology, 2003, 162(1): pp. 213-218.

Liu, et al. "Trans-Synaptic Spread of Tau Pathology in Vivo", PLoS ONE, 2012, 7(2):e31302, pp. 1-9.

Min, et al. "Acetylation of Tau Inhibits Its Degradation and Contributes to Tauopathy", Neuron, 2010, 67(6): pp. 953-966.

Plouffe, et al. "Hyperphosphorylation and Cleavage at D421 Enhance Tau Secretion", PLoS One, 2012, 7(5):e36873, pp. 1-13.

Saman, et al. "Exosome-associated Tau Is Secreted in Tauopathy Models and Is Selectively Phosphorylated in Cerebrospinal Fluid in Early Alzheimer Disease", The Journal of Biological Chemistry, 2012, 287(6): pp. 3842-3849.

Sigurdsson, "Tau-Focused Immunotherapy for Alzheimer's Disease and Related Tauopathies", Curr Alzheimer Res. (Oct. 2009), 6(5):446-450.

Troquier, et al. "Targeting Phospho-Ser422 by Active Tau Immunotherapy in the THY-Tau22 Mouse Model: A Suitable Therapeutic Approach", Current Alzheimer Research, 2012, 9(4): pp. 387-405.

Waxman et al. "Induction of Intracellular Tau Aggregation is Promoted by α-Synuclein Seeds and Provides Novel Insights into the Hyperphosphorylation of Tau", J. Neurosci. (May 2011), 31(21):7604-7618.

Vigo-Pelfrey, et al., "Elevation of Microtubule-Associated Protein Tau in the Cerebrospinal Fluid of Patients with Alzheimer's Disease", Neurology, 1995, vol. 45, pp. 788-793.

Whiteman, et al. "Rapid Changes in Phospho-MAP/Tau Epitopes during Neuronal Stress: Cofilin-Actin Rods Primarily Recruit Microtubule Binding Domain Epitopes", PLoS One, 2011, 6(6):e20878, pages.

Rafii et al., "Recent developments in Alzheimer's disease therapeutics", BMC Medicine, 2009, 7:7.

De Meyer et al., "Diagnosis-Independent Alzheimer Disease Biomarker Signature in Cognitively Normal Elderly People", Arch. Neurol., 2010, vol. 67, No. 8. pp. 949-956.

Griswold-Prenner, I. et al., "Effects of a Tau therapeutic antibody of the ISF/CSF levels of secreted Tau in the P301L mouse model," Neuroscience, Nanosymposium, Poster No. 598.07, 2 pages (2013).

Higuchi, Makoto et al., "Tau Protein and Tauopathy," Neuropsychopharmacology—5th Generation of Progress, Williams, & Wilkins, Philadelphia, Chapter 94, pp. 1339-1354 (2002).

Terwel, Dick et al., "Changed Conformation of Mutant Tau-P301L Underlies the Moribund Tauopathy, Absent in Progressive, Nonlethal Axonopathy of Tau-4R/2N Transgenic Mice," The Journal of Biological Chemistry, vol. 280 (5):3963-3973 (2005).

Ward, Sarah M. et al., "Tau oligomers and tau toxicity in neurodegenerative disease," Biochem. Soc. Trans, vol. 40:667-671 (2012).

Yoshiyama, Yasumasa et al., "Therapeutic strategies for tau mediated neurodegeneration," J. Neurol. Neurosurg. Psychiatry, vol. 84:784-795 (2013).

International Search Report and Written Opinion for Application No. PCT/US2014/041553, 14 pages, dated Sep. 2, 2014.

Second Written Opinion for Application No. PCT/US2013/055203, 9 pages, dated Jul. 28, 2014.

Garcia-Sierra, Francisco et al., "Conformational changes and truncation of tau protein during tangle evolution in Alzheimer's disease," Journal of Alzheimer's Disease, vol. 5:65-77 (2003).

Ghoshal, Nupur et al., "Tau Conformational Changes Correspond to Impairments of Episodic Memory in Mild Cognitive Impairment and Alzheimer's Disease," Experimental Neurology, vol. 177:475-493 (2002).

Horowitz, Peleg M. et al., "Early N-Terminal Changes and Caspase-6 Cleavage of Tau in Alzheimer's Disease," The Journal of Neuroscience, vol. 24(36):7895-7902 (2004).

Meredith, Jere et al., "Novel Tau Fragments are Present in Human CSF," Alzheimer's Association International Conference, p. P276, Poster Presentation No. P2-039, 2 pages (2012).

* cited by examiner

Figure 1A

Hybridoma IPN001 Heavy Chain Sequences

```
  1       E   V   Q   L   V   E   S   G   E   D   L   V   K   P   G   G   S   L   K   L
  2     GAGGTGCAGT TGGTGGAGTC TGGGGAAGAC TTAGTGAAGC CTGGAGGGTC CCTGAAACTC

S   C   V   A   S   G   F   A   F   S   S   Y   G   M   S   W   V   R   Q   T
 61     TCCTGTGTCG CTTCTGGATT CGCTTTCAGT AGCTATGGCA TGTCTTGGGT TGGCCAGACT

P   D   M   R   L   E   W   V   A   T   I   S   S   S   G   S   R   T   Y   F
121     CCAGACATGA GGCTGGAGTG GGTCGCAACA ATTAGTAGCA GTGGTAGTCG CACCTACTTT

P   D   S   V   K   G   R   L   T   I   S   R   D   N   D   K   N   I   L   Y
181     CCAGACAGTG TGAAGGGGCG ACTCACCATC TCCAGAGACA ATGACAAGAA CATCCTATAC

L   Q   M   S   S   L   R   S   E   D   T   A   M   Y   Y   C   T   I   T   W
241     CTACAAATGA GCAGTCTGAG GTCTGAGGAC ACAGCCATGT ACTATTGTAC GATTACCTGG

D   G   A   M   D   Y   W   G   R   G   I   S   V   T   V   S   S     (SEQ ID NO:14)
301     GACGGTGCTA TGGACTACTG GGGTCGGTGGA ATATCAGTCA CCGTCTCCTC A (SEQ ID NO:18)
```

CDR definitions and protein sequence numbering according to Kabat numbering system. CDRs, and nucleotide sequences encoding the CDRs, are in bold text and underlined.

Figure 1B

Hybridoma IPN001 Light Chain Sequences

```
          D   V   L   M   T   Q   T   P   L   S   L   A   V   N   L   G   D   Q   A   S
  1      GATGTTTTGA TGACCCAAAC TCCGCTCTCC CTGGCAGTCA ATCTTGGAGA TCAAGCCTCC

L   S   C   R   S   S   Q   T   I   L   H   S   N   G   N   T   Y   L   E   W
 61      CTCTCTTGCA GATCGAGTCA GACTATTTTA CATAGTAATG GAAATACCTA TTTAGAATGG

Y   L   Q   K   P   G   Q   S   P   R   L   L   I   Y   K   V   S   K   R   F
121      TATTTGCAGA AACCAGGCCA GTCTCCAAGA CTCCTGATCT ACAAAGTTTC TAAACGATTT

S   G   V   P   D   R   F   S   G   S   G   S   G   T   D   F   T   L   K   I
181      TCTGGGGTCC CAGACAGGTT CAGTGGCAGT GGATCAGGGA CAGATTTCAC ACTCAAGATC

S   R   V   E   A   D   D   L   G   I   Y   Y   C   F   Q   G   S   L   V   P
241      AGCAGAGTGG AGGCTGACGA TCTGGGAATT TATTACTGCT TTCAAGGTTC ACTTGTTCCT

W   A   F   G   G   G   T   K   L   E   I   K        (SEQ ID NO:13)
301      TGGGCGTTCG GTGGAGGCAC CAAGCTGGAA ATCAAA        (SEQ ID NO:17)
```

CDR definitions and protein sequence numbering according to Kabat numbering system. CDRs, and nucleotide sequences encoding the CDRs, are in bold text and underlined.

Figure 2A

Hybridoma IPN002 Heavy Chain Sequences

```
  1   E   V   H   L   V   E   S   G   G   A   L   V   K   P   G   G   S   L   K   L
      GAGGTTCATC TGGTTGGAGTC TGGGGGAGCC TTAAGTGAAGC CTGGAGGGTC CCTGAAACTC

61   S   C   A   A   S   G   F   S   F   S   Q   F   S   K   Y   G   M   S   W   V   R   Q   T
      TCCTGTGCAG CCTCTGGATT CAGTTTCAGT CAGTTTCAGT AAATATGGCA TGTCTTGGGT TGGCCAGACT

121   P   D   K   R   L   E   W   V   A   T   I   S   S   G   S   R   T   Y   Y
      CCAGACAAGA GGCTGGAGTG GGTCGCAACC ATTAGTAGTA GTGGGAGTCG CACCTACTAT

181   P   D   S   V   K   G   Q   F   T   I   S   R   D   N   A   K   N   T   L   Y
      CCAGACAGTG TGAAGGGCCA ATTCACCATC TCCAGAGACA ATGCCAAGAA CACCCTGTAC

241   L   Q   M   S   S   L   K   S   E   D   T   A   M   Y   Y   C   S   I   S   W
      CTGCAAATGA GCAGTCTGAA GTCTGAGGAC ACAGCCATGT ATTACTGTTC AATTAGCTGG

301   D   G   A   M   D   Y   W   G   Q   G   T   S   V   T   V   S   S      (SEQ ID NO:16)
      GACGGTGCTA TGGACTACTG GGGTCAAGGG ACCTCAGTCA CCGTCTCCTC A             (SEQ ID NO:20)
```

CDR definitions and protein sequence numbering according to Kabat numbering system. CDRs, and nucleotide sequences encoding the CDRs, are in bold text and underlined.

Figure 2B

Hybridoma IPN002 Light Chain Sequences

```
  1       D  V  L  M  T  Q  T  P  L  S  L  P  V  S  L  G  D  Q  A  S
          GATGTTTTGA TGACCCAAAC TCCACTCTCC CTGCCTGTCA GTCTTGGAGA TCAAGCCTCC

61       I  S  C  K  S  S  Q  S  I  V  H  S  N  G  N  T  Y  L  E  W
          ATCTCTTGCA AATCTAGTCA GAGCATTGTA CATAGTAATG GAAACACCTA TTTAGAATGG

121       Y  L  Q  K  P  G  Q  S  P  K  L  L  V  Y  K  V  S  N  R  F
          TACCTGCAGA AACCAGGCCA GTCTCCAAAG CTCCTGGTCT ACAAAGTTTC CAATCGATTT

181       S  G  V  P  D  R  F  S  G  S  G  S  G  T  D  F  T  L  K  I
          TCTGGGGTCC CAGACAGGTT CAGTGGCAGT GGATCAGGGA CAGATTTCAC ACTCAAGATC

241       S  R  V  E  A  E  D  L  G  T  Y  Y  C  F  Q  G  S  L  V  P
          AGCAGAGTGG AGGCTGAGGA TCTGGGAACT TATTACTGCT TTCAAGGTTC ACTTGTTCCT

301       W  A  F  G  G  G  T  K  L  E  I  K   (SEQ ID NO:15)
          TGGGCGTTCG GTGGAGGCAC CAAGCTGGAA ATCAAAA    (SEQ ID NO:19)
```

CDR definitions and protein sequence numbering according to Kabat numbering system. CDRs, and nucleotide sequences encoding the CDRs, are in bold text and underlined.

Quantification of CSF and CM samples pre and post Tau affinity isolation

Figure 6A
Human tau isoforms

```
isoform 2     MAEPRQEFEVMEDHAGTYGLGDRKDQGGYTMHQDQEGDTDAGLKESPLQTPTEDGSEEPG  60
isoform 3     MAEPRQEFEVMEDHAGTYGLGDRKDQGGYTMHQDQEGDTDAGLK----------------  44
isoform 4     MAEPRQEFEVMEDHAGTYGLGDRKDQGGYTMHQDQEGDTDAGLK----------------  44
isoform 5     MAEPRQEFEVMEDHAGTYGLGDRKDQGGYTMHQDQEGDTDAGLKESPLQTPTEDGSEEPG  60
isoform 6     MAEPRQEFEVMEDHAGTYGLGDRKDQGGYTMHQDQEGDTDAGLKESPLQTPTEDGSEEPG  60
isoform 1     MAEPRQEFEVMEDHAGTYGLGDRKDQGGYTMHQDQEGDTDAGLKESPLQTPTEDGSEEPG  60
fetal         MAEPRQEFEVMEDHAGTYGLGDRKDQGGYTMHQDQEGDTDAGLK----------------
              ******************************************* isoform 2     SETSDAKSTPTAEDVTAPLVDEGAPGKQAAAQPHTEIPEGTTAEEAGIGDTPSLEDEAAG  120
isoform 3     ------------------------------------------AEEAGIGDTPSLEDEAAG   62
isoform 4     ------------------------------------------AEEAGIGDTPSLEDEAAG   62
isoform 5     SETSDAKSTP--------------------------TAEAEEAGIGDTPSLEDEAAG   91
isoform 6     SETSDAKSTPTAEDVTAPLVDEGAPGKQAAAQPHTEIPEGTTAEEAGIGDTPSLEDEAAG  120
isoform 1     SETSDAKSTPTAEDVTAPLVDEGAPGKQAAAQPHTEIPEGTTAEEAGIGDTPSLEDEAAG  120
fetal         ------------------------------------------AEEAGIGDTPSLEDEAAG
                                                        ****************** isoform 2     HVTQ--------------------------------------------------------  124
isoform 3     HVTQ--------------------------------------------------------   66
isoform 4     HVTQ--------------------------------------------------------   66
isoform 5     HVTQ--------------------------------------------------------   95
isoform 6     HVTQEPESGKVVQEGFLREPGPPGLSHQLMSGMPGAPLLPEGPREATRQPSGTGPEDTEG  180
isoform 1     HVTQEPESGKVVQEGFLREPGPPGLSHQLMSGMPGAPLLPEGPREATRQPSGTGPEDTEG  180
fetal         HVTQ
              ****
```

Figure 6B

```
isoform 2    ------------------------------------------------------------
isoform 3    ------------------------------------------------------------
isoform 4    ------------------------------------------------------------
isoform 5    GRHAPELLKHQLLGDLHQEGPPLKGAGGKERPGSKEEVDEDRDVDESSPQDSPPSKASPA  240
isoform 6    GRHAPELLKHQLLGDLHQEGPPLKGAGGKERPGSKEEVDEDRDVDESSPQDSPPSKASPA  240
isoform 1    ------------------------------------------------------------
fetal        ------------------------------------------------------------ isoform 2    ------------------------------------------------------------
isoform 3    ------------------------------------------------------------
isoform 4    ------------------------------------------------------------
isoform 5    QDGRPPQTAAREATSIPGFPAEGAIPLPVDFLSKVSTEIPASEPDGPSVGRAKGQDAPLE  300
isoform 6    QDGRPPQTAAREATSIPGFPAEGAIPLPVDFLSKVSTEIPASEPDGPSVGRAKGQDAPLE  300
isoform 1    ------------------------------------------------------------
fetal        ------------------------------------------------------------ isoform 2    ------------------------------------------------------------
isoform 3    ------------------------------------------------------------
isoform 4    ------------------------------------------------------------
isoform 5    PTFHVEITPNVQKEQAHSEEHLGRAAFPGAPGEGPEARGPSLGEDTKEADLPEPSEKQPA  360
isoform 6    PTFHVEITPNVQKEQAHSEEHLGRAAFPGAPGEGPEARGPSLGEDTKEADLPEPSEKQPA  360
isoform 1    ------------------------------------------------------------
fetal        ------------------------------------------------------------ isoform 2    ----------------------------------ARMVSKSKDGTGSDDKKAK        143
isoform 3    ---------------------------------ARMVSKSKDGTGSDDKKAK-         85
isoform 4    ---------------------------------ARMVSKSKDGTGSDDKKAK-         85
isoform 5    ---------------------------------ARMVSKSKDGTGSDDKKAK-        114
isoform 6    AAPRGKPVSKPVSRVPQLKARMVSKSKDGTGSDDKKAKTSTRSSAKTLKNRPCLSPKHPTPGSS  420
isoform 1    AAPRGKPVSRVPQLKARMVSKSKDGTGSDDKKAKTSTRSSAKTLKNRPCLSPKHPTPGSS  420
fetal        ---------------------------------ARMVSKSKDGTGSDDKKAK-
                                              ********************
```

Figure 6C

```
isoform 2   ------------------------------------------------------------GADGKTKIATPRGAAPPGQK 163
isoform 3   ------------------------------------------------------------GADGKTKIATPRGAAPPGQK 105
isoform 4   ------------------------------------------------------------GADGKTKIATPRGAAPPGQK 105
isoform 5   ------------------------------------------------------------GADGKTKIATPRGAAPPGQK 134
isoform 6   DPLIQPSSPAVCPEPPSSPKHVSSVTSRTGSSGAKEMKLKGADGKTKIATPRGAAPPGQK 480
isoform 1   DPLIQPSSPAVCPEPPSSPKHVSSVTSRTGSSGAKEMKLKGADGKTKIATPRGAAPPGQK 480
fetal       ------------------------------------------------------------GADGKTKIATPRGAAPPGQK
                                                                        ******************** isoform 2   GQANATRIPAKTPPAPKTPPAPKTPPSS--------------------GEPPKSGDRSGYSSPGSSPGT 205
isoform 3   GQANATRIPAKTPPAPKTPPAPKTPPSS--------------------GEPPKSGDRSGYSSPGSSPGT 147
isoform 4   GQANATRIPAKTPPAPKTPPAPKTPPSS--------------------GEPPKSGDRSGYSSPGSSPGT 147
isoform 5   GQANATRIPAKTPPAPKTPPAPKTPPSS--------------------GEPPKSGDRSGYSSPGSSPGT 176
isoform 6   GQANATRIPAKTPPAPKTPPAPKTPPSSATKQVQRRPPPAGPRSERGEPPKSGDRSGYSSPGSSPGT 540
isoform 1   GQANATRIPAKTPPAPKTPPAPKTPPSS--------------------GEPPKSGDRSGYSSPGSSPGT 522
fetal       GQANATRIPAKTPPAPKTPPAPKTPPSS--------------------GEPPKSGDRSGYSSPGSSPGT
            **************************                    ****************** isoform 2   PGSRSRTPSLPTPPTREPKKVAVVRTPPKSPSSAKSRLQTAPVPMPDLKNVKSKIGSTEN 265
isoform 3   PGSRSRTPSLPTPPTREPKKVAVVRTPPKSPSSAKSRLQTAPVPMPDLKNVKSKIGSTEN 207
isoform 4   PGSRSRTPSLPTPPTREPKKVAVVRTPPKSPSSAKSRLQTAPVPMPDLKNVKSKIGSTEN 207
isoform 5   PGSRSRTPSLPTPPTREPKKVAVVRTPPKSPSSAKSRLQTAPVPMPDLKNVKSKIGSTEN 236
isoform 6   PGSRSRTPSLPTPPTREPKKVAVVRTPPKSPSSAKSRLQTAPVPMPDLKNVKSKIGSTEN 600
isoform 1   PGSRSRTPSLPTPPTREPKKVAVVRTPPKSPSSAKSRLQTAPVPMPDLKNVKSKIGSTEN 582
fetal       PGSRSRTPSLPTPPTREPKKVAVVRTPPKSPSSAKSRLQTAPVPMPDLKNVKSKIGSTEN
            ************************************************************
```

Figure 6D

```
isoform 2  LKHQPGGGKRVQIINKKLDLSNVQSKCGSKDNIKHVPGGGSVQIVYKPVDLSKVTSKCGSL  325
isoform 3  LKHQPGGGKRVQIINKKLDLSNVQSKCGSKDNIKHVPGGGSVQIVYKPVDLSKVTSKCGSL  267
isoform 4  LKHQPGGGK---------------------------------VQIVYKPVDLSKVTSKCGSL  236
isoform 5  LKHQPGGGKRVQIINKKLDLSNVQSKCGSKDNIKHVPGGGSVQIVYKPVDLSKVTSKCGSL  296
isoform 6  LKHQPGGGKRVQIINKKLDLSNVQSKCGSKDNIKHVPGGGSVQIVYKPVDLSKVTSKCGSL  660
isoform 1  LKHQPGGGKRVQIINKKLDLSNVQSKCGSKDNIKHVPGGGSVQIVYKPVDLSKVTSKCGSL  642
fetal      LKHQPGGGK---------------------------------VQIVYKPVDLSKVTSKCGSL
           *******                                 **************** isoform 2  GNIHHKPGGGQVEVKSEKLDFKDRVQSKIGSLDNITHVPGGGNKKIETHKLTFRENAKAK  385
isoform 3  GNIHHKPGGGQVEVKSEKLDFKDRVQSKIGSLDNITHVPGGGNKKIETHKLTFRENAKAK  327
isoform 4  GNIHHKPGGGQVEVKSEKLDFKDRVQSKIGSLDNITHVPGGGNKKIETHKLTFRENAKAK  296
isoform 5  GNIHHKPGGGQVEVKSEKLDFKDRVQSKIGSLDNITHVPGGGNKKIETHKLTFRENAKAK  356
isoform 6  GNIHHKPGGGQVEVKSEKLDFKDRVQSKIGSLDNITHVPGGGNKKIETHKLTFRENAKAK  720
isoform 1  GNIHHKPGGGQVEVKSEKLDFKDRVQSKIGSLDNITHVPGGGNKKIETHKLTFRENAKAK  702
fetal      GNIHHKPGGGQVEVKSEKLDFKDRVQSKIGSLDNITHVPGGGNKKIETHKLTFRENAKAK
           ************************************************************ isoform 2  TDHGAEIVYKSPVVSGDTSPRHLSNVSSTGSIDMVDSPQLATLADEVSASLAKQGL  441
isoform 3  TDHGAEIVYKSPVVSGDTSPRHLSNVSSTGSIDMVDSPQLATLADEVSASLAKQGL  383
isoform 4  TDHGAEIVYKSPVVSGDTSPRHLSNVSSTGSIDMVDSPQLATLADEVSASLAKQGL  352
isoform 5  TDHGAEIVYKSPVVSGDTSPRHLSNVSSTGSIDMVDSPQLATLADEVSASLAKQGL  412
isoform 6  TDHGAEIVYKSPVVSGDTSPRHLSNVSSTGSIDMVDSPQLATLADEVSASLAKQGL  776
isoform 1  TDHGAEIVYKSPVVSGDTSPRHLSNVSSTGSIDMVDSPQLATLADEVSASLAKQGL  758
fetal      TDHGAEIVYKSPVVSGDTSPRHLSNVSSTGSIDMVDSPQLATLADEVSASLAKQGL
           *******************************************************
```

Figure 17
Table 4: Binding of IPN002 variants to Tau proteins

| Antibody | Tau383 | eTau1a | eTau1b | eTau2 | eTau3 | eTau4 |
|---|---|---|---|---|---|---|
| | | | | KD (mol) (M) | | |
| IPN002 | 1.83E-10 | 2.94E-10 | 7.37E-10 | 4.65E-10 | 3.58E-10 | 5.77E-10 |
| hIPN002 | 1.21E-10 | 2.12E-10 | 5.58E-10 | 3.61E-10 | 3.21E-10 | 6.33E-10 |
| hIPN002-1 | 1.75E-10 | 2.91E-10 | 5.90E-10 | 4.44E-10 | 4.78E-10 | 7.61E-10 |
| hIPN002-2 | 2.86E-10 | 2.52E-10 | 5.97E-10 | 4.27E-10 | 2.69E-10 | 8.69E-10 |
| hIPN002-3 | 2.42E-10 | 2.81E-10 | 2.15E-10 | 2.25E-10 | 3.69E-10 | 3.21E-10 |
| hIPN002-4 | 1.99E-10 | 3.27E-10 | 2.29E-10 | 2.83E-10 | 2.94E-10 | 3.94E-10 |
| hIPN002-5 | 2.23E-10 | 3.27E-10 | 2.87E-10 | 2.61E-10 | 2.19E-10 | 4.11E-10 |
| hIPN002-6 | 2.48E-10 | 3.43E-10 | 5.20E-10 | 3.54E-10 | 4.18E-10 | 6.71E-10 |
| hIPN002-7 | 2.36E-10 | 2.41E-10 | 5.29E-10 | 7.05E-10 | 4.54E-10 | 9.21E-10 |
| hIPN002-8 | 2.58E-10 | 2.82E-10 | 6.14E-10 | 4.08E-10 | 5.89E-10 | 7.01E-10 |
| hIPN002-9 | 2.24E-10 | 2.20E-10 | 6.89E-10 | 4.71E-10 | 4.69E-10 | 6.65E-10 |
| hIPN002-10 | 2.55E-10 | 2.16E-10 | 3.82E-10 | 4.47E-10 | 3.81E-10 | 5.86E-10 |
| hIPN002-11 | 1.87E-10 | 1.98E-10 | 3.59E-10 | 4.05E-10 | 2.80E-10 | 4.98E-10 |
| hIPN002-12 | 1.60E-10 | 1.91E-10 | 4.83E-10 | 4.51E-10 | 2.91E-10 | 4.67E-10 |
| hIPN002-13 | 2.76E-10 | 1.78E-10 | 3.13E-10 | 4.73E-10 | 6.36E-10 | 6.29E-10 |
| hIPN002-14 | 3.79E-10 | 3.25E-10 | 5.35E-10 | 5.64E-10 | 4.62E-10 | 1.03E-09 |

Figure 18
Table 5: Binding of humanized IPN002 variants to Tau383

| Antibody | $K_D$ (M) | $k_a$ (1/Ms) | $k_d$ (1/s) |
|---|---|---|---|
| | 4.26E-11 | 2.06E+05 | 8.75E-06 |
| | 4.46E-10 | 1.96E+05 | 8.74E-05 |
| | 1.28E-09 | 1.82E+05 | 2.33E-04 |
| | 5.71E-10 | 1.67E+05 | 9.52E-05 |
| | 4.67E-10 | 2.14E+05 | 1.00E-04 |
| | 2.32E-10 | 2.05E+05 | 4.75E-05 |
| | 1.73E-09 | 1.34E+05 | 2.32E-04 |
| | 1.66E-09 | 1.42E+05 | 2.36E-04 |
| | 1.99E-09 | 1.29E+05 | 2.57E-04 |
| | 5.77E-10 | 1.85E+05 | 1.07E-04 |
| | 1.69E-10 | 1.87E+05 | 3.15E-05 |
| | 4.75E-10 | 2.11E+05 | 1.00E-04 |
| | 2.12E-09 | 1.40E+05 | 2.97E-04 |
| | 1.88E-09 | 1.63E+05 | 3.07E-04 |
| | 5.71E-10 | 1.64E+05 | 9.39E-05 |
| | 8.12E-10 | 1.56E+05 | 1.26E-04 |
| | 2.06E-10 | 2.33E+05 | 4.78E-05 |

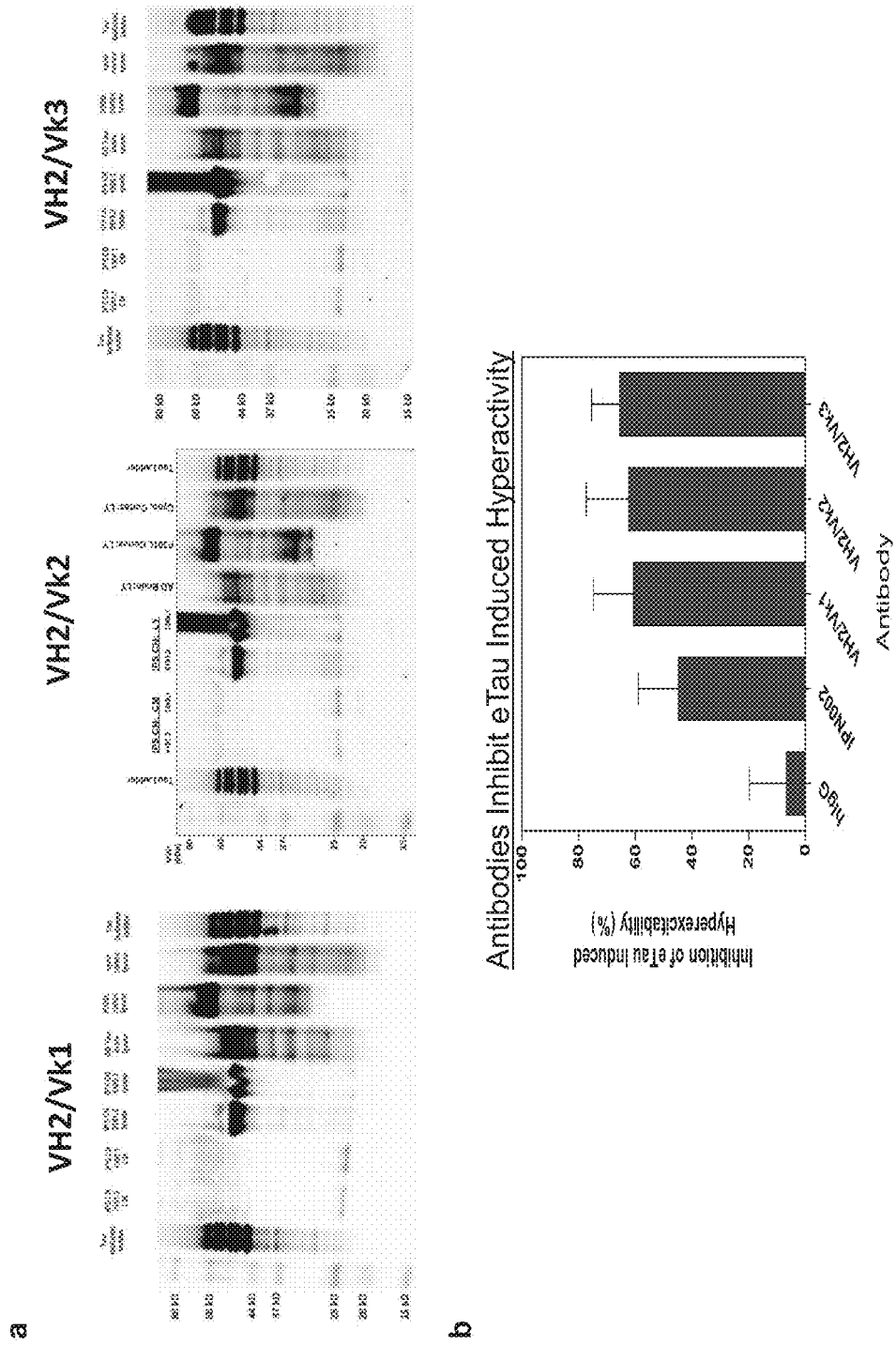
Figure 19 Antibodies Bind to eTau in Conditioned Media and Brain Lysates (Cyno and Human)

Figure 20

```
fetal   MAEPRQFFEVMEDHAGTYGLGDRKDQGGYTMHQDQEGDTDAGLKAEEAGIGDTPSLEDEA
#1a      AEPRQFFEVMEDHAGTYGLGDRKDQGGYTMHQDQEGDTDAGLKAEEAGIGDTPSLEDEA
#1b      AEPRQFFEVMEDHAGTYGLGDRKDQGGYTMHQDQEGDTDAGLKAEEAGIGDTPSLEDEA
#2       AEPRQFFEVMEDHAGTYGLGDRKDQGGYTMHQDQEGDTDAGLKAEEAGIGDTPSLEDEA
#3       AEPRQFFEVMEDHAGTYGLGDRKDQGGYTMHQDQEGDTDAGLKAEEAGIGDTPSLEDEA
4       AEPRQFFEVMEDHAGTYGLGDRKDQGGYTMHQDQEGDTDAGLKAEEAGIGDTPSLEDEA fetal   AGHVTQARMVSKSKDGTGSDDKKAKGADGKTKIATPRGAAPPGQKGQANATRIPAKTPPA
1a     AGHVTQARMVSKSKDGTGSDDKKAKGADGKTKIATPRGAAPPGQKGQANATRIPAKTPPA
#1b     AGHVTQARMVSKSKDGTGSDDKKAKGADGKTKIATPRGAAPPGQKGQANATRIPAKTPPA
#2      AGHVTQARMVSKSKDGTGSDDKKAKGADGKTKIATPRGAAPPGQKGQANATRIPAKTPPA
#3      AGHVTQARMVSKSKDGTGSDDKKAKGADGKTKIATPRGAAPPGQKGQANATRIPAKTPPA
#4      AGHVTQAR (68)

fetal   PKTPPSSGEPPKSGDRSGYSSPGSPGTPGSRSRTPSLPTPPTREPKKVAVVRTPPKSPSSA
#1a     PKTPPSSGEPPKSGDRSGYSSPGSPGTPGSRSRTPSLPTPPTREPK (166)
#1b     PKTPPSSGEPPKSGDRSGYSSPGSPGTPGSRSRTPSLPTPPTREPKKVAVVRTPPKSPSSA
#2      PKTPPSSGEPPKSGDRSGYSSPGSPGTPGSR (151)
#3      PK (122)

fetal   KSRLQTAPVPMPDLKNVKSKIGSTENLKHQPGGGKVQIVYKPVDLSKVTSKCGSLGNIHHK
#1b     KSRLQTAPVPMPDLK-------------------VQIVYKPVDLSK (228)

fetal   PGGGQVEVKSEKLDFKDRVQSKIGSLDNITHVPGGGNKKIETHKLTFRENAKAKTDHGAEI fetal   VYKSPVVSGDTSPRHLSNVSSTGSIDMVDSPQLATLADEVSASLAKQGL
```

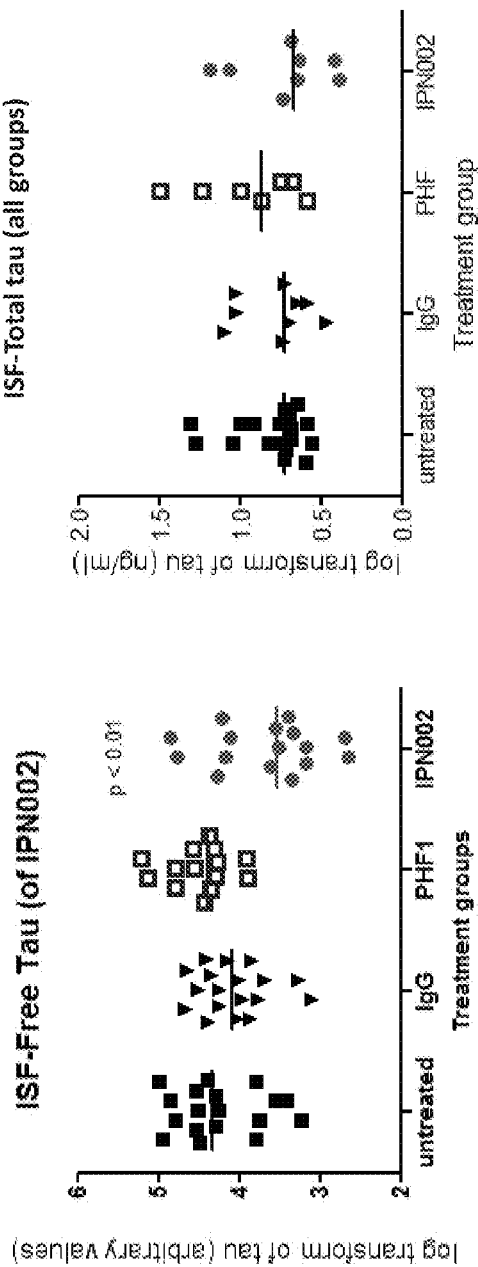
Figure 23. Free and Total Tau Levels in ISF in P301L Tau Biomarker Study

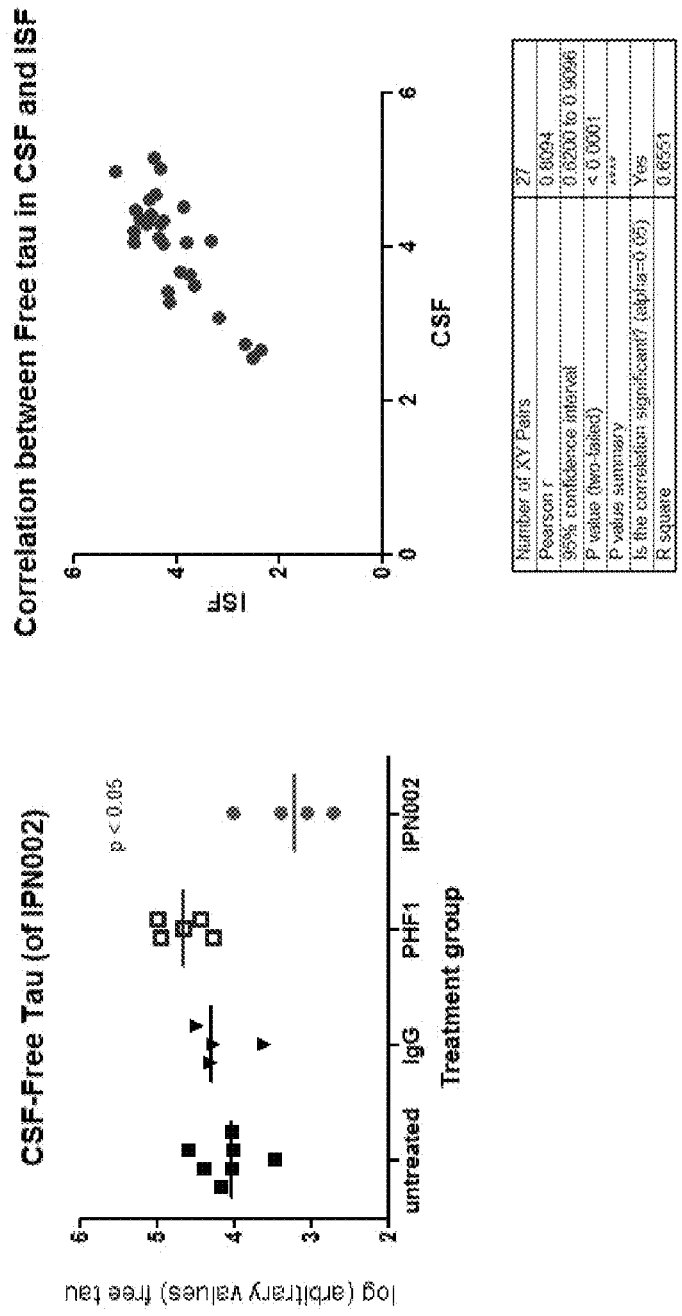
Figure 24. Strong Correlation between Free Tau Levels in CSF and ISF in P301L Tau Biomarker Study
- Free tau (of IPN002) is significantly reduced in CSF in IPN002 treatment group
- Free tau in CSF correlates well with free tau in ISF

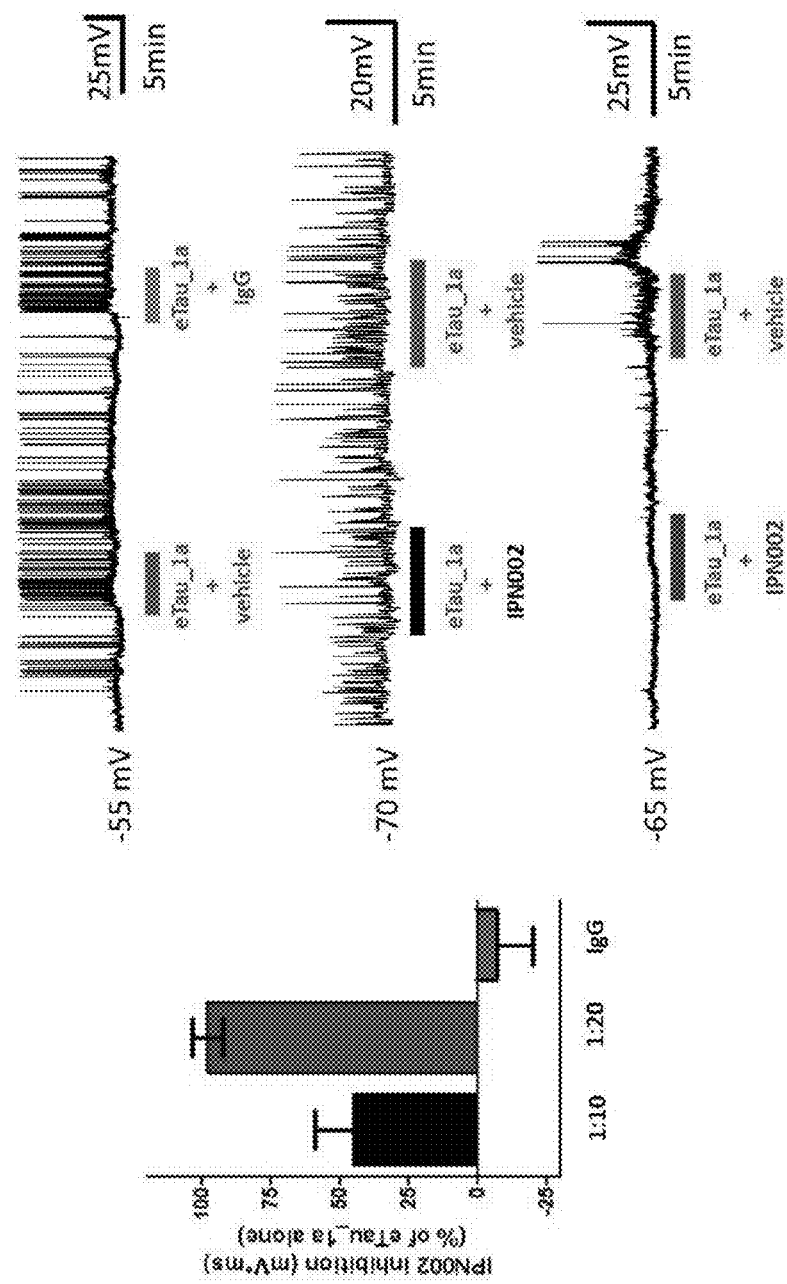
Figure 25. eTau Induced Neuronal Hyperactivity is Blocked by IPN002

Figure 26. Tau Fragments are Present in CSF from NFL Players with Likely CTE (Chronic Traumatic Encephalopathy)
WB of eTau
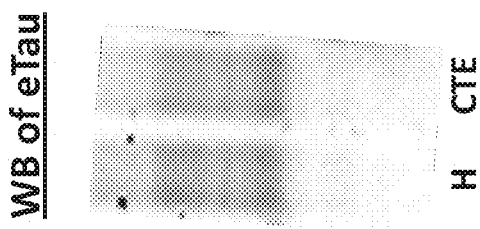
H    CTE
IPN002 affinity isolation from pooled healthy and CTE CSF followed by IPN001 Western blotting

SEQUENCE LISTING

<160> NUMBER OF SEQ ID NOS: 71

<210> SEQ ID NO 1
<211> LENGTH: 16
<212> TYPE: PRT
<213> ORGANISM: Artificial Sequence
<220> FEATURE:
<223> OTHER INFORMATION: Synthetic amino acid sequence

<400> SEQUENCE: 1

Arg Ser Ser Gln Thr Ile Leu His Ser Asn Gly Asn Thr Tyr Leu Glu

```
<210> SEQ ID NO 2
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 2

Lys Val Ser Lys Arg Phe Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 3

Phe Gln Gly Ser Leu Val Pro Trp Ala
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 4

Ser Tyr Gly Met Ser
1               5

<210> SEQ ID NO 5
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 5

Thr Ile Ser Ser Ser Gly Ser Arg Thr Tyr Phe Pro Asp Ser Val Lys
1               5                   10                  15

Gly

<210> SEQ ID NO 6
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 6

Thr Trp Asp Gly Ala Met Asp Tyr
1               5

<210> SEQ ID NO 7
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 7
```

Lys Ser Ser Gln Ser Ile Val His Ser Asn Gly Asn Thr Tyr Leu Glu
1               5                   10                  15

<210> SEQ ID NO 8
<211> LENGTH: 7
<212> TYPE: PRT
<213> ORGANISM: Artificial sequence
<220> FEATURE:
<223> OTHER INFORMATION: Synthetic amino acid sequence

<400> SEQUENCE: 8

Lys Val Ser Asn Arg Phe Ser
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 9

Phe Gln Gly Ser Leu Val Pro Trp Ala
1               5

<210> SEQ ID NO 10
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 10

Lys Tyr Gly Met Ser
1               5

<210> SEQ ID NO 11
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 11

Thr Ile Ser Ser Ser Gly Ser Arg Thr Tyr Tyr Pro Asp Ser Val Lys
1               5                   10                  15

Gly

<210> SEQ ID NO 12
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 12

Ser Trp Asp Gly Ala Met Asp Tyr
1               5

<210> SEQ ID NO 13
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 13

Asp Val Leu Met Thr Gln Thr Pro Leu Ser Leu Ala Val Asn Leu Gly
1               5                   10                  15

Asp Gln Ala Ser Leu Ser Cys Arg Ser Ser Gln Thr Ile Leu His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Ile Tyr Tyr Cys Phe Gln Gly
                85                  90                  95

Ser Leu Val Pro Trp Ala Phe Gly Gly Gly Thr Lys Leu Glu Ile Lys
            100                 105                 110

<210> SEQ ID NO 14
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 14

Glu Val Gln Leu Val Glu Ser Gly Glu Asp Leu Val Lys Pro Gly Gly
1               5                   10                  15

Ser Leu Lys Leu Ser Cys Val Ala Ser Gly Phe Ala Phe Ser Ser Tyr
            20                  25                  30

Gly Met Ser Trp Val Arg Gln Thr Pro Asp Met Arg Leu Glu Trp Val
        35                  40                  45

Ala Thr Ile Ser Ser Gly Ser Arg Thr Tyr Phe Pro Asp Ser Val
    50                  55                  60

Lys Gly Arg Leu Thr Ile Ser Arg Asp Asn Asp Lys Asn Ile Leu Tyr
65                  70                  75                  80

Leu Gln Met Ser Ser Leu Arg Ser Glu Asp Thr Ala Met Tyr Tyr Cys
                85                  90                  95

Thr Ile Thr Trp Asp Gly Ala Met Asp Tyr Trp Gly Arg Gly Ile Ser
            100                 105                 110

Val Thr Val Ser Ser
        115

<210> SEQ ID NO 15
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 15

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Val Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Thr Tyr Tyr Cys Phe Gln Gly
                        85                  90                  95

Ser Leu Val Pro Trp Ala Phe Gly Gly Gly Thr Lys Leu Glu Ile Lys
            100                 105                 110
```

<210> SEQ ID NO 16
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 16

```
Glu Val His Leu Val Glu Ser Gly Gly Ala Leu Val Lys Pro Gly Gly
1               5                   10                  15

Ser Leu Lys Leu Ser Cys Ala Ala Ser Gly Phe Ser Phe Ser Lys Tyr
                20                  25                  30

Gly Met Ser Trp Val Arg Gln Thr Pro Asp Lys Arg Leu Glu Trp Val
            35                  40                  45

Ala Thr Ile Ser Ser Gly Ser Arg Thr Tyr Tyr Pro Asp Ser Val
        50                  55                  60

Lys Gly Gln Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Ile Ser Trp Asp Gly Ala Met Asp Tyr Trp Gly Gln Gly Thr Ser
            100                 105                 110

Val Thr Val Ser Ser
        115
```

<210> SEQ ID NO 17
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 17

```
gatgttttga tgacccaaac tccgctctcc ctggcagtca atcttggaga tcaagcctcc    60
ctctcttgca gatcgagtca gactatttta catagtaatg gaaataccta tttagaatgg   120
tatttgcaga aaccaggcca gtctccaaga ctcctgatct acaaagtttc taaacgattt   180
tctggggtcc cagacaggtt cagtggcagt ggatcaggga cagatttcac actcaagatc   240
agcagagtgg aggctgacga tctgggaatt tattactgct ttcaaggttc acttgttcct   300
tgggcgttcg gtggaggcac caagctggaa atcaaa                              336
```

<210> SEQ ID NO 18
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 18

```
gaggtgcagt tggtggagtc tggggaagac ttagtgaagc ctggagggtc cctgaaactc    60
tcctgtgtcg cttctggatt cgctttcagt agctatggca tgtcttgggt tcgccagact   120
ccagacatga ggctggagtg ggtcgcaaca attagtagca gtggtagtcg cacctacttt   180
```

```
ccagacagtg tgaaggggcg actcaccatc tccagagaca atgacaagaa catcctatac    240
ctacaaatga gcagtctgag gtctgaggac acagccatgt actattgtac gattacctgg    300
gacggtgcta tggactactg gggtcgtgga atatcagtca ccgtctcctc a             351
```

<210> SEQ ID NO 19
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 19

```
gatgttttga tgacccaaac tccactctcc ctgcctgtca gtcttggaga tcaagcctcc     60
atctcttgca aatctagtca gagcattgta catagtaatg aaacacccta tttagaatgg    120
tacctgcaga aaccaggcca gtctccaaag ctcctggtct acaaagtttc caatcgattt    180
tctggggtcc cagacaggtt cagtggcagt ggatcaggga cagatttcac actcaagatc    240
agcagagtgg aggctgagga tctgggaact tattactgct ttcaaggttc acttgttcct    300
tgggcgttcg gtggaggcac caagctggaa atcaaa                              336
```

<210> SEQ ID NO 20
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 20

```
gaggttcatc tggtggagtc tgggggagcc ttagtgaagc ctggagggtc cctgaaactc     60
tcctgtgcag cctctggatt cagtttcagt aaatatggca tgtcttgggt tcgccagact    120
ccagacaaga ggctggagtg ggtcgcaacc attagtagta gtgggagtcg cacctactat    180
ccagacagtg tgaaggggcc attcaccatc tccagagaca atgccaagaa caccctgtac    240
ctgcaaatga gcagtctgaa gtctgaggac acagccatgt attactgttc aattagctgg    300
gacggtgcta tggactactg gggtcaaggg acctcagtca ccgtctcctc a             351
```

<210> SEQ ID NO 21
<211> LENGTH: 441
<212> TYPE: PRT
<213> ORGANISM: Artificial sequence
<220> FEATURE:
<223> OTHER INFORMATION: Synthetic amino acid sequence

<400> SEQUENCE: 21

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95
```

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 22
<211> LENGTH: 383
<212> TYPE: PRT
<213> ORGANISM: Artificial sequence
<220> FEATURE:
<223> OTHER INFORMATION: Synthetic amino acid sequence

<400> SEQUENCE: 22

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Tyr Thr Met His
            20                  25                  30

Gln Asp Gln Glu Gly Asp Thr Asp Ala Gly Leu Lys Ala Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Ser Ser Gly
        115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 23
<211> LENGTH: 352
<212> TYPE: PRT
<213> ORGANISM: Artificial sequence
<220> FEATURE:
<223> OTHER INFORMATION: Synthetic amino acid sequence

<400> SEQUENCE: 23

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 24
<211> LENGTH: 412
<212> TYPE: PRT
<213> ORGANISM: Artificial sequence
<220> FEATURE:
<223> OTHER INFORMATION: Synthetic amino acid sequence

<400> SEQUENCE: 24

Met Ala Glu Pro Arg Gln Glu Phe Glu Val Met Glu Asp His Ala Gly
1               5                   10                  15

```
Thr Tyr Gly Leu Gly Asp Arg Lys Gln Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Gly His Val Thr Gln Ala
            85                  90                  95

Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
        130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Arg Thr Pro Pro Lys Ser Pro Ser
        195                 200                 205

Ser Ala Lys Ser Arg Leu Gln Thr Ala Pro Val Pro Met Pro Asp Leu
210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
            325                 330                 335

Gly Gly Asn Lys Lys Ile Glu Thr His Lys Leu Thr Phe Arg Glu Asn
        340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
        370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 25
<211> LENGTH: 776
<212> TYPE: PRT
```

<213> ORGANISM: Artificial sequence
<220> FEATURE:
<223> OTHER INFORMATION: Synthetic amino acid sequence

<400> SEQUENCE: 25

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Ala Gly Ile Gly Asp Thr Pro
        100                 105                 110

Ser Leu Glu Asp Glu Ala Ala Gly His Val Thr Gln Glu Pro Glu Ser
    115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
            165                 170                 175

Asp Thr Glu Gly Gly Arg His Ala Pro Glu Leu Leu Lys His Gln Leu
        180                 185                 190

Leu Gly Asp Leu His Gln Glu Gly Pro Pro Leu Lys Gly Ala Gly Gly
    195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
        260                 265                 270

Ser Lys Val Ser Thr Glu Ile Pro Ala Ser Glu Pro Asp Gly Pro Ser
    275                 280                 285

Val Gly Arg Ala Lys Gly Gln Asp Ala Pro Leu Glu Phe Thr Phe His
290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
            325                 330                 335

Ala Arg Gly Pro Ser Leu Gly Glu Asp Thr Lys Glu Ala Asp Leu Pro
        340                 345                 350

Glu Pro Ser Glu Lys Gln Pro Ala Ala Ala Pro Arg Gly Lys Pro Val
    355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
```

```
            385                 390                 395                 400
        Ala Lys Thr Leu Lys Asn Arg Pro Cys Leu Ser Pro Lys His Pro Thr
                        405                 410                 415
        Pro Gly Ser Ser Asp Pro Leu Ile Gln Pro Ser Ser Pro Ala Val Cys
                        420                 425                 430
        Pro Glu Pro Pro Ser Ser Pro Lys His Val Ser Ser Val Thr Ser Arg
                        435                 440                 445
        Thr Gly Ser Ser Gly Ala Lys Glu Met Lys Leu Lys Gly Ala Asp Gly
                        450                 455                 460
        Lys Thr Lys Ile Ala Thr Pro Arg Gly Ala Ala Pro Pro Gly Gln Lys
        465                 470                 475                 480
        Gly Gln Ala Asn Ala Thr Arg Ile Pro Ala Lys Thr Pro Pro Ala Pro
                        485                 490                 495
        Lys Thr Pro Pro Ser Ser Ala Thr Lys Gln Val Gln Arg Arg Pro Pro
                        500                 505                 510
        Pro Ala Gly Pro Arg Ser Glu Arg Gly Glu Pro Pro Lys Ser Gly Asp
                        515                 520                 525
        Arg Ser Gly Tyr Ser Ser Pro Gly Ser Pro Gly Thr Pro Gly Ser Arg
                        530                 535                 540
        Ser Arg Thr Pro Ser Leu Pro Thr Pro Pro Thr Arg Glu Pro Lys Lys
        545                 550                 555                 560
        Val Ala Val Val Arg Thr Pro Pro Lys Ser Pro Ser Ala Lys Ser
                        565                 570                 575
        Arg Leu Gln Thr Ala Pro Val Pro Met Pro Asp Leu Lys Asn Val Lys
                        580                 585                 590
        Ser Lys Ile Gly Ser Thr Glu Asn Leu Lys His Gln Pro Gly Gly Gly
                        595                 600                 605
        Lys Val Gln Ile Ile Asn Lys Lys Leu Asp Leu Ser Asn Val Gln Ser
                        610                 615                 620
        Lys Cys Gly Ser Lys Asp Asn Ile Lys His Val Pro Gly Gly Gly Ser
        625                 630                 635                 640
        Val Gln Ile Val Tyr Lys Pro Val Asp Leu Ser Lys Val Thr Ser Lys
                        645                 650                 655
        Cys Gly Ser Leu Gly Asn Ile His His Lys Pro Gly Gly Gly Gln Val
                        660                 665                 670
        Glu Val Lys Ser Glu Lys Leu Asp Phe Lys Asp Arg Val Gln Ser Lys
                        675                 680                 685
        Ile Gly Ser Leu Asp Asn Ile Thr His Val Pro Gly Gly Gly Asn Lys
                        690                 695                 700
        Lys Ile Glu Thr His Lys Leu Thr Phe Arg Glu Asn Ala Lys Ala Lys
        705                 710                 715                 720
        Thr Asp His Gly Ala Glu Ile Val Tyr Lys Ser Pro Val Val Ser Gly
                        725                 730                 735
        Asp Thr Ser Pro Arg His Leu Ser Asn Val Ser Ser Thr Gly Ser Ile
                        740                 745                 750
        Asp Met Val Asp Ser Pro Gln Leu Ala Thr Leu Ala Asp Glu Val Ser
                        755                 760                 765
        Ala Ser Leu Ala Lys Gln Gly Leu
                770                 775

<210> SEQ ID NO 26
<211> LENGTH: 758
<212> TYPE: PRT
<213> ORGANISM: Artificial sequence
```

<220> FEATURE:
<223> OTHER INFORMATION: Synthetic amino acid sequence

<400> SEQUENCE: 26

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
            405                 410                 415

Pro Gly Ser Ser Asp Pro Leu Ile Gln Pro Ser Ser Pro Ala Val Cys
        420                 425                 430

Pro Glu Pro Ser Ser Pro Lys His Val Ser Ser Val Thr Ser Arg
    435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
            515                 520                 525

Thr Pro Ser Leu Pro Thr Pro Pro Thr Arg Glu Pro Lys Lys Val Ala
        530                 535                 540

Val Val Arg Thr Pro Pro Lys Ser Pro Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 27
<211> LENGTH: 352
<212> TYPE: PRT
<213> ORGANISM: Artificial sequence
<220> FEATURE:
<223> OTHER INFORMATION: Synthetic amino acid sequence

<400> SEQUENCE: 27

```
Met Ala Glu Pro Arg Gln Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
            275                 280                 285

Phe Arg Glu Asn Ala Lys Ala Lys Thr Asp His Gly Ala Glu Ile Val
290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350
```

<210> SEQ ID NO 28
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 28
gaggttcatc tggtggagtc tgggggagcc ttagtgaagc ctggagggtc cctgagactc      60

```
tcctgtgcag cctctggatt cagtttcagt aaatatggca tgtcttgggt tcgccaggcc    120
ccaggcaagg gcctggagtg gtcgcaacc attagtagta gtgggagtcg cacctactat     180
ccagacagtg tgaagggcag attcaccatc tccagagaca atgccaagaa caccctgtac    240
ctgcaaatga gcagtctgaa gtctgaggac acagccatgt attactgttc aattagctgg    300
gacggtgcta tggactactg gggtcaaggg acctcagtca ccgtctcctc a             351
```

<210> SEQ ID NO 29
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 29

```
gaggttcatc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg gtcgcaacc attagtagta gtgggagtcg cacctactat     180
ccagacagtg tgaagggcag attcaccatc tccagagaca atgccaagaa caccctgtac    240
ctgcaaatga acagtctgag agccgaggac acagccatgt attactgttc aattagctgg    300
gacggtgcta tggactactg gggtcaaggg accaccgtca ccgtctcctc a             351
```

<210> SEQ ID NO 30
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 30

```
gaggttcagc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg gtcgcaacc attagtagta gtgggagtcg cacctactat     180
ccagacagtg tgaagggcag attcaccatc tccagagaca atgccaagaa caccctgtac    240
ctgcaaatga acagtctgag agccgaggac acagccatgt attactgttc aattagctgg    300
gacggtgcta tggactactg gggtcaaggg accaccgtca ccgtctcctc a             351
```

<210> SEQ ID NO 31
<211> LENGTH: 351
<212> TYPE: DNA
<213> ORGANISM: Artificial sequence
<220> FEATURE:
<223> OTHER INFORMATION: Synthetic nucleic acid sequence

<400> SEQUENCE: 31

```
gaggttcagc tggtggagtc tgggggagcc ttagtgaagc ctggagggtc cctgagactc    60
tcctgtgcag cctctggatt cagtttcagt aaatatggca tgtcttgggt tcgccaggcc    120
ccaggcaagg gcctggagtg gtcgcaacc attagtagta gtgggagtcg cacctactat     180
ccagacagtg tgaagggcag attcaccatc tccagagaca atgccaagaa caccctgtac    240
ctgcaaatga acagtctgag agccgaggac acagccatgt attactgtgc cattagctgg    300
gacggtgcta tggactactg gggtcaaggg accaccgtca ccgtctcctc a             351
```

<210> SEQ ID NO 32
<211> LENGTH: 336

```
<212> TYPE: DNA
<213> ORGANISM: Artificial sequence
<220> FEATURE:
<223> OTHER INFORMATION: Synthetic nucleic acid sequence

<400> SEQUENCE: 32
gatgttttga tgacccaaag cccactctcc ctgcctgtca cccttggaca gcccgcctcc    60
atctcttgca aatctagtca gagcattgta catagtaatg gaaacaccta tttagaatgg   120
tacctgcaga aaccaggcca gtctccacag ctcctggtct acaaagtttc caatcgattt   180
tctggggtcc cagacagatt cagtggcagt ggatcaggga cagatttcac actcaagatc   240
agcagagtgg aggctgagga tgtgggaact tattactgct ttcaaggctc acttgttcct   300
tgggcgttcg gtggaggcac caaggtggaa atcaaa                             336

<210> SEQ ID NO 33
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 33
gatgttgtga tgacccaaag cccactctcc ctgcctgtca cccttggaca gcccgcctcc    60
atctcttgca aatctagtca gagcattgta catagtaatg gaaacaccta tttagaatgg   120
tacctgcaga aaccaggcca gtctccacag ctcctggtct acaaagtttc caatcgattt   180
tctggggtcc cagacagatt cagtggcagt ggatcaggga cagatttcac actcaagatc   240
agcagagtgg aggctgagga tgtgggaact tattactgct ttcaaggctc acttgttcct   300
tgggcgttcg gtggaggcac caaggtggaa atcaaa                             336

<210> SEQ ID NO 34
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 34
gatgttgtga tgacccaaag cccactctcc ctgcctgtca cccttggaca gcccgcctcc    60
atctcttgca aatctagtca gagcattgta catagtaatg gaaacaccta tttagaatgg   120
tacctgcaga aaccaggcca gtctccacag ctcctggtct acaaagtttc caatcgattt   180
tctggggtcc cagacagatt cagtggcagt ggatcaggga cagatttcac actcaagatc   240
agcagagtgg aggctgagga tgtgggagtg tattactgct ttcaaggctc acttgttcct   300
tgggcgttcg gtggaggcac caaggtggaa atcaaa                             336

<210> SEQ ID NO 35
<211> LENGTH: 336
<212> TYPE: DNA
<213> ORGANISM: Artificial sequence
<220> FEATURE:
<223> OTHER INFORMATION: Synthetic nucleic acid sequence

<400> SEQUENCE: 35
gatgttgtga tgacccaaag cccactctcc ctgcctgtca cccttggaca gcccgcctcc    60
atctcttgca aatctagtca gagcattgta catagtaatg gaaacaccta tttagaatgg   120
tacctgcaga aaccaggcca gtctccacag ctcctgatct acaaagtttc caatcgattt   180
```

```
tctggggtcc cagacagatt cagtggcagt ggatcaggga cagatttcac actcaagatc    240
agcagagtgg aggctgagga tgtgggagtg tattactgct ttcaaggctc acttgttcct    300
tgggcgttcg gtggaggcac caaggtggaa atcaaa                              336
```

<210> SEQ ID NO 36
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 36

```
Glu Val His Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ser Ile Ser Trp Asp Gly Ala Met Asp Tyr Trp Gly Gln Gly Thr Ser
            100                 105                 110

Val Thr Val Ser Ser
        115
```

<210> SEQ ID NO 37
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 37

```
Glu Val His Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ser Ile Ser Trp Asp Gly Ala Met Asp Tyr Trp Gly Gln Gly Thr Thr
            100                 105                 110

Val Thr Val Ser Ser
        115
```

<210> SEQ ID NO 38
<211> LENGTH: 117
<212> TYPE: PRT
<213> ORGANISM: Artificial sequence

```
<220> FEATURE:
<223> OTHER INFORMATION: Synthetic amino acid sequence

<400> SEQUENCE: 38

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ser Ile Ser Trp Asp Gly Ala Met Asp Tyr Trp Gly Gln Gly Thr Thr
            100                 105                 110

Val Thr Val Ser Ser
        115

<210> SEQ ID NO 39
<211> LENGTH: 117
<212> TYPE: PRT
<213> ORGANISM: Artificial sequence
<220> FEATURE:
<223> OTHER INFORMATION: Synthetic amino acid sequence

<400> SEQUENCE: 39

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Ser Phe Ser Lys Tyr
            20                  25                  30

Gly Met Ser Trp Val Arg Gln Ala Pro Gly Lys Gly Leu Glu Trp Val
        35                  40                  45

Ala Thr Ile Ser Ser Ser Gly Ser Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Ile Ser Trp Asp Gly Ala Met Asp Tyr Trp Gly Gln Gly Thr Thr
            100                 105                 110

Val Thr Val Ser Ser
        115

<210> SEQ ID NO 40
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 40

Asp Val Leu Met Thr Gln Ser Pro Leu Ser Leu Pro Val Thr Leu Gly
1               5                   10                  15

Gln Pro Ala Ser Ile Ser Cys Lys Ser Ser Gln Ser Ile Val His Ser
            20                  25                  30
```

```
Asn Gly Asn Thr Tyr Leu Glu Trp Tyr Leu Gln Lys Pro Gly Gln Ser
            35                  40                  45

Pro Gln Leu Leu Val Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Phe Gln Gly
                85                  90                  95

Ser Leu Val Pro Trp Ala Phe Gly Gly Gly Thr Lys Val Glu Ile Lys
            100                 105                 110

<210> SEQ ID NO 41
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 41

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Gln Leu Leu Val Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Phe Gln Gly
                85                  90                  95

Ser Leu Val Pro Trp Ala Phe Gly Gly Gly Thr Lys Val Glu Ile Lys
            100                 105                 110

<210> SEQ ID NO 42
<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 42

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
            35                  40                  45

Pro Gln Leu Leu Val Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Trp Ala Phe Gly Gly Gly Thr Lys Val Glu Ile Lys
            100                 105                 110

<210> SEQ ID NO 43
```

<211> LENGTH: 112
<212> TYPE: PRT
<213> ORGANISM: Artificial sequence
<220> FEATURE:
<223> OTHER INFORMATION: Synthetic amino acid sequence

<400> SEQUENCE: 43

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Leu Val Pro Trp Ala Phe Gly Gly Gly Thr Lys Val Glu Ile Lys
            100                 105                 110

<210> SEQ ID NO 44
<211> LENGTH: 171
<212> TYPE: PRT
<213> ORGANISM: Artificial sequence
<220> FEATURE:
<223> OTHER INFORMATION: Synthetic amino acid sequence

<400> SEQUENCE: 44

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys Thr Pro Pro Ser Ser Gly Glu
        115                 120                 125

Pro Pro Lys Ser Gly Asp Arg Ser Gly Tyr Ser Ser Pro Gly Ser Pro
    130                 135                 140

Gly Thr Pro Gly Ser Arg Ser Arg Thr Pro Ser Leu Pro Thr Pro Pro
145                 150                 155                 160

Thr Arg Glu Pro Lys Lys Val Ala Val Val Arg
                165                 170

<210> SEQ ID NO 45
<211> LENGTH: 175
<212> TYPE: PRT
<213> ORGANISM: Artificial sequence
<220> FEATURE:
<223> OTHER INFORMATION: Synthetic amino acid sequence

<400> SEQUENCE: 45

```
Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Ala Pro Lys Thr Pro Ser Ser Gly Glu
            115                 120                 125

Pro Pro Lys Ser Gly Asp Arg Ser Gly Tyr Ser Ser Pro Gly Ser Pro
    130                 135                 140

Gly Thr Pro Gly Ser Arg Ser Arg Thr Pro Ser Leu Pro Thr Pro Pro
145                 150                 155                 160

Thr Arg Glu Pro Lys Lys Val Ala Val Val Arg Thr Pro Pro Lys
                165                 170                 175
```

<210> SEQ ID NO 46
<211> LENGTH: 150
<212> TYPE: PRT
<213> ORGANISM: Artificial sequence
<220> FEATURE:
<223> OTHER INFORMATION: Synthetic amino acid sequence

<400> SEQUENCE: 46

```
Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Ala Pro Lys Thr Pro Ser Ser Gly Glu
            115                 120                 125

Pro Pro Lys Ser Gly Asp Arg Ser Gly Tyr Ser Ser Pro Gly Ser Pro
    130                 135                 140

Gly Thr Pro Gly Ser Arg
145                 150
```

<210> SEQ ID NO 47
<211> LENGTH: 121

```
<212> TYPE: PRT
<213> ORGANISM: Artificial sequence
<220> FEATURE:
<223> OTHER INFORMATION: Synthetic amino acid sequence

<400> SEQUENCE: 47

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg Met Val Ser Lys Ser Lys Asp Gly Thr Gly Ser Asp Asp
65                  70                  75                  80

Lys Lys Ala Lys Gly Ala Asp Gly Lys Thr Lys Ile Ala Thr Pro Arg
                85                  90                  95

Gly Ala Ala Pro Pro Gly Gln Lys Gly Gln Ala Asn Ala Thr Arg Ile
            100                 105                 110

Pro Ala Lys Thr Pro Pro Ala Pro Lys
            115                 120

<210> SEQ ID NO 48
<211> LENGTH: 67
<212> TYPE: PRT
<213> ORGANISM: Artificial sequence
<220> FEATURE:
<223> OTHER INFORMATION: Synthetic amino acid sequence

<400> SEQUENCE: 48

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu Gly Asp Thr Asp Ala Gly Leu Lys Ala Glu Glu Ala Gly
        35                  40                  45

Ile Gly Asp Thr Pro Ser Leu Glu Asp Glu Ala Ala Gly His Val Thr
    50                  55                  60

Gln Ala Arg
65

<210> SEQ ID NO 49
<211> LENGTH: 18
<212> TYPE: PRT
<213> ORGANISM: Artificial sequence
<220> FEATURE:
<223> OTHER INFORMATION: Synthetic amino acid sequence

<400> SEQUENCE: 49

Met Ala Glu Pro Arg Gln Glu Phe Glu Val Met Glu Asp His Ala Gly
1               5                   10                  15

Thr Tyr

<210> SEQ ID NO 50
<211> LENGTH: 5
<212> TYPE: PRT
<213> ORGANISM: Artificial sequence
<220> FEATURE:
<223> OTHER INFORMATION: Synthetic amino acid sequence
```

```
<400> SEQUENCE: 50

Gly Ser Gly Gly Ser
1               5

<210> SEQ ID NO 51
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 51

Gly Gly Gly Ser
1

<210> SEQ ID NO 52
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 52

Gly Gly Ser Gly
1

<210> SEQ ID NO 53
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 53

Gly Gly Ser Gly Gly
1               5

<210> SEQ ID NO 54
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 54

Gly Ser Gly Ser Gly
1               5

<210> SEQ ID NO 55
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 55

Gly Ser Gly Gly Gly
1               5

<210> SEQ ID NO 56
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 56
```

```
Gly Gly Gly Ser Gly
1               5

<210> SEQ ID NO 57
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 57

Gly Ser Ser Ser Gly
1               5

<210> SEQ ID NO 58
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 58

His His His His His
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic amino acid sequence

<400> SEQUENCE: 59

His His His His His His
1               5

<210> SEQ ID NO 60
<211> LENGTH: 10
<212> TYPE: PRT
<213> ORGANISM: Artificial sequence
<220> FEATURE:
<223> OTHER INFORMATION: Synthetic amino acid sequence

<400> SEQUENCE: 60

Glu Gln Lys Leu Ile Ser Glu Glu Asp Leu
1               5                   10

<210> SEQ ID NO 61
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 61

Asp Tyr Lys Asp Asp Asp Asp Lys
1               5

<210> SEQ ID NO 62
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 62
```

```
Trp Ser His Pro Gln Phe Glu Lys
1               5

<210> SEQ ID NO 63
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 63

Tyr Pro Tyr Asp Val Pro Asp Tyr Ala
1               5

<210> SEQ ID NO 64
<211> LENGTH: 5
<212> TYPE: PRT
<213> ORGANISM: Artificial sequence
<220> FEATURE:
<223> OTHER INFORMATION: Synthetic amino acid sequence

<400> SEQUENCE: 64

Arg Tyr Ile Arg Ser
1               5

<210> SEQ ID NO 65
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 65

Phe His His Thr
1

<210> SEQ ID NO 66
<211> LENGTH: 17
<212> TYPE: PRT
<213> ORGANISM: Artificial sequence
<220> FEATURE:
<223> OTHER INFORMATION: Synthetic amino acid sequence

<400> SEQUENCE: 66

Trp Glu Ala Ala Ala Arg Glu Ala Cys Cys Arg Glu Cys Cys Ala Arg
1               5                   10                  15

Ala

<210> SEQ ID NO 67
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 67

Thr Phe Phe Tyr Gly Gly Cys Arg Gly Lys Arg Asn Asn Phe Lys Thr
1               5                   10                  15
```

```
Glu Glu Tyr

<210> SEQ ID NO 68
<211> LENGTH: 19
<212> TYPE: PRT
<213> ORGANISM: Artificial sequence
<220> FEATURE:
<223> OTHER INFORMATION: Synthetic amino acid sequence

<400> SEQUENCE: 68

Thr Phe Phe Tyr Gly Gly Ser Arg Gly Lys Arg Asn Asn Phe Lys Thr
1               5                   10                  15

Glu Glu Tyr

<210> SEQ ID NO 69
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 69

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 70
<211> LENGTH: 20
<212> TYPE: PRT
<213> ORGANISM: Artificial sequence
<220> FEATURE:
<223> OTHER INFORMATION: Synthetic amino acid sequence

<400> SEQUENCE: 70

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 71
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 71

Thr Phe Val Tyr Gly Gly Cys Arg Ala Lys Arg Asn Asn Phe Lys Ser
1               5                   10                  15
```

METHODS OF TREATING A TAUOPATHY

CROSS-REFERENCE

This application claims the benefit of U.S. Provisional Patent Application No. 61/754,085, filed Jan. 18, 2013, and 61/781,823, filed Mar. 14, 2013, which applications are incorporated herein by reference in their entirety.

INCORPORATION BY REFERENCE OF SEQUENCE LISTING PROVIDED AS A TEXT FILE

A Sequence Listing is provided herewith as a text file, "IPRN-745 SeqList_ST25.txt" created on May 1, 2014 and having a size of 64 KB. The contents of the text file are incorporated by reference herein in their entirety.

INTRODUCTION

The microtubule associated protein tau is abundant in the central nervous system and is produced primarily by neurons. The primary function of tau is to stabilize microtubules. Six tau isoforms exist in the adult human brain; tau isoforms are the products of alternative splicing of a single gene.

Tauopathies are a class of neurodegenerative diseases resulting from the pathological aggregation of tau protein in so-called neurofibrillary tangles (NFT) in the brain. Some examples of tauopathies include frontotemporal dementia (FTD), Alzheimer's disease, progressive supranuclear palsy, corticobasal degeneration, and frontotemporal lobar degeneration.

There is a need in the art for methods of treating tauopathies, and for reagents suitable for use in such methods.

SUMMARY

The present disclosure provides methods of treating a tauopathy, involving administering an anti-Tau antibody. The present disclosure also provides anti-Tau antibodies, and formulations comprising same, for use in the methods.

Features

The present disclosure provides a method of treating a tauopathy in an individual. In some cases, the method comprises administering to the individual a pharmaceutical composition comprising: a) an antibody that specifically binds an epitope within a human Tau polypeptide, wherein the antibody comprises: i) light chain complementarity-determining regions (CDRs) of an IPN001 antibody depicted in FIG. 1B; and heavy chain CDRs of an IPN001 antibody depicted in FIG. 1A; or ii) light chain CDRs of an IPN002 antibody depicted in FIG. 2B; and heavy chain CDRs of an IPN002 antibody depicted in FIG. 2A; and b) a pharmaceutically acceptable excipient suitable for administration to a human.

The present disclosure provides a method of treating a tauopathy in an individual. In some cases, the method comprises administering to the individual a pharmaceutical composition comprising: a) an antibody that specifically binds an epitope within a human Tau polypeptide, wherein the antibody competes for binding to the epitope with an antibody that comprises: i) light chain complementarity-determining regions (CDRs) of an IPN001 antibody depicted in FIG. 1B; and heavy chain CDRs of an IPN001 antibody depicted in FIG. 1A; or ii) light chain CDRs of an IPN002 antibody depicted in FIG. 2B; and heavy chain CDRs of an IPN002 antibody depicted in FIG. 2A; and b) a pharmaceutically acceptable excipient suitable for administration to a human.

In some aspects of a subject method for treating a tauopathy, the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12.

In some aspects of a subject method for treating a tauopathy, the antibody comprises a humanized light chain framework region. In other aspects of a subject method for treating a tauopathy, the antibody comprises a humanized heavy chain framework region.

In some aspects of a subject method for treating a tauopathy, the antibody is encapsulated in a liposome. In some aspects of a subject method for treating a tauopathy, the antibody is formulated with an agent that facilitates crossing the blood-brain barrier. In some aspects of a subject method for treating a tauopathy, the antibody is fused, directly or via a linker, to a carrier molecule, a peptide or a protein that promotes the crossing of the blood-brain barrier. In some aspects of a subject method for treating a tauopathy, the antibody is a Fv, scFv, Fab, F(ab')2, or Fab'.

In some aspects of a subject method for treating a tauopathy, the administering step results in reduction in one or more of: a) the amount of free extracellular tau in brain tissue; b) the neuron-to-neuron spread of tau; c) the amount of intraneuron tau aggregates; d) the degree of microglial and/or astrocyte activation; e) the amount of phosphorylated or hyperphosphorylated tau; f) the amount of total Tau; g) the amount of intracellular N-terminal tau fragments; and h) neuronal hyperactivity.

In some aspects of a subject method for treating a tauopathy, the method further comprises administering at least one additional agent that treats the tauopathy.

In some aspects of a subject method for treating a tauopathy, the pharmaceutical composition is administered via intravenous administration, or via intrathecal administration.

The present disclosure provides a pharmaceutical formulation comprising: a) an antibody that specifically binds an epitope within an N-terminal portion of Tau, wherein the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12; and b) a pharmaceutically acceptable excipient suitable for administration to a human.

In some aspects of a subject pharmaceutical formulation, the antibody comprises a humanized light chain framework region. In other aspects of a subject pharmaceutical formulation, the antibody comprises a humanized heavy chain framework region.

In some aspects of a subject pharmaceutical formulation, the antibody is encapsulated in a liposome. In some aspects of a subject pharmaceutical formulation, the antibody is formulated with an agent that facilitates crossing the blood-brain barrier. In some aspects of a subject pharmaceutical formulation, the antibody is fused, directly or via a linker, to a carrier molecule, a peptide or a protein that promotes the crossing of the blood-brain barrier. In some aspects of a subject pharmaceutical formulation, the antibody is a Fv, scFv, Fab, F(ab')2, or Fab'.

The present disclosure provides a sterile container comprising a subject pharmaceutical formulation. In some cases, the container is a syringe.

The present disclosure provides an antibody that specifically binds an epitope within an N-terminal portion of Tau, where the antibody comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; and (iv) a humanized light chain framework region; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; (iii) a $V_H$ CDR3 comprising an amino acid sequence of SEQ ID NO:6 or SEQ ID NO:12; and iv) a humanized heavy chain framework region.

In some aspects of a subject antibody, the light chain region and the heavy chain region are present in separate polypeptides. In some aspects of a subject antibody, the light chain region and the heavy chain region are present in a single polypeptide. In some aspects of a subject antibody, the heavy chain region is of the isotype IgG1, IgG2, IgG3, or IgG4. In some aspects of a subject antibody, the antibody is a Fv, scFv, Fab, F(ab')2, or Fab'.

In some cases, the heavy chain region is of the isotype IgG4. In some of these embodiments, the hinge region comprises an S241P substitution. See, e.g., Angal et al. (1993) *Mol. Immunol.* 30:105.

In some aspects of a subject antibody, the antibody comprises a covalently linked non-peptide synthetic polymer, e.g., where the synthetic polymer is a poly(ethylene glycol) polymer. In some aspects of a subject antibody, the antibody is fused, directly or via a linker, to a carrier molecule, a peptide or a protein that promotes the crossing of the blood-brain barrier.

The present disclosure provides a recombinant expression vector comprising a nucleotide sequence encoding a subject antibody, where the nucleotide sequence is operably linked to a transcriptional control element that is active in a eukaryotic cell. The present disclosure provides an in vitro host cell genetically modified with the recombinant expression vector.

The present disclosure provides a method of monitoring progression of a tauopathy in an individual. The method can comprise: a) determining a first level of a Tau polypeptide in a biological sample obtained from the individual at a first time point; b) determining a second level of a Tau polypeptide in a biological sample obtained from the individual at a second time point; and c) comparing the second level of Tau with the first level of Tau, wherein said determining comprises: i) contacting the biological sample with a subject anti-Tau antibody; and ii) quantitating binding of the antibody to Tau polypeptide present in the sample.

In some aspects of a subject method of monitoring progression of a tauopathy, the biological sample is cerebrospinal fluid, blood, plasma, serum, urine, or saliva. In some aspects of a subject method of monitoring progression of a tauopathy, the quantitated Tau polypeptide is total Tau polypeptide. In other aspects of a subject method of monitoring progression of a tauopathy, the quantitated Tau polypeptide is an N-terminal fragment of a full-length Tau polypeptide.

In some aspects of a subject method of monitoring progression of a tauopathy, the first time point is a time point before initiation of a treatment regimen, and wherein the second time point is a time point after initiation of a treatment regimen.

The present disclosure provides a method of detecting a Tau polypeptide in a living individual in vivo. The method can comprise: a) administering to the individual a subject anti-Tau antibody; and b) detecting binding of the antibody to tau polypeptide in a brain tissue in the individual using an imaging method. In some aspects of a subject method of detecting a Tau polypeptide in a living individual in vivo, the antibody comprises a contrast agent suitable for use in the imaging method. In some aspects of a subject method of detecting a Tau polypeptide in a living individual in vivo, the imaging method is magnetic resonance imaging or positron emission tomography.

The present disclosure provides an in vitro method of detecting a Tau polypeptide in a biological sample obtained from an individual. The method can comprise: a) contacting the biological sample with a subject anti-Tau antibody; and b) detecting binding of the antibody to Tau polypeptide present in the sample.

In some aspects of a subject in vitro method of detecting a Tau polypeptide in a biological sample obtained from an individual, the biological sample is blood, serum, plasma, urine, saliva, or cerebrospinal fluid. In some aspects of a subject in vitro method of detecting a Tau polypeptide in a biological sample obtained from an individual, the individual is suspected of having a tauopathy, has been diagnosed as having a tauopathy, or has a genetic predisposition to developing a tauopathy.

In some aspects of a subject in vitro method of detecting a Tau polypeptide in a biological sample obtained from an individual, the method is quantitative. In some aspects of a subject in vitro method of detecting a Tau polypeptide in a biological sample obtained from an individual, the Tau polypeptide detected is total Tau polypeptide. In other aspects of a subject in vitro method of detecting a Tau polypeptide in a biological sample obtained from an individual, the Tau polypeptide detected is an N-terminal fragment of a full-length Tau polypeptide.

BRIEF DESCRIPTION OF THE DRAWINGS

FIGS. 1A and 1B provide amino acid sequences of IPN001 VH (FIG. 1A) and VL (FIG. 1B). Complementarity-determining regions (CDRs) are in bold text and underlined.

FIGS. 2A and 2B provide amino acid sequences of IPN002 VH (FIG. 2A) and VL (FIG. 2B). Complementarity-determining regions (CDRs) are in bold text and underlined.

FIGS. 6A-D provide amino acid sequences of full-length human Tau (from top to bottom SEQ ID NOs:21-27).

FIG. 9 depicts an amino acid sequence of humanized IPN002 VH variant 1; and a nucleotide sequence encoding the amino acid sequence (SEQ ID NOs:28-36).

FIG. 10 depicts an amino acid sequence of humanized IPN002 VH variant 2; and a nucleotide sequence encoding the amino acid sequence (SEQ ID NOs:29-37).

FIG. 11 depicts an amino acid sequence of humanized IPN002 VH variant 3; and a nucleotide sequence encoding the amino acid sequence (SEQ ID NOs:30-38).

FIG. 12 depicts an amino acid sequence of humanized IPN002 VH variant 4; and a nucleotide sequence encoding the amino acid sequence (SEQ ID NOs:31-39).

FIG. 13 depicts an amino acid sequence of humanized IPN002 Vκ variant 1; and a nucleotide sequence encoding the amino acid sequence (SEQ ID NOs:32-40).

FIG. 14 depicts an amino acid sequence of humanized IPN002 Vκ variant 2; and a nucleotide sequence encoding the amino acid sequence (SEQ ID NOs:33-41).

FIG. 15 depicts an amino acid sequence of humanized IPN002 Vκ variant 3; and a nucleotide sequence encoding the amino acid sequence (SEQ ID NOs:34-42).

FIG. 16 depicts an amino acid sequence of humanized IPN002 Vκ variant 4; and a nucleotide sequence encoding the amino acid sequence (SEQ ID NOs:35-43).

FIG. 17 provides Table 4, which shows binding properties of humanized IPN-002 variants to eTau proteins.

FIG. 18 provides Table 5, which shows binding properties of humanized IPN-002 variants to Tau-383.

FIGS. 19A and 19B depict properties of humanized IPN002 variants. FIG. 19A depicts binding of humanized IPN-002 variants to tau present in iPSC-CN conditioned media; iPSC-CN lysates; AD brain lysates; and P301L tau mouse brain cortex lysates; and cynomologus monkey brain lysates. FIG. 19B depicts inhibition of eTau-induced neuronal hyperactivity by humanized IPN002 variants.

FIG. 20 depicts amino acid sequences of eTau fragments, in alignment with a fetal tau amino acid sequence (from top to bottom SEQ ID NOs:27, 44-48).

FIG. 23 depicts reduction in free tau levels and in total tau levels in interstitial fluid (ISF) following treatment with IPN002.

FIG. 24 depicts reduction in free tau levels in cerebrospinal fluid (CSF) following treatment with IPN002.

FIG. 25 depicts reduction of eTau-induced neuronal hyperactivity by IPN002.

FIG. 26 depicts the presence of Tau fragments in CSF from individuals with likely chronic traumatic encephalopathy.

DEFINITIONS

Figure 3:
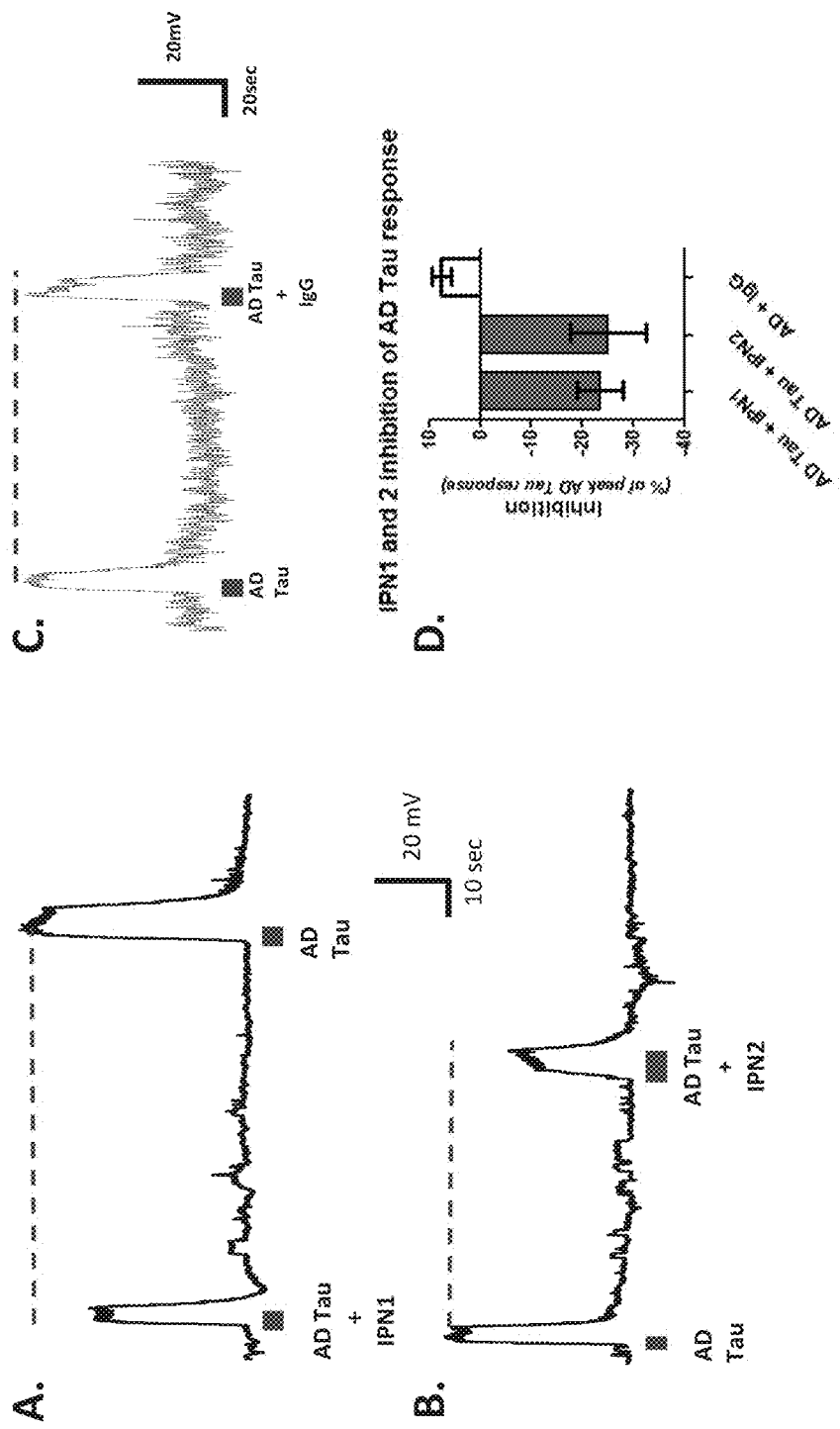
FIGS. 3A-D depicts the effect of anti-Tau antibody IPN002 on Tau-mediated membrane depolarization in cortical neurons.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, bi-specific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of non-human origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476, 786; and Bird, R. E. et al., Science, 242: 423-426 (1988)), regarding single chain antibodies.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies, vol. 113, Rosenburg and Moore eds.*, Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

As used herein, the term "affinity" refers to the equilibrium constant for the reversible binding of two agents (e.g., an antibody and an antigen) and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A subject anti-Tau antibody binds specifically to an epitope within a Tau polypeptide. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs have been described by Kabat et al., J. Bio. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] (seq. list)[2] | Chothia[3] | MacCallum[4] |
|---|---|---|---|
| $V_H$ CDR1 | 31-35 (31-35) | 26-32 | 30-35 |
| $V_H$ CDR2 | 50-65 (50-66) | 53-55 | 47-58 |
| $V_H$ CDR3 | 95-102 (99-106) | 96-101 | 93-101 |
| $V_L$ CDR1 | 24-34 (24-39) | 26-32 | 30-36 |
| $V_L$ CDR2 | 50-56 (55-61) | 50-52 | 46-55 |
| $V_L$ CDR3 | 89-97 (94-102) | 91-96 | 89-96 |

[1]Residue numbering follows the nomenclature of Kabat et al., supra
[2]Corresponding residues according to the numbering provided in the Sequence Listing
[3]Residue numbering follows the nomenclature of Chothia et al., supra
[4]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of an anti-Tau antibody that, when administered to a mammal or other subject for treating a disease, is sufficient to effect such treatment for the disease. The "therapeutically effective amount" will vary depending on the anti-Tau antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, blood fractions such as plasma and serum, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a humanized anti-Tau antibody" includes a plurality of such antibodies and reference to "the tauopathy" includes reference to one or more tauopathies and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of treating a tauopathy, involving administering an anti-Tau antibody. The present disclosure also provides anti-Tau antibodies, and formulations comprising same, for use in the methods. The present disclosure further provides in vitro and in vivo detection methods using an anti-Tau antibody described herein.

Methods of Treating a Tauopathy

The present disclosure provides methods of treating a tauopathy. The methods generally involve administering an effective amount of an anti-Tau antibody of the present disclosure to an individual in need thereof. In some cases, administration of a subject anti-tau antibody reduces the level of a pathological tau polypeptide in a cell, a tissue, or a fluid of an individual, and treats the tauopathy.

As described in more detail below, an anti-Tau antibody of the present disclosure specifically binds Tau, where the epitope bound by the antibody is a linear epitope, and comprises amino acid residues within an amino-terminal (N-terminal) portion of Tau, e.g., within amino acids 1-25 of Tau, within amino acids 1-18 of Tau, or within amino acids 9 to 18 of Tau. Amino acid sequences of human Tau isoforms are depicted in FIGS. 6A-D. Amino acids 1-18 of Tau are: MAEPRQEFEVMEDHAGTY; SEQ ID NO:49). See, e.g., Garcia-Sierra et al. (2003) J. Alzheimer's Disease 5:65; and Horowitz et al. (2004) J. Neurosci. 24:7895.

In some cases, a method of the present disclosure for treating a tauopathy comprises administering to an individual in need thereof a pharmaceutical composition comprising: a) an anti-Tau antibody comprising: i) one, two, or three light chain complementarity-determining regions (CDRs) of an IPN001 antibody depicted in FIG. 1; and one, two, or three heavy chain CDRs of an IPN001 antibody depicted in FIG. 1; or ii) one, two, or three light chain CDRs of an IPN002 antibody depicted in FIG. 2; and one, two, or three heavy chain CDRs of an IPN002 antibody depicted in FIG. 2; and b) a pharmaceutically acceptable excipient suitable for administration to a human.

In some cases, a method of the present disclosure for treating a tauopathy comprises administering to an individual in need thereof a pharmaceutical composition comprising: a) an antibody that specifically binds an epitope within a human Tau polypeptide, where the antibody competes for binding to the epitope with an antibody that comprises: i) light chain complementarity-determining regions (CDRs) of an IPN001 antibody depicted in FIG. 1B; and heavy chain CDRs of an IPN001 antibody depicted in FIG. 1A; or ii) light chain CDRs of an IPN002 antibody depicted in FIG. 2B; and heavy chain CDRs of an IPN002 antibody depicted in FIG. 2A; and b) a pharmaceutically acceptable excipient suitable for administration to a human.

In some cases, a method of the present disclosure for treating a tauopathy comprises administering to an individual in need thereof a pharmaceutical composition comprising: a) an antibody that competes for binding with IPN001 to an epitope in Tau that is recognized by IPN001 (e.g., a linear epitope within an N-terminal portion of Tau, e.g., within amino acids 1-25 of Tau, within amino acids 1-18 of Tau, or within amino acids 9 to 18 of Tau); and b) a pharmaceutically acceptable excipient suitable for administration to a human. In other instances, a method of the present disclosure for treating a tauopathy comprises administering to an individual in need thereof a pharmaceutical composition comprising: a) an antibody that competes for binding with IPN002 to an epitope in Tau that is recognized by IPN002 (e.g., a linear epitope within an N-terminal portion of Tau, e.g., within amino acids 1-25 of Tau, within amino acids 1-18 of Tau, or within amino acids 9 to 18 of Tau); and b) a pharmaceutically acceptable excipient suitable for administration to a human.

IPN001 (also referred to herein as "IPN1" or "IPN-1") and IPN002 (also referred to herein as "IPN2" or "IPN-2") specifically bind Tau. The epitope bound by IPN001 is a linear epitope, and comprises amino acid residues within an amino-terminal (N-terminal) portion of Tau, e.g., within amino acids 1-25 of Tau, within amino acids 1-18 of Tau, or within amino acids 9 to 18 of Tau. The epitope bound by IPN002 is a linear epitope, and comprises amino acid residues within an amino-terminal (N-terminal) portion of Tau, e.g., within amino acids 1-25 of Tau, within amino acids 1-18 of Tau, or within amino acids 9 to 18 of Tau. Amino acid sequences of human Tau isoforms are depicted in FIGS. 6A-D. Amino acids 1-18 of Tau are: MAEPRQEFEVMEDHAGTY; SEQ ID NO:49). See, e.g., Garcia-Sierra et al. (2003) J. Alzheimer's Disease 5:65; and Horowitz et al. (2004) J. Neurosci. 24:7895.

In some instances, an anti-Tau antibody of the present disclosure that is suitable for use in a method of treating a tauopathy comprises: a) a light chain variable region comprising: i) one, two, or three $V_L$ CDRs of an IPN001 antibody; and ii) a humanized light chain framework region; and b) a heavy chain variable region comprising: i) one, two, or three $V_H$ CDRs of an IPN001 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)).

In some instances, an anti-Tau antibody of the present disclosure that is suitable for use in a method of treating a tauopathy comprises: a) a light chain region comprising: i) one, two, or three $V_L$ CDRs of an IPN001 antibody; and ii) a humanized light chain framework region; and b) a heavy chain region comprising: i) one, two, or three $V_H$ CDRs of an IPN001 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In other instances, an anti-Tau antibody of the present disclosure that is suitable for use in a method of treating a tauopathy comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)).

In other instances, an anti-Tau antibody of the present disclosure (e.g., a subject antibody that specifically binds an epitope in a Tau polypeptide, where the epitope is within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In some cases, a method of the present disclosure for treating a tauopathy comprises administering to an individual in need thereof an effective amount of a pharmaceutical composition comprising: a) an antibody that specifically binds a linear epitope within an amino-terminal (N-terminal) portion of Tau, e.g., within amino acids 1-25 of Tau, within amino acids 1-18 of Tau, or within amino acids 9 to 18 of Tau (where amino acids 1-18 of Tau are: MAEPRQEFEVMEDHAGTY (SEQ ID NO:49)), where the antibody comprises: (i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; (iv) a $V_H$ CDR1 comprising an amino acid sequence of SEQ ID NO:4 or SEQ ID NO:10; (v) a $V_H$ CDR2 comprising an amino acid sequence of SEQ ID NO:5 or SEQ ID NO:11; and (vi) a $V_H$ CDR3 comprising an amino acid sequence of SEQ ID NO:6 or SEQ ID NO:12; and b) a pharmaceutically acceptable excipient suitable for administration to a human.

$V_H$ and $V_L$ amino acid sequences of IPN001 are depicted in FIGS. 1A and 1B. CDRs (as defined by Kabat) are in bold text and underlined. $V_H$ and $V_L$ amino acid sequences of IPN002 are depicted in FIGS. 2A and 2B. CDRs (as defined by Kabat) are in bold text and underlined.

SEQ ID NOs:1-12 are as follows:

| | |
|---|---|
| RSSQTILHSNGNTYLE; | (SEQ ID NO: 1) |
| KVSKRFS; | (SEQ ID NO: 2) |
| FQGSLVPWA; | (SEQ ID NO: 3) |
| SYGMS; | (SEQ ID NO: 4) |
| TISSSGSRTYFPDSVKG; | (SEQ ID NO: 5) |
| TWDGAMDY; | (SEQ ID NO: 6) |
| KSSQSIVHSNGNTYLE; | (SEQ ID NO: 7) |
| KVSNRFS; | (SEQ ID NO: 8) |
| FQGSLVPWA; | (SEQ ID NO: 9) |
| KYGMS; | (SEQ ID NO: 10) |
| TISSSGSRTYYPDSVKG; | (SEQ ID NO: 11) |
| SWDGAMDY. | (SEQ ID NO: 12) |

In some cases, the antibody comprises a humanized light chain framework region and/or a humanized heavy chain framework region. Humanized anti-Tau antibodies are described in detail below.

A tauopathy is a disorder characterized by an abnormal level of tau in a cell, a tissue, or a fluid in an individual. In some cases, a tauopathy is characterized by the presence in a cell, a tissue, or a fluid of elevated (higher than normal) levels of tau or tau polypeptides and/or pathological forms of tau. For example, in some cases, a tauopathy is characterized by the presence in brain tissue and/or cerebrospinal fluid of elevated levels of tau or tau polypeptides and/or pathological forms of tau. A "higher than normal" level of tau in a cell, a tissue, or a fluid indicates that the level of tau in the tissue or fluid is higher than a normal, control level, e.g., higher than a normal, control level for an individual or population of individuals of the same age group. See, e.g., Blomberg et al. (2001) "Cerebrospinal fluid tau levels increase with age in healthy individuals" Dement. Geriatr. Cogn. Disord. 12:127. In some cases, an individual having a tauopathy exhibits one or more additional symptoms of a tauopathy (e.g., cognitive decline).

In other cases, a tauopathy is characterized by the presence in a cell, a tissue, or a fluid of lower than normal levels of tau. A "lower than normal" level of tau in a tissue or a fluid indicates that the level of tau in the cell, tissue, or fluid is lower than a normal, control level, e.g., lower than a normal, control level for an individual or population of individuals of the same age group.

Alzheimer's disease and certain forms of Frontotemporal dementia (Pick's disease, sporadic Frontotemporal dementia and Frontotemporal dementia with Parkinsonism linked to chromosome 17) are the most common forms of tauopathy. The present disclosure provides a treatment method as described above, wherein the tauopathy is Alzheimer's, Pick's disease, sporadic Frontotemporal dementia and Frontotemporal dementia with Parkinsonism linked to chromosome 17. Other tauopathies include, but are not limited to, Progressive supranuclear palsy (PSP), Corticobasal degeneration (CBD) and Subacute sclerosing panencephalitis.

A neurodegenerative tauopathy includes Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia (FTD), frontotemporal dementia with parkinsonism linked to chromosome 17, frontotemporal lobar degeneration, Gerstmann-Straussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, Tangle only dementia, multi-infarct dementia, ischemic stroke, chronic traumatic encephalopathy (CTE), traumatic brain injury (TBI), and stroke.

The present disclosure also provides methods of treating a synucleinopathy, e.g., Parkinson's disease (PD); dementia with Lewy Bodies (DLB); multiple system atrophy (MSA); etc. For example, PD with dementia (PDD) can be treated with a subject method.

In one embodiment, an anti-tau antibody of the present disclosure prevents or delays the onset of at least one symptom of a neurodegenerative tauopathy in a subject. In one embodiment, a subject anti-tau antibody reduces or eliminates at least one symptom of a neurodegenerative tauopathy in a subject. The symptom may be the formation of one or more of pathological tau deposits; extracellular soluble Tau and/or Tau fragments; hyperphosphorylated tau deposits; insoluble tau deposits; neurofibrillary tangles; neurofibrillary fibers; pre-tangle phospho-tau aggregates; intraneuronal neurofibrillary tangles; neuronal hyperactivity; and extraneuronal neurofibrillary tangles in the brain or spinal cord of a subject. The symptom may be a neurological symptom, for example, impaired cognitive function, memory impairment, loss of motor function, etc.

The symptom can also be the level of a Tau polypeptide in the CSF of the individual. For example, in some embodiments, a subject anti-tau antibody, when administered in one or more doses as monotherapy or in combination therapy to an individual having a tauopathy, reduces the level of a Tau polypeptide in the CSF of the individual by at least about 10%, at least about 15%, at least about 20%, at least about 25%, at least about 30%, at least about 40%, at least about 50%, or more than 50%, compared to the level of the Tau polypeptide in the CSF of the individual before treatment with the anti-tau antibody.

Administration of a subject anti-tau antibody to an individual can result in one or more of: reduction in the amount of free extracellular Tau in brain tissue; reduction in the cell-to-cell spread (e.g., neuron-to-neuron spread) of Tau (e.g., Tau fragments); reduction in the amount of tau aggregates (e.g., intracellular (e.g., intraneuronal) tau aggregates); reduction in the amount of neurofibrillary tangles in brain tissue; reduction in the level of microglial activation and/or astrocyte activation; reduction in the amount of phosphorylated tau; reduction in the amount of hyperphosphorylated tau; reduction in total Tau (e.g., total intracellular Tau; and/or total extracellular Tau); reduction in neuronal hyperactivity; and reduction in the amount of N-terminal Tau fragments. "Total Tau" can include the sum total of full-length Tau of any isoform; and any N-terminal Tau fragments that are present and that display the epitope recognized by a subject anti-Tau antibody. Amino acid sequences of human full-length Tau are presented in FIGS. 6A-D.

Administration of a subject anti-tau antibody to an individual can in some cases improve cognitive function in the individual, or at least reduce the rate of decline of cognitive function in the individual.

In some cases, administration of a subject anti-tau antibody to an individual reduces the amount of free extracellular tau polypeptide (e.g., the amount of free extracellular tau polypeptide in a brain tissue) by at least about 10%, at least about 20%, at least about 25%, at least about 50%, or more than 50%, compared to the amount of free extracellular tau polypeptide in the individual before administration with the anti-tau antibody.

In some cases, administration of a subject anti-tau antibody to an individual reduces the cell-to-cell (e.g., neuron-to-neuron) spread of a tau polypeptide (e.g., a pathological tau polypeptide) by at least about 10%, at least about 20%, at least about 25%, at least about 50%, or more than 50%, compared to the cell-to-cell spread before administration with a subject anti-tau antibody.

In some cases, administration of a subject anti-tau antibody to an individual reduces the amount of tau aggregates (e.g., intracellular (e.g., intraneuronal) tau aggregates) by at least about 10%, at least about 20%, at least about 25%, at least about 50%, or more than 50%, compared to the amount of tau aggregates before administration with the anti-tau antibody.

In some cases, administration of a subject anti-tau antibody to an individual reduces neurotoxicity in an individual; and/or reduces neuroinflammation in an individual; and/or reduces activation of astrocytes and microglia; and/or reduces induction of pathological electrophysiological effects; and/or reduces the amount of tau in exosomes.

In some cases, administration of a subject anti-tau antibody to an individual reduces neuronal hyperactivity by at least about 10%, at least about 20%, at least about 25%, at least about 50%, or more than 50%, compared to the level of degree of neuronal hyperactivity before administration with the anti-tau antibody.

Administration of the suitable compositions may be effected by different ways, e.g., by intravenous, intraperitoneal, subcutaneous, intracranial, intrathecal, intraarterial (e.g., via the carotid artery), intramuscular, intranasal, topical or intradermal administration or spinal or brain delivery. Aerosol formulations such as nasal spray formulations include purified aqueous or other solutions of the active agent with preservative agents and isotonic agents. Such formulations are adjusted to a pH and isotonic state compatible with the nasal mucous membranes.

In some cases, a subject anti-tau antibody is modified, or formulated, in such a manner as to provide the ability of the antibody to cross the blood-brain barrier. Such an antibody or antibody composition can be administered to an individual having a tauopathy by various enteral and parenteral routes of administration including oral, intravenous, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition of the present disclosure may comprise further agents such as dopamine or psychopharmacologic drugs, depending on the intended use of the pharmaceutical composition.

The dosage regimen will be determined by the attending physician or other medical personnel, based on various clinical factors. As is well known in the medical arts, dosages for any one patient depends upon various factors, including the patient's size, body surface area, age, the particular compound to be administered, sex, time and route of administration, general health, and other drugs being administered concurrently. A dose of a subject anti-tau antibody can be, for example, in the range of 0.001 µg to 1000 µg; however, doses below or above this exemplary range are envisioned, especially considering the aforementioned factors. Generally, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment.

Combination Therapy

An anti-tau antibody of the present disclosure can be administered to an individual in need thereof alone (e.g., as monotherapy); or in combination therapy with one or more additional therapeutic agents.

For the treatment of AD, suitable additional therapeutic agents include, but are not limited to, acetylcholinesterase inhibitors, including, but not limited to, Aricept (donepezil), Exelon (rivastigmine), metrifonate, and tacrine (Cognex); an anti-Aβ antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art.

Another suitable additional therapeutic agent in the treatment of AD is an agent that inhibits tau aggregation, e.g., a napthoquinone derivative that inhibits tau aggregation, as described in U.S. Pat. No. 7,605,179. Another suitable additional therapeutic agent is an agent that inhibits phosphorylation of tau, e.g., a 3-substituted-4-pyrimidone derivative that inhibits tau protein kinase 1, as described in U.S. Pat. No. 7,572,793.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Individuals to be Treated

Individuals suitable for treatment with a subject anti-tau antibody include individuals who have been diagnosed as having a tauopathy; individuals at greater risk than the general population for developing a tauopathy (e.g., individuals having a genetic predisposition to developing a tauopathy); individuals with PDD; and the like. In some cases, the individual is an adult human. In some cases, the adult human is 30 years of age or older; 40 years of age or older, 50 years of age or older, 60 years of age or older, 70 years of age or older, or 80 years of age or older. For example, the adult human can be from 40 years old to 50 years old, from 50 years old to 60 years old, from 60 years old to 70 years old, or older than 70 years.

Anti-Tau Antibodies

The present disclosure provides anti-Tau antibodies, and pharmaceutical formulations comprising same.

The present disclosure provides an isolated antibody that specifically binds an epitope within an epitope in a Tau polypeptide (e.g., a linear epitope within an amino-terminal (N-terminal) portion of Tau, e.g., within amino acids 1-25 of Tau, within amino acids 1-18 of Tau, or within amino acids 9 to 18 of Tau). In some instances, the antibody is humanized, e.g., one or more framework regions of the heavy chain variable region and/or the light chain variable region includes sequences derived from a human immunoglobulin framework.

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIACORE) and/or solid-phase enzyme-linked immunosorbent assay (ELISA) analysis. In many cases, a subject humanized anti-Tau antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, e.g., those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

CDR and framework regions are as defined by Kabat, Sequences of Proteins of Immunological Interest (National Institutes of Health, Bethesda, Md., 1987 and 1991). An alternative structural definition has been proposed by Chothia et al., J. Mol. Biol. 196:901 (1987); Nature 342:878 (1989); and J. Mol. Biol. 186:651 (1989) (collectively referred to as "Chothia"). When framework residues, as defined by Kabat, supra, constitute structural loop residues as defined by Chothia, supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196: 901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986)) and selecting these amino acids from the donor may be desirable to keep all the antigen contacts that provide affinity in the original antibody.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three complementarity determining regions (CDRs) of an IPN001 antibody, where the CDRs are as defined by Kabat (see, e.g., Table 1, above; and Kabat et al., U.S. Dept. of Health and Human Services, "Sequences of proteins of immunological interest" (1991)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three $V_L$ CDRs of an IPN001 antibody; and ii) a humanized light chain framework region; and b) a heavy chain region comprising: i) one, two, or three $V_H$ CDRs of an IPN001 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)). In some of these embodiments, the anti-Tau antibody includes a humanized $V_H$ and/or $V_L$ framework region.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three $V_L$ CDRs of an IPN001 antibody; and ii) a humanized light chain framework region; and b) a heavy chain region comprising: i) one, two, or three $V_H$ CDRs of an IPN001 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Kabat (see, e.g., Table 1, above; and Kabat et al., U.S. Dept. of Health and Human Services, "Sequences of proteins of immunological interest" (1991)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three $V_L$ CDRs of an IPN002 antibody; and ii) a humanized light chain framework region; and b) a heavy chain region comprising: i) one, two, or three $V_H$ CDRs of an IPN002 antibody; and ii) a humanized heavy chain framework region; where the $V_H$ and $V_L$ CDRs are as defined by Chothia (see, e.g., Table 1, above; and Chothia et al., J. Mol. Biol. 196:901-917 (1987)).

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three CDRs selected from SEQ ID NO:1, SEQ ID NO:2, and SEQ ID NO:3; and ii) a humanized light chain framework region; and b) a heavy chain region comprising: i) one, two, or three CDRs selected from SEQ ID NO:4, SEQ ID NO:5, and SEQ ID NO:6; and ii) a humanized heavy chain framework region.

In some embodiments, an anti-Tau antibody of the present disclosure (e.g., a subject antibody that specifically binds an epitope in a Tau polypeptide, e.g., a linear epitope within an amino-terminal (N-terminal) portion of Tau, e.g., within amino acids 1-25 of Tau, within amino acids 1-18 of Tau, or within amino acids 9 to 18 of Tau) comprises: a) a light chain region comprising: i) one, two, or three CDRs selected from SEQ ID NO:7, SEQ ID NO:8, and SEQ ID NO:9; and ii) a humanized light chain framework region; and b) a heavy chain region comprising: i) one, two, or three CDRs selected from SEQ ID NO:10, SEQ ID NO:11, and SEQ ID NO:12; and ii) a humanized heavy chain framework region.

In some instances, the antibody comprises: a) a light chain region comprising: i) a $V_L$ CDR1 comprising an amino acid sequence of SEQ ID NO:1 or SEQ ID NO:7; (ii) a $V_L$ CDR2 comprising an amino acid sequence of SEQ ID NO:2 or SEQ ID NO:8; (iii) a $V_L$ CDR3 comprising an amino acid sequence of SEQ ID NO:3 or SEQ ID NO:9; and (iv) a humanized light chain framework region; and b) a heavy chain region comprising: (i) a $V_H$ CDR1 comprising an amino acid sequence of SEQ ID NO:4 or SEQ ID NO:10; (ii) a $V_H$ CDR2 comprising an amino acid sequence of SEQ ID NO:5 or SEQ ID NO:11; (iii) a $V_H$ CDR3 comprising an amino acid sequence of SEQ ID NO:6 or SEQ ID NO:12; and iv) a humanized heavy chain framework region.

In some embodiments, a subject anti-Tau antibody comprises a heavy chain variable region comprising one, two, or three of the heavy chain CDRs having an amino acid sequence selected from one or more of SEQ ID NOs:4, 5, and 6; and one, two, three, or four FR regions that are humanized. For example, in some embodiments, a subject antibody comprises a heavy chain variable region that comprises, in order from N-terminus to C-terminus: a humanized heavy chain FR1; a CDR1 comprising the amino acid sequence set forth in SEQ ID NO:4; a humanized heavy chain FR2; a CDR2 comprising the amino acid sequence set forth in SEQ ID NO:5; a humanized heavy chain FR3; a CDR3 comprising the amino acid sequence set forth in SEQ ID NO:6; and a humanized heavy chain FR4.

In some embodiments, a subject anti-Tau antibody comprises a light chain variable region comprising one, two, or three of the light chain CDRs having a polypeptide sequence selected from one or more of SEQ ID NOs:1, 2, and 3; and one, two, three, or four FR regions that are humanized. For example, in some embodiments, a subject antibody comprises a light chain variable region that comprises, in order from N-terminus to C-terminus: a humanized light chain FR1; a CDR1 comprising the amino acid sequence set forth in SEQ ID NO:1; a humanized light chain FR2; a CDR2 comprising the amino acid sequence set forth in SEQ ID NO:2; a humanized light chain FR3; a CDR3 comprising the amino acid sequence set forth in SEQ ID NO:3; and a humanized light chain FR4.

In some embodiments, a subject anti-Tau antibody comprises a heavy chain variable region comprising one, two, or three of the heavy chain CDRs having an amino acid sequence selected from one or more of SEQ ID NOs:10, 11, and 12; and one, two, three, or four FR regions that are humanized. For example, in some embodiments, a subject antibody comprises a heavy chain variable region that comprises, in order from N-terminus to C-terminus: a humanized heavy chain FR1; a CDR1 comprising the amino acid sequence set forth in SEQ ID NO:10; a humanized heavy chain FR2; a CDR2 comprising the amino acid sequence set forth in SEQ ID NO:11; a humanized heavy chain FR3; a CDR3 comprising the amino acid sequence set forth in SEQ ID NO:12; and a humanized heavy chain FR4.

In some embodiments, a subject anti-Tau antibody comprises a light chain variable region comprising one, two, or three of the light chain CDRs having a polypeptide sequence selected from one or more of SEQ ID NOs:7, 8, and 9; and one, two, three, or four FR regions that are humanized. For example, in some embodiments, a subject antibody comprises a light chain variable region that comprises, in order from N-terminus to C-terminus: a humanized light chain FR1; a CDR1 comprising the amino acid sequence set forth in SEQ ID NO:7; a humanized light chain FR2; a CDR2 comprising the amino acid sequence set forth in SEQ ID NO:8; a humanized light chain FR3; a CDR3 comprising the amino acid sequence set forth in SEQ ID NO:9; and a humanized light chain FR4.

$V_H$ and $V_L$ amino acid sequences of IPN001 are depicted in FIGS. 1A and 1B. CDRs (as defined by Kabat) are in bold text and underlined. $V_H$ and $V_L$ amino acid sequences of IPN002 are depicted in FIGS. 2A and 2B. CDRs (as defined by Kabat) are in bold text and underlined.

SEQ ID NOs:1-12 are as follows:

```
RSSQTILHSNGNTYLE;      (SEQ ID NO: 1)

KVSKRFS;               (SEQ ID NO: 2)

FQGSLVPWA;             (SEQ ID NO: 3)

SYGMS;                 (SEQ ID NO: 4)

TISSSGSRTYFPDSVKG;     (SEQ ID NO: 5)

TWDGAMDY;              (SEQ ID NO: 6)

KSSQSIVHSNGNTYLE;      (SEQ ID NO: 7)

KVSNRFS;               (SEQ ID NO: 8)

FQGSLVPWA;             (SEQ ID NO: 9)

KYGMS;                 (SEQ ID NO: 10)

TISSSGSRTYYPDSVKG;     (SEQ ID NO: 11)

SWDGAMDY.              (SEQ ID NO: 12)
```

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 1B and set forth in SEQ ID NO:13.

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 1A and set forth in SEQ ID NO:14.

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 2B and set forth in SEQ ID NO:15.

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 2A and set forth in SEQ ID NO:16.

Figure 9:
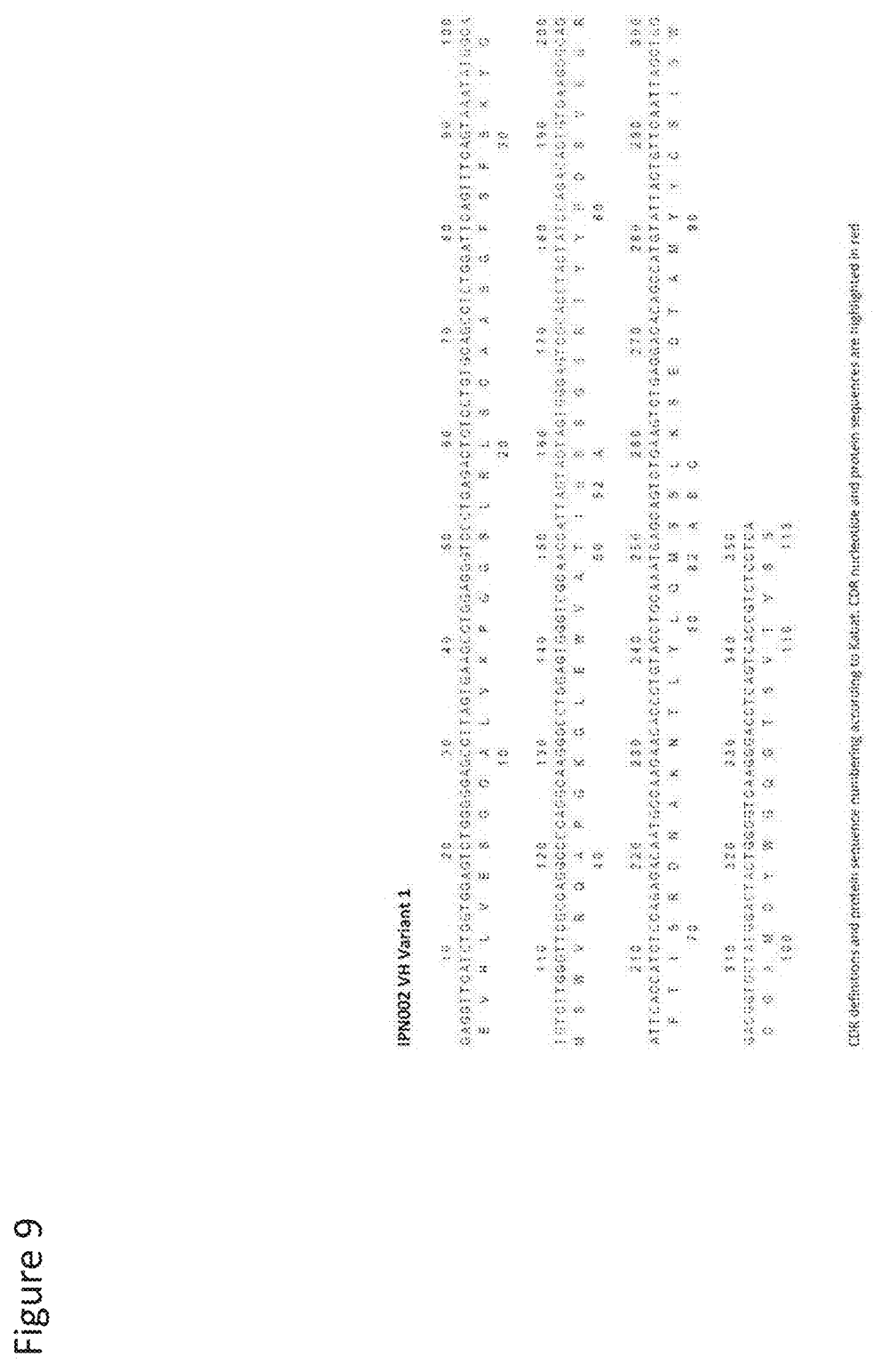

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 9 (VH variant 1).

Figure 10:
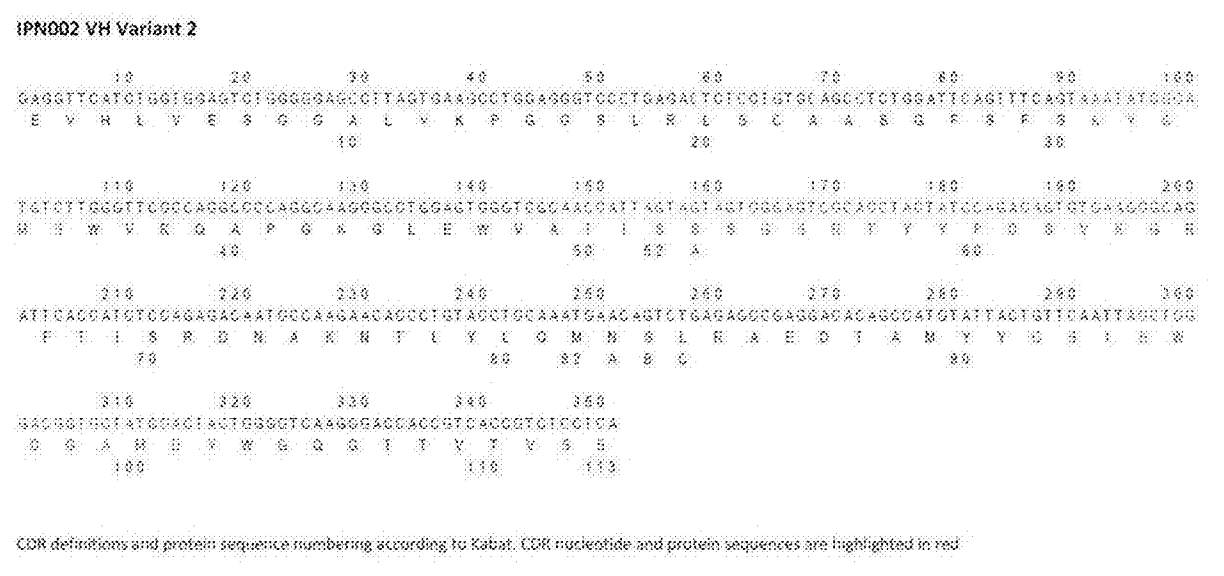

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 10 (VH variant 2).

Figure 11:
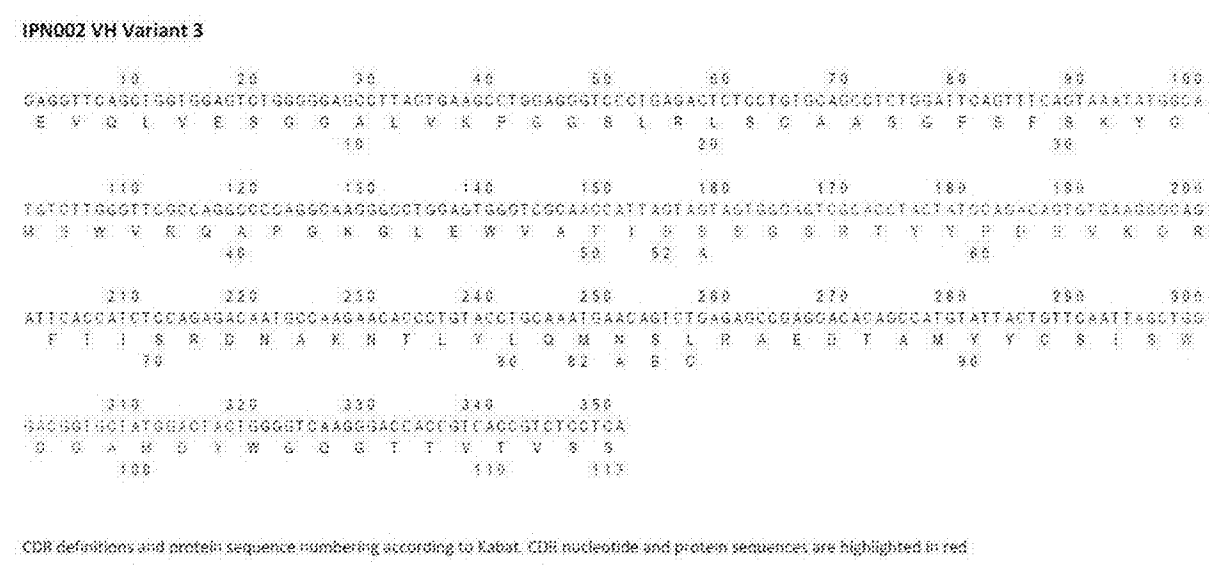

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 11 (VH variant 3).

Figure 12:
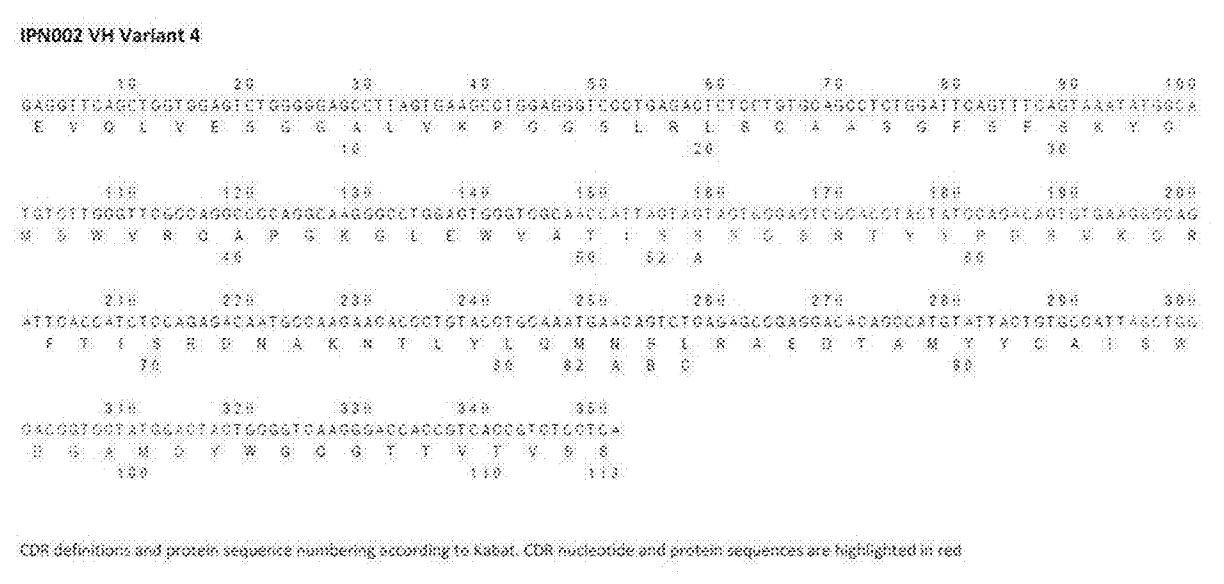

A subject anti-Tau antibody can comprise a heavy chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 12 (VH variant 4).

Figure 13:
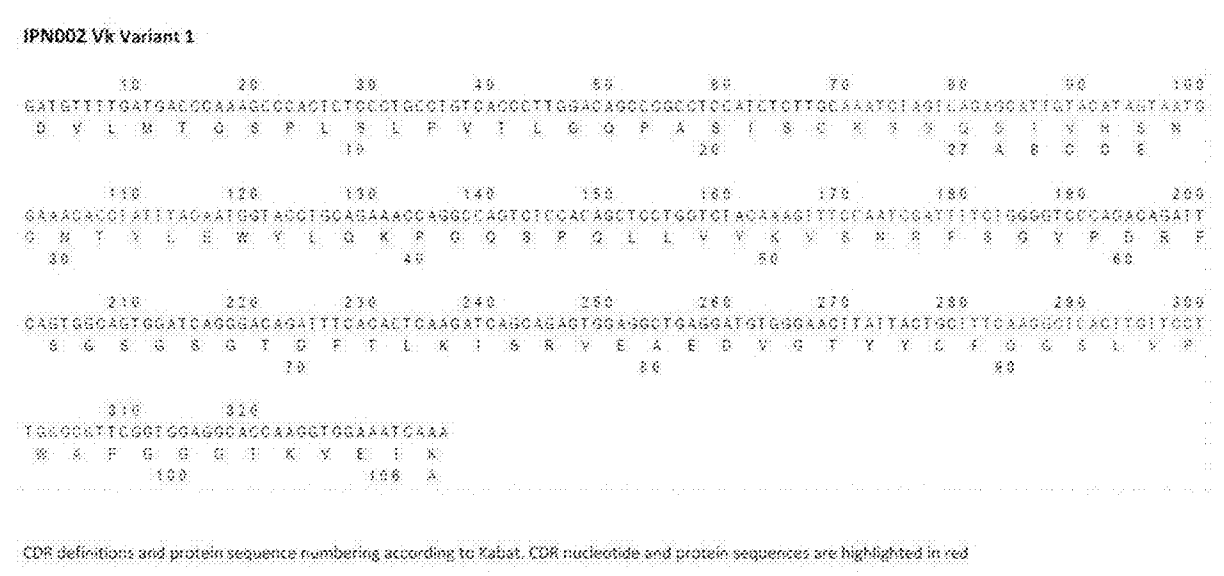

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 13 (Vk variant 1).

Figure 14:
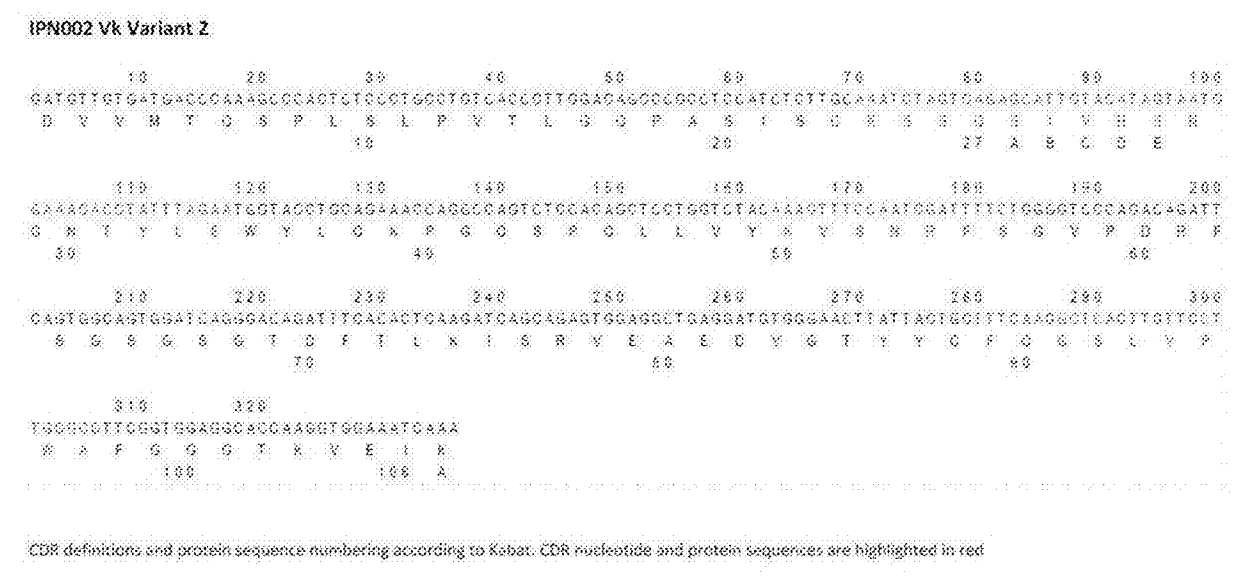

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 14 (Vk variant 2).

Figure 15:
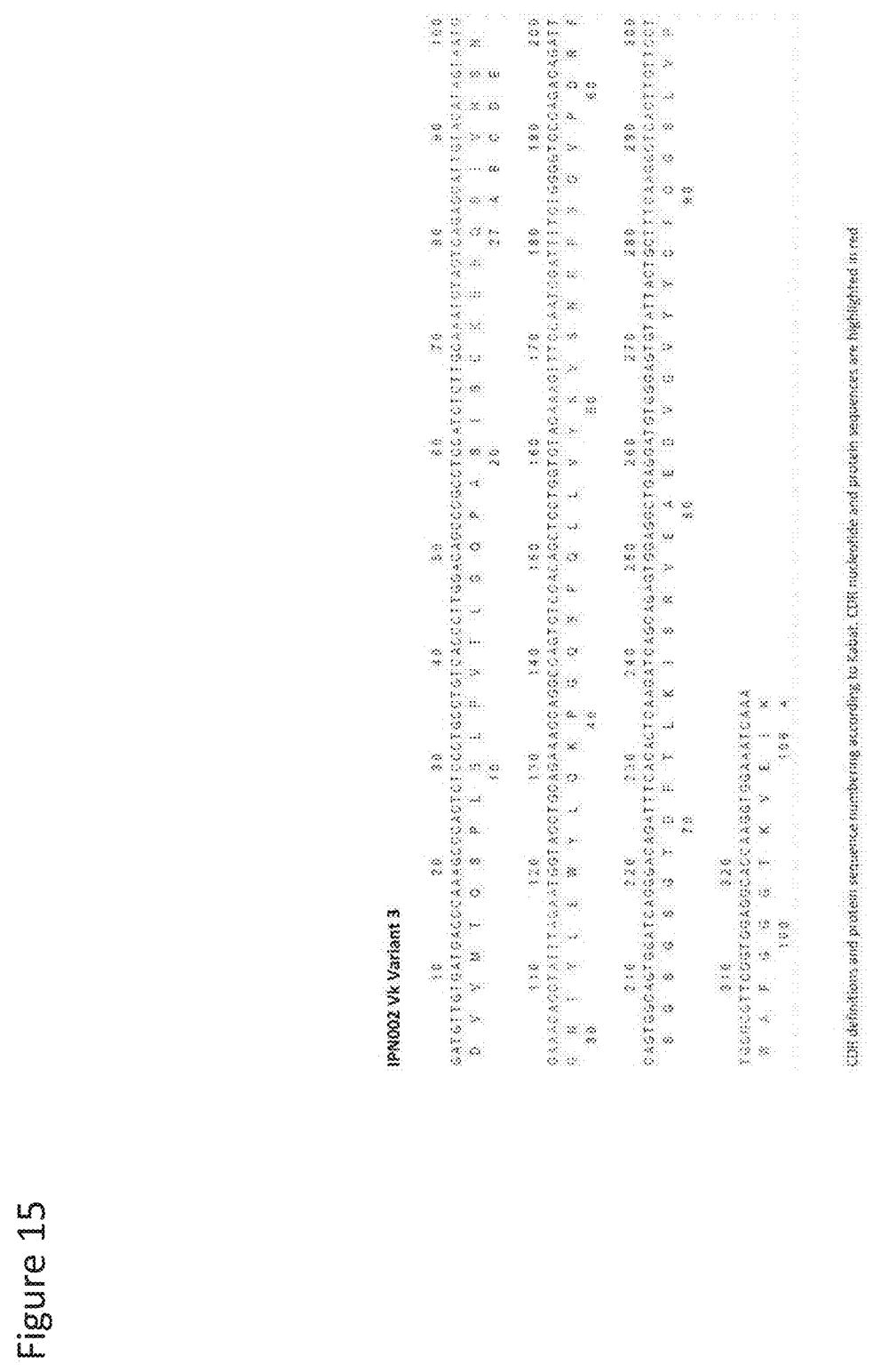

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 15 (Vk variant 3).

Figure 16:
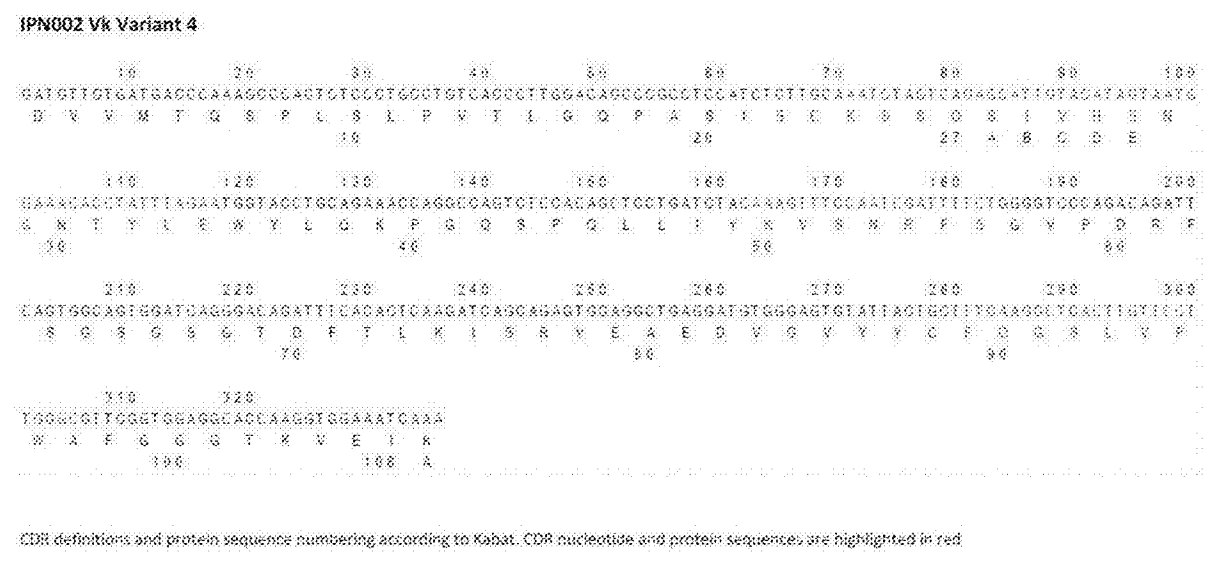

A subject anti-Tau antibody can comprise a light chain variable region comprising an amino acid sequence that is 85%, 86%, 87%, 88%, 89%, 90%, 91%, 92%, 93%, 94%, 95%, 96%, 97%, 98% or 99% identical to the sequence depicted in FIG. 16 (Vk variant 4).

A subject anti-Tau antibody can comprise a heavy chain variable region comprising 1, 2, 3, 4, 5, 6, 7, 8, 9, 10, 11, or 12 of the framework (FR) amino acid substitutions, relative to the IPN002 parental antibody FR amino acid sequences, depicted in Table 2.

TABLE 2

| | | VH Variants | | | |
|---|---|---|---|---|---|
| Amino Acid Position | IPN002 (Parental antibody) | VH Variant 1 | VH Variant 2 | VH Variant 3 | VH Variant 4 |
| FR1 | | | | | |
| 3 | H | H | H | Q | Q |
| 19 | K | R | R | R | R |
| FR2 | | | | | |
| 40 | T | A | A | A | A |
| 42 | D | G | G | G | G |
| 44 | R | G | G | G | G |
| FR3 | | | | | |
| 66 | Q | R | R | R | R |
| 83 | S | S | N | N | N |
| 86 | K | K | R | R | R |

TABLE 2-continued

| | VH Variants | | | | |
|---|---|---|---|---|---|
| Amino Acid Position | IPN002 (Parental antibody) | VH Variant 1 | VH Variant 2 | VH Variant 3 | VH Variant 4 |
| 87 | S | S | A | A | A |
| 93 | S | S | S | S | A |
| FR4 | | | | | |
| 108 | S | S | T | T | T |

For example, a subject anti-Tau antibody can comprise a heavy chain variable region comprising an H→Q substitution at amino acid position 3 in VH FR1 and/or a K→R substitution at amino acid position 19 in VH FR1.

As another example, a subject anti-Tau antibody can comprise a heavy chain variable region comprising a T→A substitution at amino acid position 40 in VH FR2 and/or a D→G substitution at amino acid position 42 in VH FR2 and/or an R→G substitution at position 44 in VH FR2.

As another example, a subject anti-Tau antibody can comprise a heavy chain variable region comprising a Q→R substitution at amino acid position 66 in VH FR3 and/or an S→N substitution at amino acid position 83 in VH FR3 and/or an L→S substitution at amino acid position 85 in VH FR3 and/or a K→R substitution at amino acid position 86 in FR3 and/or an S→A substitution at amino acid position 87 in VH FR3 and/or an S→A substitution at amino acid position 93 in VH FR3.

As another example, a subject anti-Tau antibody can comprise a heavy chain variable region comprising an S→T substitution at amino acid position 108 in VH FR4.

A subject anti-Tau antibody can comprise a light chain variable region comprising 1, 2, 3, 4, 5, 6, 7, 8, 9, or 10 of the framework (FR) amino acid substitutions, relative to the IPN002 parental antibody FR amino acid sequences, depicted in Table 3.

TABLE 3

| | Vk Variants | | | | |
|---|---|---|---|---|---|
| Amino Acid Position | IPN002 (Parental antibody) | Vk Variant 1 | Vk Variant 2 | Vk Variant 3 | Vk Variant 4 |
| FR2 | | | | | |
| 3 | L | L | V | V | V |
| 7 | T | S | S | S | S |
| 14 | S | T | T | T | T |
| 17 | D | Q | Q | Q | Q |
| 18 | Q | P | P | P | P |
| FR2 | | | | | |
| 45 | K | Q | Q | Q | Q |
| 48 | V | V | V | V | I |
| FR3 | | | | | |
| 83 | L | V | V | V | V |
| 85 | T | T | T | V | V |
| FR4 | | | | | |
| 104 | L | V | V | V | V |

For example, a subject anti-Tau antibody can comprise a light chain variable region comprising an L→V substitution at amino acid position 3 in VL FR1 and/or a T→S substitution at amino acid position 7 in VL FR1 and/or an S→T substitution at amino acid position 14 in VL FR1 and/or a D→Q substitution at amino acid position 17 in VL FR1 and/or a Q→P substitution at amino acid position 18 in VL FR1.

As another example, a subject anti-Tau antibody can comprise a light chain variable region comprising a K→Q substitution at amino acid position 45 of VL FR2 and/or a V→I substitution at amino acid position 48 of VL FR2.

As another example, a subject anti-Tau antibody can comprise a light chain variable region comprising an L→V substitution at amino acid position 83 of VL FR3 and/or a T→V substitution at amino acid position 85 of VL FR3.

As another example, a subject anti-Tau antibody can comprise a light chain variable region comprising an L→V substitution at amino acid position 104 of VL FR4.

In some cases, an anti-Tau antibody of the present disclosure comprises:

a) a VH variant 1 comprising the amino acid sequence depicted in FIG. 9; and a Vk variant 1 comprising the amino acid sequence depicted in FIG. 13;

b) a VH variant 1 comprising the amino acid sequence depicted in FIG. 9; and a Vk variant 2 comprising the amino acid sequence depicted in FIG. 14;

c) a VH variant 1 comprising the amino acid sequence depicted in FIG. 9; and a Vk variant 3 comprising the amino acid sequence depicted in FIG. 15;

d) a VH variant 1 comprising the amino acid sequence depicted in FIG. 9; and a Vk variant 4 comprising the amino acid sequence depicted in FIG. 16;

e) a VH variant 2 comprising the amino acid sequence depicted in FIG. 10; and a Vk variant 1 comprising the amino acid sequence depicted in FIG. 13;

f) a VH variant 2 comprising the amino acid sequence depicted in FIG. 10; and a Vk variant 2 comprising the amino acid sequence depicted in FIG. 14;

g) a VH variant 2 comprising the amino acid sequence depicted in FIG. 10; and a Vk variant 3 comprising the amino acid sequence depicted in FIG. 15;

h) a VH variant 2 comprising the amino acid sequence depicted in FIG. 10; and a Vk variant 4 comprising the amino acid sequence depicted in FIG. 16;

i) a VH variant 3 comprising the amino acid sequence depicted in FIG. 11; and a Vk variant 1 comprising the amino acid sequence depicted in FIG. 13;

j) a VH variant 3 comprising the amino acid sequence depicted in FIG. 11; and a Vk variant 2 comprising the amino acid sequence depicted in FIG. 14;

k) a VH variant 3 comprising the amino acid sequence depicted in FIG. 11; and a Vk variant 3 comprising the amino acid sequence depicted in FIG. 15;

l) a VH variant 3 comprising the amino acid sequence depicted in FIG. 11; and a Vk variant 4 comprising the amino acid sequence depicted in FIG. 16;

m) a VH variant 4 comprising the amino acid sequence depicted in FIG. 12; and a Vk variant 1 comprising the amino acid sequence depicted in FIG. 13;

n) a VH variant 4 comprising the amino acid sequence depicted in FIG. 12; and a Vk variant 2 comprising the amino acid sequence depicted in FIG. 14;

o) a VH variant 4 comprising the amino acid sequence depicted in FIG. 12; and a Vk variant 3 comprising the amino acid sequence depicted in FIG. 15; or p) a VH variant 4 comprising the amino acid sequence depicted in FIG. 12; and a Vk variant 4 comprising the amino acid sequence depicted in FIG. 16.

In some embodiments, a subject antibody comprises anti-Tau heavy chain CDRs and anti-Tau light chain CDRs in a single polypeptide chain, e.g., in some embodiments, a subject antibody is a scFv. In some embodiments, a subject antibody comprises, in order from N-terminus to C-terminus: a first amino acid sequence of from about 5 amino acids to about 25 amino acids in length; a CDR1 comprising the amino acid sequence set forth in SEQ ID NO:1; a second amino acid sequence of from about 5 amino acids to about 25 amino acids in length; a CDR2 comprising the amino acid sequence set forth in SEQ ID NO:2; a third amino acid sequence of from about 5 amino acids to about 25 amino acids in length; a CDR3 comprising the amino acid sequence set forth in SEQ ID NO:3; a fourth amino acid sequence of from about 5 amino acids to about 25 amino acids in length; a CDR1 comprising the amino acid sequence set forth in SEQ ID NO:4; a fifth amino acid sequence of from about 5 amino acids to about 25 amino acids in length; a CDR2 comprising the amino acid sequence set forth in SEQ ID NO:5; a sixth amino acid sequence of from about 5 amino acids to about 25 amino acids in length; a CDR3 comprising the amino acid sequence set forth in SEQ ID NO:6; and a seventh amino acid sequence of from about 5 amino acids to about 25 amino acids in length.

In some embodiments, a subject antibody comprises, in order from N-terminus to C-terminus: a light chain FR1 region; a CDR1 comprising the amino acid sequence set forth in SEQ ID NO:1; a light chain FR2 region; a CDR2 comprising the amino acid sequence set forth in SEQ ID NO:2; a light chain FR3 region; a CDR3 comprising the amino acid sequence set forth in SEQ ID NO:3; optionally a light chain FR4 region; a linker region; optionally a heavy chain FR1 region; a CDR1 comprising the amino acid sequence set forth in SEQ ID:4; a heavy chain FR2 region; a CDR2 comprising the amino acid sequence set forth in SEQ ID NO:5; a heavy chain FR3 region; a CDR3 comprising the amino acid sequence set forth in SEQ ID NO:6; and a heavy chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a heavy chain FR1 region; a CDR1 comprising the amino acid sequence set forth in SEQ ID:4; a heavy chain FR2 region; a CDR2 comprising the amino acid sequence set forth in SEQ ID NO:5; a heavy chain FR3 region; a CDR3 comprising the amino acid sequence set forth in SEQ ID NO:6; optionally a heavy chain FR4 region; a linker; optionally a light chain FR1 region; a CDR1 comprising the amino acid sequence set forth in SEQ ID NO:1; a light chain FR2 region; a CDR2 comprising the amino acid sequence set forth in SEQ ID NO:2; a light chain FR3 region; a CDR3 comprising the amino acid sequence set forth in SEQ ID NO:3; and a light chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a light chain FR1 region; a CDR1 comprising the amino acid sequence set forth in SEQ ID NO:7; a light chain FR2 region; a CDR2 comprising the amino acid sequence set forth in SEQ ID NO:8; a light chain FR3 region; a CDR3 comprising the amino acid sequence set forth in SEQ ID NO:9; optionally a light chain FR4 region; a linker region; optionally a heavy chain FR1 region; a CDR1 comprising the amino acid sequence set forth in SEQ ID:10; a heavy chain FR2 region; a CDR2 comprising the amino acid sequence set forth in SEQ ID NO:11; a heavy chain FR3 region; a CDR3 comprising the amino acid sequence set forth in SEQ ID NO:12; and a heavy chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

In some embodiments, a subject antibody comprises, in order from N-terminus to C-terminus: a heavy chain FR1 region; a CDR1 comprising the amino acid sequence set forth in SEQ ID:10; a heavy chain FR2 region; a CDR2 comprising the amino acid sequence set forth in SEQ ID NO:11; a heavy chain FR3 region; a CDR3 comprising the amino acid sequence set forth in SEQ ID NO:12; optionally a heavy chain FR4 region; a linker; optionally a light chain FR1 region; a CDR1 comprising the amino acid sequence set forth in SEQ ID NO:7; a light chain FR2 region; a CDR2 comprising the amino acid sequence set forth in SEQ ID NO:8; a light chain FR3 region; a CDR3 comprising the amino acid sequence set forth in SEQ ID NO:9; and a light chain FR4 region. In some of these embodiments, one or more of the FR regions is a humanized FR region. In some of these embodiments, each of the FR regions is a humanized FR region. The linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO: 50) and $GGGS_n$ (SEQ ID NO: 51), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:52), GGSGG (SEQ ID NO:53), GSGSG (SEQ ID NO: 54), GSGGG (SEQ ID NO: 55), GGGSG (SEQ ID NO: 56), GSSSG (SEQ ID NO: 57), and the like. The ordinarily skilled artisan will recognize that design of a peptide conjugated to any elements described above can include linkers that are all or partially flexible, such that the linker can include a flexible linker as well as one or more portions that confer less flexible structure.

In some embodiments, an anti-Tau antibody of the present disclosure comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 10 amino acids (aa) in length, e.g., 2 aa, 3 aa, 4 aa, 5 aa, 6 aa, 7 aa, 8 aa, 9 aa, or 10 aa in length. Suitable linkers include, e.g., $(Gly)_x$, where x is an integer from 2 to 10. Other suitable linkers are those discussed above. In some embodiments, each of the scFv monomers in a subject scFV multimer is humanized, as described above.

In some cases, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. In some cases, the heavy chain region is of the isotype IgG4. In some of these embodiments, the hinge region comprises an S241P substitution. See, e.g., Angal et al. (1993) *Mol. Immunol.* 30:105. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

A subject antibody can comprise a free thiol (—SH) group at the carboxyl terminus, where the free thiol group can be used to attach the antibody to a second polypeptide (e.g., another antibody, including a subject antibody), a scaffold, a carrier, etc.

In some embodiments, a subject antibody comprises one or more non-naturally occurring amino acids. In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the antibody, where the antibody comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject antibody is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly (iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50000 Da, e.g., from 5000 Da to 40000 Da, or from 25000 to 40000 Da. For example, in some embodiments, where a subject antibody comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

As noted above, in some embodiments, a subject antibody is covalently linked to a PEG polymer. In some embodiments, a subject scFv multimer is covalently linked to a PEG polymer. See, e.g., Albrecht et al. (2006) *J. Immunol. Methods* 310:100. Methods and reagents suitable for PEGylation of a protein are well known in the art and may be found in, e.g., U.S. Pat. No. 5,849,860. PEG suitable for conjugation to a protein is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

The PEG conjugated to the subject antibody can be linear. The PEG conjugated to the subject protein may also be branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

A subject antibody can be glycosylated, e.g., a subject antibody can comprise a covalently linked carbohydrate or polysaccharide moiety. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to an antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of an antibody.

A subject antibody will in some embodiments comprise a "radiopaque" label, e.g. a label that can be easily visualized using for example x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque multiurethanes (see U.S. Pat. No. 5,346,981), organobismuth composites (see, e.g., U.S. Pat. No. 5,256,334), radiopaque barium multimer complexes (see, e.g., U.S. Pat. No. 4,866,132), and the like.

A subject antibody can be covalently linked to a second moiety (e.g., a lipid, a polypeptide other than a subject antibody, a synthetic polymer, a carbohydrate, and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidhexane (BMH), 1,5-difluoro-2,4-dinitrobenzene (DFDNB), and 1,4-di-(3',2'-pyridyldithio) propinoamido butane (DPDPB).

Heterobifunctional cross-linkers have two or more different reactive moieties (e.g., amine reactive moiety and a sulfhydryl-reactive moiety) and are cross-linked with one of the polypeptides via the amine or sulfhydryl reactive moiety, then reacted with the other polypeptide via the non-reacted moiety. Multiple heterobifunctional haloacetyl cross-linkers are available, as are pyridyl disulfide cross-linkers. Carbodiimides are a classic example of heterobifunctional cross-linking reagents for coupling carboxyls to amines, which results in an amide bond.

A subject antibody can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

A subject antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3H$, $^{125}I$, $^{35}S$, $^{14}C$, or $^{32}P$), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

In some embodiments, a subject antibody comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. A subject antibody can be labeled using standard techniques. For example, a subject antibody can be iodinated using chloramine T or 1,3,4,6-tetrachloro-3α,6α-diphenylglycouril. For fluorination, fluorine is added to a subject antibody during the synthesis by a fluoride ion displacement reaction. See, Muller-Gartner, H., TIB Tech., 16:122-130 (1998) and Saji, H., Crit. Rev. Ther. Drug Carrier Syst., 16(2): 209-244 (1999) for a review of synthesis of proteins with such radioisotopes. A subject antibody can also be labeled with a contrast agent through standard techniques. For example, a subject antibody can be labeled with Gd by conjugating low molecular Gd chelates such as Gd diethylene triamine pentaacetic acid (GdDTPA) or Gd tetraazacyclododecanetetraacetic (GdDOTA) to the antibody. See, Caravan et al., Chem. Rev. 99:2293-2352 (1999) and Lauffer et al., J. Magn. Reson. Imaging, 3:11-16 (1985). A subject antibody can be labeled with Gd by, for example, conjugating polylysine-Gd chelates to the antibody. See, for example, Curtet et al., Invest. Radiol., 33(10):752-761 (1998). Alternatively, a subject antibody can be labeled with Gd by incubating paramagnetic polymerized liposomes that include Gd chelator lipid with avidin and biotinylated antibody. See, for example, Sipkins et al., Nature Med., 4:623-626 (1998).

Suitable fluorescent proteins that can be linked to a subject antibody include, but are not limited to, a green fluorescent protein from *Aequoria victoria* or a mutant or derivative thereof e.g., as described in U.S. Pat. Nos. 6,066,476; 6,020, 192; 5,985,577; 5,976,796; 5,968,750; 5,968,738; 5,958,713; 5,919,445; 5,874,304; e.g., Enhanced GFP, many such GFP which are available commercially, e.g., from Clontech, Inc.; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

A subject antibody will in some embodiments be linked to (e.g., covalently or non-covalently linked) a fusion partner, e.g., a ligand; an epitope tag; a peptide; a protein other than an antibody; and the like. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., GST, hemagglutinin (HA; e.g., YPYDVPDYA; SEQ ID NO:63), FLAG (e.g., DYKDDDDK; SEQ ID NO:61), c-myc (e.g., EQKLISEEDL; SEQ ID NO:60), and the like; provide a detectable signal, e.g., an enzyme that generates a detectable product (e.g., β-galactosidase, luciferase), or a protein that is itself detectable, e.g., a green fluorescent protein, a red fluorescent protein, a yellow fluorescent protein, etc.; provides for multimerization, e.g., a multimerization domain such as an Fc portion of an immunoglobulin; and the like.

The fusion may also include an affinity domain, including peptide sequences that can interact with a binding partner, e.g., such as one immobilized on a solid support, useful for identification or purification. Consecutive single amino acids, such as histidine, when fused to a protein, can be used for one-step purification of the fusion protein by high affinity binding to a resin column, such as nickel sepharose. Exemplary affinity domains include His5 (HHHHH) (SEQ ID NO:58), HisX6 (HHHHHH) (SEQ ID NO:59), C-myc (EQKLISEEDL) (SEQ ID NO:60), Flag (DYKDDDDK) (SEQ ID NO:61), StrepTag (WSHPQFEK) (SEQ ID NO:62), hemagglutinin, e.g., HA Tag (YPYDVPDYA; SEQ ID NO:63), glutathinone-S-transferase (GST), thioredoxin, cellulose binding domain, RYIRS (SEQ ID NO:64), Phe-His-His-Thr (SEQ ID NO:65), chitin binding domain, S-peptide, T7 peptide, SH2 domain, C-end RNA tag, WEAAAREACCRECCARA (SEQ ID NO:66), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, 5100 proteins, parvalbumin, calbindin D9K, calbindin D28K, and calretinin, inteins, biotin, streptavidin, MyoD, leucine zipper sequences, and maltose binding protein.

A subject antibody will in some embodiments be fused to a polypeptide that binds to an endogenous blood brain barrier (BBB) receptor Linking a subject antibody to a polypeptide that binds to an endogenous BBB receptor facilitates crossing the BBB, e.g., in a subject treatment method (see below) involving administration of a subject antibody to an individual in need thereof. Suitable polypeptides that bind to an endogenous BBB receptor include antibodies, e.g., monoclonal antibodies, or antigen-binding fragments thereof, that specifically bind to an endogenous BBB receptor. Suitable endogenous BBB receptors include, but are not limited to, an insulin receptor, a transferrin receptor, a leptin receptor, a lipoprotein receptor, and an insulin-like growth factor receptor. See, e.g., U.S. Patent Publication No. 2009/0156498.

As an example, a subject anti-Tau antibody can be a bi-specific antibody comprising a first antigen-binding portion that specifically binds an epitope in a Tau polypeptide (e.g., a linear epitope within an amino-terminal (N-terminal) portion of Tau, e.g., within amino acids 1-25 of Tau, within amino acids 1-18 of Tau, or within amino acids 9 to 18 of Tau); and a second antigen-binding portion that binds an endogenous BBB receptor. For example, in some instances, a subject anti-Tau antibody is a bi-specific antibody comprising a first antigen-binding portion that specifically binds an epitope in a Tau polypeptide (e.g., a linear epitope within an amino-terminal (N-terminal) portion of Tau, e.g., within amino acids 1-25 of Tau, within amino acids 1-18 of Tau, or within amino acids 9 to 18 of Tau); and a second antigen-binding portion that binds a transferrin receptor.

For example, an anti-Tau antibody of the present disclosure can be fused to a peptide that facilitates crossing the BBB, the peptide having a length of from about 15 amino acids to about 25 amino acids, and comprising an amino acid sequence having at least about 85% amino acid sequence identity to one of the following peptides: Angiopep-1 (TFFYGGCRGKRNNFKTEEY) (SEQ ID NO:67); Angiopep-2 (TFFYGGSRGKRNNFKTEEY) (SEQ ID NO:68); cys-Angiopep-2 (CTFFYGGSRGKRNNFKTEEY) (SEQ ID NO:69); Angiopep-2-cys (TFFYGGSRGKRNNFKTEEYC) (SEQ ID NO:70); and an aprotinin fragment (TFVYGGCRAKRNNFKS) (SEQ ID NO:71). See, e.g., U.S. Patent Publication Nos. 2011/0288011; and 2009/0016959. A peptide that facilitates crossing the BBB can be fused to the N-terminus of an anti-Tau light chain region, to the C-terminus of an anti-Tau light chain region, to the N-terminus of an anti-Tau heavy chain region, to the C-terminus of an anti-Tau heavy chain region, to the N-terminus of a subject anti-Tau single-chain antibody, to the C-terminus of a subject anti-Tau single-chain antibody, etc.

In some embodiments, a subject antibody comprises a polyamine modification. Polyamine modification of a subject antibody enhances permeability of the modified antibody at the BBB. A subject antibody can be modified with polyamines that are either naturally occurring or synthetic. See, for example, U.S. Pat. No. 5,670,477. Useful naturally occurring polyamines include putrescine, spermidine, spermine, 1,3-diaminopropane, norspermidine, syn-homospermidine, thermine, thermospermine, caldopentamine, homocaldopentamine, and canavalmine. Putrescine, spermidine and spermine are particularly useful. Synthetic polyamines are composed of the empirical formula $C_xH_yN_z$, can be cyclic or acyclic, branched or unbranched, hydrocarbon chains of 3-12 carbon atoms that further include 1-6 NR or $N(R)_2$ moieties, wherein R is H, $(C_1-C_4)$ alkyl, phenyl, or benzyl. Polyamines can be linked to an antibody using any standard crosslinking method.

In some embodiments, a subject antibody is modified to include a carbohydrate moiety, where the carbohydrate moiety can be covalently linked to the antibody. In some embodiments, a subject antibody is modified to include a lipid moiety, where the lipid moiety can be covalently linked to the antibody. Suitable lipid moieties include, e.g., an N-fatty acyl group such as N-lauroyl, N-oleoyl, etc.; a fatty amine such as dodecyl amine, oleoyl amine, etc.; a C3-C16 long-chain aliphatic lipid; and the like. See, e.g., U.S. Pat. No. 6,638,513). In some embodiments, a subject antibody is incorporated into a liposome.

Methods of Producing a Subject Antibody

A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. *J. Am. Chem. Soc.,* 85: 2149-2156 (1963); Stewart et al., Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 *Protein Pept Lett.* 12:723-8. Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce an anti-tau antibody of the present disclosure (e.g., polynucleotides encoding a subject anti-Tau antibody). See Winnacker, From Genes to Clones, VCH Publishers, N.Y., N.Y. (1987). Suitable mammalian host cells include CHO cell lines, various Cos cell lines, HeLa cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148:1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Compositions

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

Nucleic Acids, Expression Vectors, and Host Cells

The present disclosure provides nucleic acids comprising nucleotide sequences encoding a subject anti-Tau antibody.

A nucleotide sequence encoding subject anti-Tau antibody can comprise a nucleotide sequence encoding a light chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 1B and set forth in SEQ ID NO:17.

A nucleotide sequence encoding subject anti-Tau antibody can comprise a nucleotide sequence encoding a heavy chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 1A and set forth in SEQ ID NO:18.

A nucleotide sequence encoding subject anti-Tau antibody can comprise a nucleotide sequence encoding a light chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 2B and set forth in SEQ ID NO:19.

A nucleotide sequence encoding subject anti-Tau antibody can comprise a nucleotide sequence encoding a heavy chain variable region and having at least 85%, 86%, 87%, 88%, 89%, 90%, 91%, 92%, 93%, 94%, 95%, 96%, 97%, 98% or 99% nucleotide sequence identity to the nucleotide sequence depicted in FIG. 2A and set forth in SEQ ID NO:20.

A nucleotide sequence encoding a subject antibody can be operably linked to one or more regulatory elements, such as a promoter and enhancer, that allow expression of the nucleotide sequence in the intended target cells (e.g., a cell that is genetically modified to synthesize the encoded antibody).

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro*. 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein— Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject antibody can be present in an expression vector and/or a cloning vector. Where a subject antibody comprises two separate polypeptides, nucleotide sequences encoding the two polypeptides can be cloned in the same or separate vectors. An expression vector can include a selectable marker, an origin of replication, and other features that provide for replication and/or maintenance of the vector.

Large numbers of suitable vectors and promoters are known to those of skill in the art; many are commercially available for generating a subject recombinant constructs. The following vectors are provided by way of example. Bacterial: pBs, phagescript, PsiXl74, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, a subject nucleic acid comprises a nucleotide sequence encoding a subject antibody. A subject nucleic acid can comprise a nucleotide sequence encoding heavy- and light-chain CDRs of IPN001. In some embodiments, a subject nucleic acid comprises a nucleotide sequence encoding heavy- and light-chain CDRs of IPN002, where the CDR-encoding sequences are interspersed with FR-encoding nucleotide sequences. In some embodiments, the FR-encoding nucleotide sequences are human FR-encoding nucleotide sequences.

Host Cells

The present disclosure provides isolated genetically modified host cells (e.g., in vitro cells) that are genetically modified with a subject nucleic acid. In some embodiments, a subject isolated genetically modified host cell can produce a subject antibody.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLL3), human embryonic kidney (HEK) cells (ATCC No. CRL1573), HLHepG2 cells, and the like. In some cases, the cells are HEK cells. In some cases, the cells are CHO cells, e.g., CHO-K1 cells (ATCC No. CCL-61), CHO-M cells, CHO-DG44 cells (ATCC No. PTA-3356), and the like.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. Non-limiting examples of other suitable bacteria include, but are not limited to, *Bacillus subtilis*, and the like. In some embodiments, the host cell is *Escherichia coli*.

Pharmaceutical Formulations

The present disclosure provides compositions, including pharmaceutical compositions, comprising a subject antibody. In general, a formulation comprises an effective amount of a subject antibody. An "effective amount" means a dosage sufficient to produce a desired result, e.g., reduction in an adverse symptom associated with a tauopathy, amelioration of a symptom of a tauopathy, slowing progression of a tauopathy, etc. Generally, the desired result is at least a reduction in a symptom of a tauopathy, as compared to a control. A subject antibody can be delivered in such a manner as to avoid the blood-brain barrier, as described in more detail below. A subject antibody can be formulated and/or modified to enable the antibody to cross the blood-brain barrier.

Formulations

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, a subject antibody can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of a subject antibody; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody; 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM Sucrose; and has a pH of 5.5; or 4) 75 mg/mL of a subject antibody; 0.04% Tween 20 w/v; 20 mM L-histidine; and 250 mM trehalose; and has a pH of 5.5; or 6) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.022% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like.

Furthermore, a subject antibody can be made into suppositories by mixing with a variety of bases such as emulsifying bases or water-soluble bases. A subject antibody can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-Tau antibody of the present disclosure, calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations may be prevented by using appropriate additives, by controlling moisture content and by developing specific polymer matrix compositions.

Controlled release within the scope of the present disclosure can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a tauopathy. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a subject antibody is administered by injection and/or delivery, e.g., to a site in a brain artery or directly into brain tissue. A subject antibody can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Detection Methods

The present disclosure provides in vitro methods of detecting a Tau polypeptide in a biological sample obtained from an individual; and methods of detecting a Tau polypeptide in a living individual in vivo. A subject in vitro detection method can be quantitative. Tau can thus serve as a biomarker for progression of a tauopathy, or response to treatment for a tauopathy.

The Tau polypeptide that is detected/quantitated can be: a) full-length Tau; b) an N-terminal fragment of full-length Tau; c) total Tau, where "total Tau" can include full-length Tau of any isoform; and any N-terminal Tau fragments that are present in a biological sample and that display the epitope recognized by a subject anti-Tau antibody. Amino acid sequences of human full-length Tau are presented in FIGS. 6A-D.

Suitable biological samples include, e.g., cerebrospinal fluid, blood, plasma, serum, urine, and saliva.

An in vitro method of the present disclosure of detecting a Tau polypeptide in a biological sample obtained from an individual generally involves: a) contacting the biological sample with an anti-Tau antibody as described herein; and b) detecting binding of the antibody to Tau polypeptide present in the sample. In some cases, the anti-Tau antibody comprises VH and/or VL CDRs of IPN001. In some cases, the anti-Tau antibody comprises VH and/or VL CDRs of IPN002.

A detection method of the present disclosure can be used to determine whether an individual has, or is at risk of developing, a tauopathy. A detection method of the present disclosure can be used to determine the stage (severity) of a tauopathy. A detection method of the present disclosure can be used to determine a patient's response to a treatment regimen for treating a tauopathy. A biological sample can be tested using a subject detection method, where the biological sample is obtained from an individual suspected of having a tauopathy, an individual who has been diagnosed as having a tauopathy, an individual who has a genetic predisposition to developing a tauopathy, etc.

The present disclosure provides a method of diagnosing a neurodegenerative tauopathy in an individual. The method generally involves (a) assessing the level of a Tau polypeptide in a biological sample obtained from the individual; and (b) comparing the level of the Tau polypeptide to a reference, a standard, or a normal control value that indicates the level of Tau in normal control subjects. A significant difference between the level of Tau polypeptide in the biological sample and the normal control value indicates that the individual has a neurodegenerative tauopathy.

The present disclosure provides a method of monitoring the progression of, or monitoring response to treatment for, a neurodegenerative tauopathy in an individual. The method generally involves comparing the level of a Tau polypeptide in a biological sample obtained from the individual at a first time point with the level of a Tau polypeptide in a biological sample obtained from the individual at a second time point. A difference in the level of the Tau polypeptide in a biological sample obtained from the individual at a second time point, compared to the level of the Tau polypeptide in a biological sample obtained from the individual at a first time point, can provide an indication as to: i) whether the tauopathy is progressing or whether progression of the disease has halted; and/or ii) how quickly the tauopathy is progressing; and/or iii) whether the individual is exhibiting a beneficial clinical response to treatment with a drug or other treatment regimen for treating the tauopathy.

The present disclosure provides a method of staging a tauopathy. For example, a subject method can provide for staging Alzheimer's disease. For example, the level of a Tau polypeptide in a biological sample (e.g., the CSF or other liquid biological sample) from a living individual can provide an indication as to the Braak stage of AD. Braak and Braak (1995) *Neurobiol. Aging* 16:271. For example, the level of a Tau polypeptide in a biological sample from a living individual can provide an indication as to whether the individual is in transentorhinal stages I-II of AD; limbic stages III-IV of AD; or neocortical stages V-VI of AD.

The level of a Tau polypeptide in a biological sample can be assessed by any suitable method known in the art. Suitable methods include, but are not limited to, a protein ("Western") blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry.

The present disclosure provides a method of monitoring progression of a tauopathy in an individual, where the method generally involves: a) determining a first level of a Tau polypeptide in a biological sample obtained from the individual at a first time point; b) determining a second level of a Tau polypeptide in a biological sample obtained from the individual at a second time point; and c) comparing the second level of Tau with the first level of Tau. The determining steps can comprise: i) contacting the biological sample with a subject anti-Tau antibody; and ii) quantitating binding of the antibody to Tau polypeptide present in the sample.

In some cases, the first time point is a time point before initiation of a treatment regimen, and the second time point is a time point after initiation of a treatment regimen. Thus, the instant disclosure provides a method of monitoring response to treatment with an agent that treats a tauopathy, where the method involves: a) determining a first level of a Tau polypeptide in a biological sample obtained from the individual at a first time point that is before treatment with an agent to treat a tauopathy is initiated; b) determining a second level of a Tau polypeptide in a biological sample obtained from the individual at a second time point that is after initiation of treatment with an agent to treat a tauopathy; and c) comparing the second level of Tau with the first level of Tau.

A subject method of monitoring progression of a tauopathy can also be applied to methods of monitoring progression of a synucleinopathy, e.g., Parkinson's disease (PD); dementia with Lewy Bodies (DLB); multiple system atrophy (MSA);

etc. For example, progression of PD with dementia (PDD) can be monitored with a subject method.

In some tauopathies, the level of Tau increases with progression of the disease. In other tauopathies, the level of Tau decreases with progression of the disease. Thus, e.g., the level of Tau increases with progression of AD; and decreases with progression of FTD.

A subject method can involve use of a kit or an assay device comprising a subject anti-Tau antibody. The present disclosure provides kits and assay devices for carrying out a method as described herein. A subject kit includes an anti-tau antibody of the present disclosure.

The anti-tau antibody can be immobilized on an insoluble support (e.g., a test strip, a well of a multi-well plate, a bead (e.g., a magnetic bead), etc.). Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

An anti-tau antibody of the present disclosure can comprise a detectable label. Where the antibody comprises a detectable label, a subject kit can include one or more reagents for developing the detectable label. A labeled antibody can comprise a label such as a chemiluminescent agent, a particulate label, a colorimetric agent, an energy transfer agent, an enzyme, a fluorescent agent, or a radioisotope. Suitable detectable labels include any composition detectable by spectroscopic, photochemical, biochemical, immunochemical, electrical, optical, or chemical means. Suitable detectable labels include, but are not limited to, fluorescent labels (e.g., fluorescein isothiocyanate, texas red, rhodamine, a green fluorescent protein, a red fluorescent protein, a yellow fluorescent protein, and the like); radiolabels (e.g., $^3$H, $^{125}$I, $^{35}$S, $^{14}$C, or $^{32}$P); and enzymes (e.g., horse radish peroxidase, alkaline phosphatase, luciferase, and other enzymes that act on a substrate to produce a product that can be detected by fluorometric, colorimetric, or spectrophotometric means).

A subject kit can further include one or more additional components, where suitable additional components include: 1) a positive control; 2) a buffer (e.g., a binding buffer; a wash buffer; etc.); 3) reagents for use in generating a detectable signal; and the like. Other optional components of the kit include: a protease inhibitor; a detectable label; etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

An assay device can include a subject anti-Tau antibody immobilized on a solid substrate. The assay device can be in any of a variety of formats, e.g., a test strip, a dipstick; etc.

In Vivo Imaging

As discussed above, the present disclosure provides methods of detecting a Tau polypeptide in a living individual, e.g., by an in vivo imaging technique. For example, in one embodiment, in vivo imaging of a Tau polypeptide can be accomplished by positron emission tomography (PET), single photon emission tomography (SPECT), near infrared (NIR) optical imaging, or magnetic resonance imaging (MRI). A subject anti-tau antibody is administered to an individual, and the presence and/or level of the tau polypeptide is detected. The anti-tau antibody can comprise a label suitable for use in PET, SPECT, NIR, or MRI. Such labels include a contrast agent or a radioisotope, where the contrast agent or radioisotope is one that is suitable for use in imaging, e.g., imaging procedures carried out on humans, as described above. In some cases, the anti-Tau antibody comprises VH and/or VL CDRs of IPN001. In some cases, the anti-Tau antibody comprises VH and/or VL CDRs of IPN002. The anti-Tau antibody can comprise one or more humanized framework regions, as described above.

Generating a Report

In some instances, a subject detection method comprises detecting a Tau polypeptide in a biological sample obtained from an individual; and, based on the level of detected Tau polypeptide, generating a report and/or directing therapy or management of the individual from whom the biological sample was obtained.

A report can include one or more of: an indication as to whether the individual likely has a tauopathy; an indication of the severity of the tauopathy; an indication as to whether the individual exhibits a beneficial clinical response to treatment for the tauopathy; and the like.

Thus, a report can include information such as a predicted likelihood that the individual has, or will develop, a tauopathy; a recommendation regarding further evaluation; a recommendation regarding therapeutic drug and/or other health management intervention; and the like.

For example, the methods disclosed herein can further include a step of generating or outputting a report providing the results of a subject assessment, which report can be provided in the form of an electronic medium (e.g., an electronic display on a computer monitor), or in the form of a tangible medium (e.g., a report printed on paper or other tangible medium). An assessment as to the likelihood that a person has, or at risk of developing, a tauopathy can be referred to as a "risk report," "a risk score," or "a likelihood score." A person or entity that prepares a report ("report generator") may also perform steps such as sample gathering, sample processing, and the like. Alternatively, an entity other than the report generator can perform steps such as sample gathering, sample processing, and the like. A risk assessment report can be provided to a user. A "user" can be a health professional (e.g., a clinician, a laboratory technician, or a physician).

Directing Health Management

In some instances, a subject detection method comprises detecting a Tau polypeptide in a biological sample obtained from an individual; and, based on the level of detected Tau polypeptide, generating a report and/or directing therapy or management of the individual from whom the biological sample was obtained.

Thus, e.g., depending on the outcome of a subject detection method, a recommendation can be made that the individual undergo therapeutic intervention (treatment) for the tauopathy and/or that the individual be considered for special health management.

Therapeutic intervention can include, e.g., drug therapy for the treatment of Alzheimer's disease. Examples of drug therapy for the treatment of Alzheimer's disease include, but are not limited to, acetylcholinesterase inhibitors, including, but not limited to, Aricept (donepezil), Exelon (rivastigmine), metrifonate, and tacrine (Cognex); an anti-Aβ antibody (e.g., solanezumab); an anti-tau antibody; non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Dosages for each of the above agents are known in the art. For example, Aricept can be administered at 50 mg orally per day for 6 weeks, and, if well tolerated by the individual, at 10 mg per day thereafter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Cloning and Sequencing of IPN001 and IPN002 VH and VL Regions

Amino acid sequences of the VH and VL regions of IPN001 (also referred to herein as "IPN1" or "IPN-1") and IPN002 (also referred to herein as "IPN2" or "IPN-2") antibodies were determined. The amino acid sequences of the VH and VL regions of IPN001 are depicted in FIGS. 1A and 1B, respectively. The amino acid sequences of the VH and VL regions of IPN002 are depicted in FIGS. 2A and 2B, respectively. The CDRs are in bold text and are underlined. CDRs were determined using the method of Kabat et al. (see Table 1; and J. Biol. Chem. 252:6609-6616 (1977); and Kabat et al., U.S. Dept. of Health and Human Services, "Sequences of proteins of immunological interest" (1991)).

Example 2

Electrophysiological Analysis of the Effect of Anti-Tau Antibodies

Materials and Methods

Whole cell patch clamp recording from induced pluripotent stem cells (iPSC) derived cortical neurons cultured on a monolayer of normal human astrocytes was carried out using a patch pipette (2-5 MOhm) filled with solution containing (mM): K-methyl-sulfate (140), NaCl (10), $CaCl_2$ (1), Mg-ATP (3); Na-GTP (0.4), EGTA (0.2), HEPES (10), Phosphocreatine with adjusted pH=7.3 and mOsm=300. Neurons were perfused (2 ml/min) with artificial cerebral spinal fluid containing (mM): NaCl (140), KCl (2.5), $MgCl_2$ (2) $CaCl_2$ (2), Hepes (10), D-Glucose (10), sucrose (20). Adjusted pH=7.4 mOsm=310. Recordings were done using pClamp-10.3 data acquisition software (Molecular Devices) and MultiClamp 700B amplifier (Axon Instrument; Foster City Calif.). AD tau and AD Tau pre-incubated with IPN001 or IPN002 (2-hrs at room temperature or 24-hrs at 4 degree C. at 10:1 weight ratio) were applied via MinisQuirt micro-perfusion system (AutoMate, Berkeley, Calif.). Data analysis was done off-line using Clampfit 10.2 analysis software (Molecular Devices). All recordings were done at room temperature.

Results

The data are depicted in FIGS. 3A-D.

Application of AD-Tau (6 μg/ml) causes cortical neuron membrane depolarization (A, B, and C). Pre-incubation of AD-Tau (6 ug/ml) with IPN001 (60 μg/ml) (A) or IPN002 (60 μg/ml) (B) for >2 hrs reduces AD-Tau mediated membrane depolarization. C. Pre-incubation of AD-Tau (6 μg/ml) with mouse IgG (60 μg/ml) did not reduce AD-Tau mediated membrane depolarization in cortical neurons. D. Data summary showing IPN001 and IPN002 significantly reduced AD-Tau mediated membrane depolarization (Paired t-test * p<0.037; ** p<0.009, p<0.003).

Example 3

Immunoreactivity of IPN001 and IPN002 with Tau in CSF from AD Patients

Cerebrospinal fluid (CSF) was pooled from 10 healthy donors (1 ml each). CSF was also pooled from 10 Alzheimer's disease (AD) patients (1 ml each). Aliquots of CSF pools were saved for ELISA analysis. 10 mls of conditioned media from cortical neurons differentiated for 315 days from a Down's induced pluripotent stem cell (iPSC) iPSC line (8941.1) was used as a control for the CSF affinity isolations and an aliquot was also saved for ELISA analysis. To determine if CSF contains IPN002-reactive Tau, each of the CSF pooled samples and conditioned media were precleared on an IgG1 coupled resin and the flow-through subsequently applied to an IPN001-coupled resin. The IPN001 resins were washed thoroughly with phosphate buffered saline (PBS) and bound proteins eluted with 50 mM Glycine, 150 mM NaCl, pH 2.3 and neutralized with 1M Tris, pH 8.3 after elution. The eluted proteins were concentrated on YM10 concentrators and added to sample buffer for sodium dodecyl sulfate-polyacrylamide gel electrophoresis (SDS-PAGE) electrophoresis and Western blotting analysis.

Figure 4A:
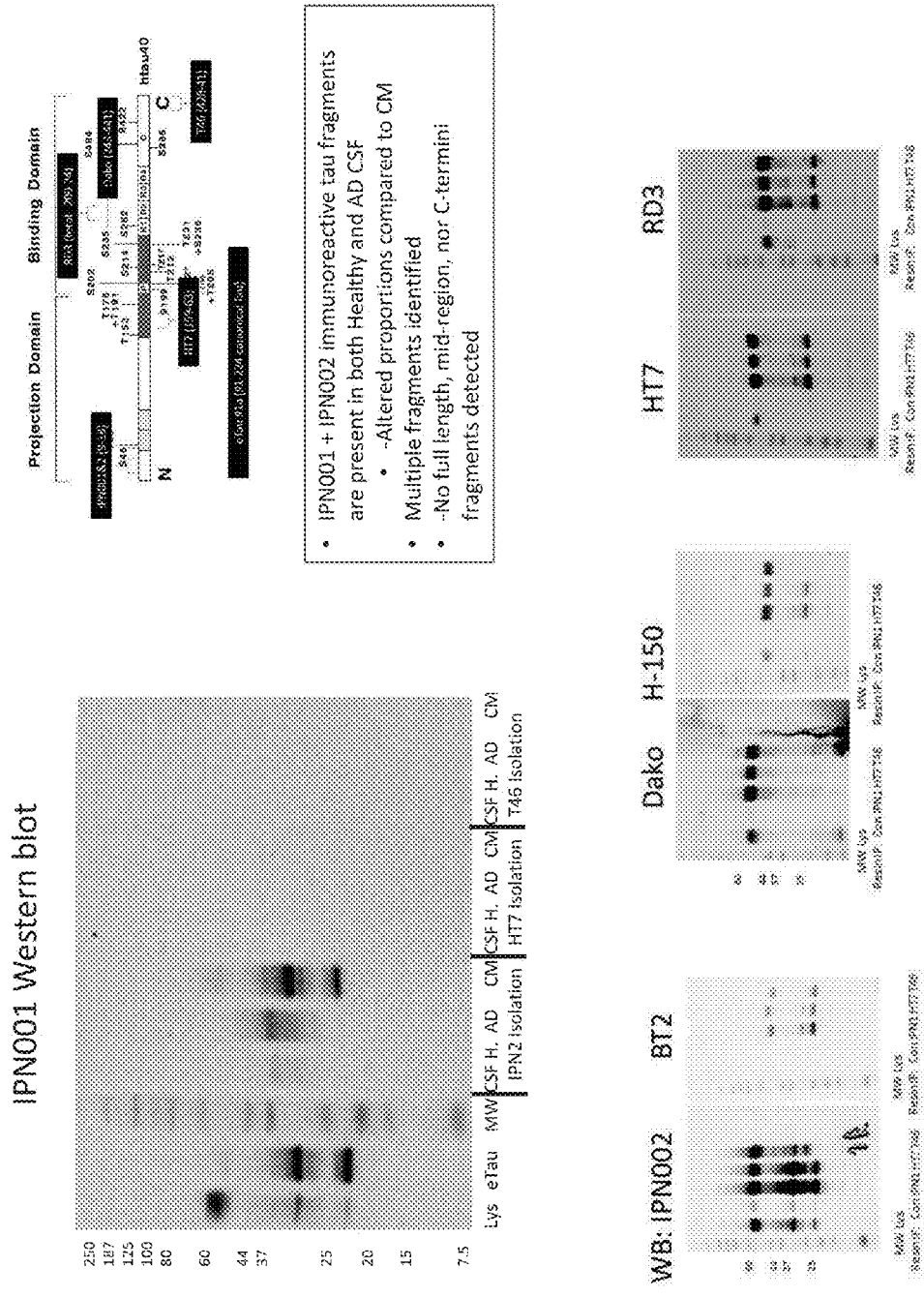
FIGS. 4A-C depict affinity isolation of Tau from cerebrospinal fluid (CSF).
Figure 4B:
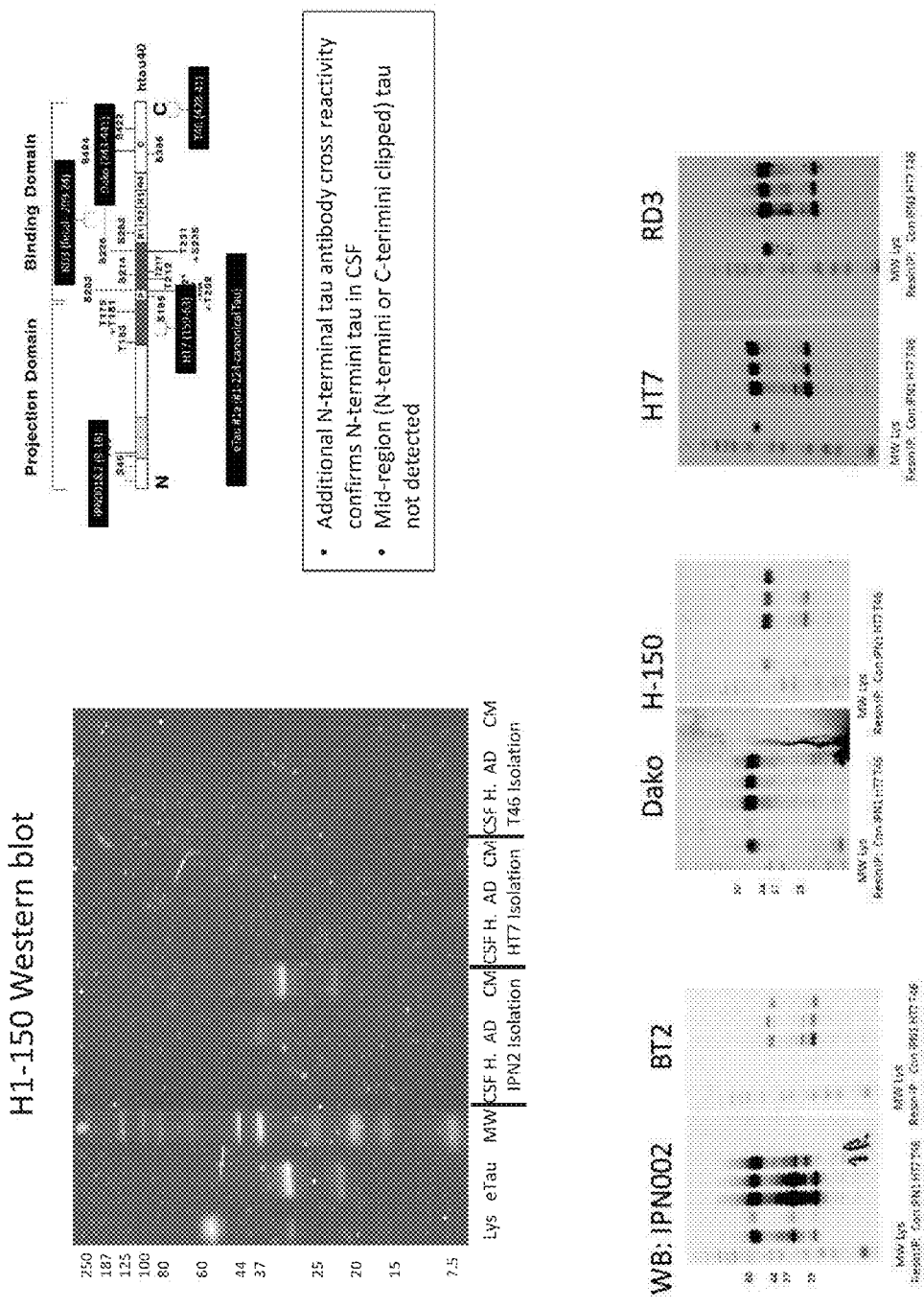
Figure 4C:
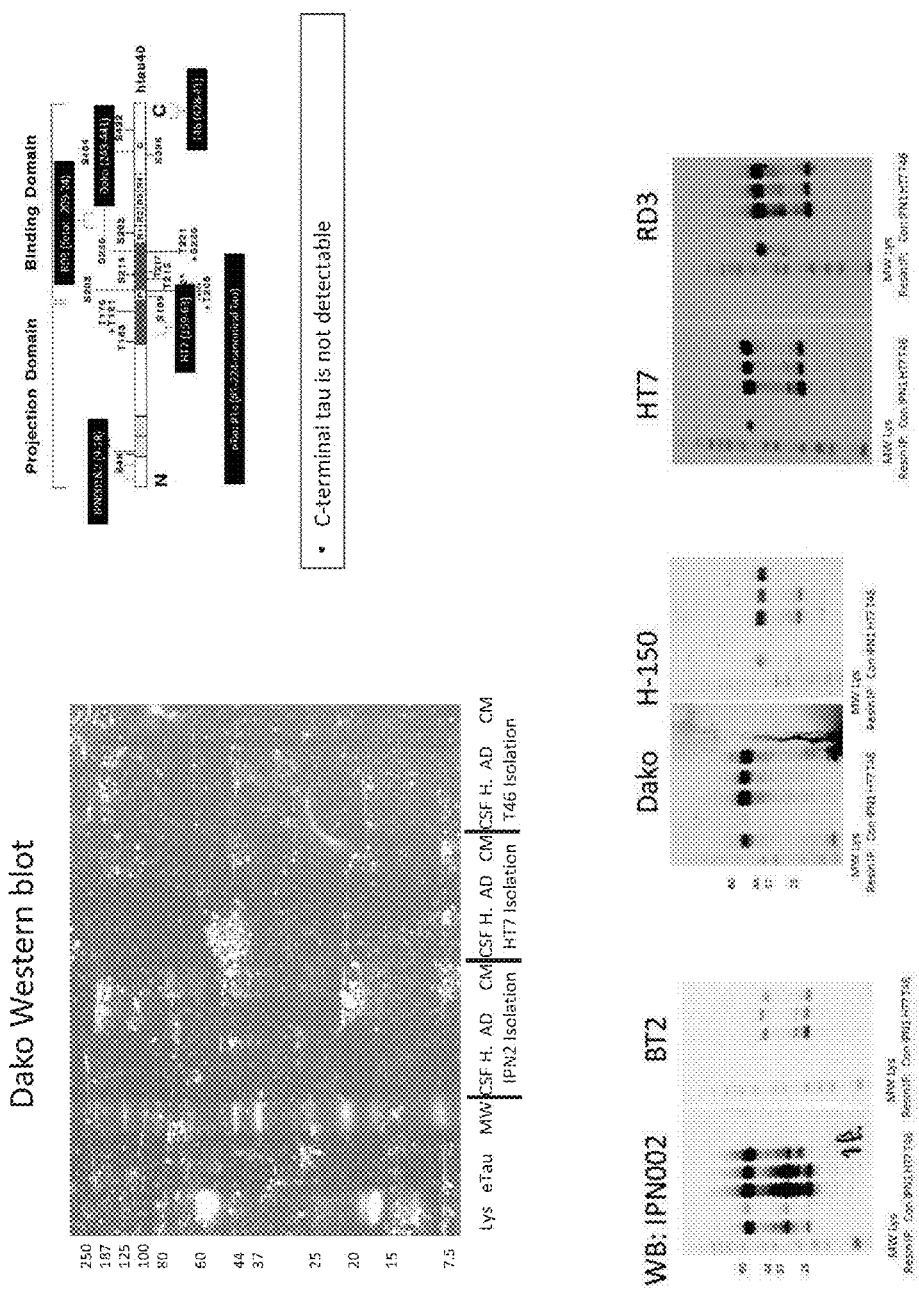

To determine if IPN002 reacts with any form of Tau in the CSF, Western blots of the IPN002 eluted protein were probed with IPN001, Santa Cruz Tau H-150 (aa1-150) and with Dako's Tau #A0024 antibody which reacts with the C-termini (aa#243-441) of Tau. The data are depicted in FIGS. 4A-C.

Western blots showed IPN001 (FIG. 4a) and Tau H-150 (FIG. 4b) immunoreactive bands present in the IPN002 affinity purified protein from both healthy and AD CSF that ranged in molecular weight from ~25 kd to 37 kd. These Tau fragments were similar in their sizes, but not in their relative abundance, to eTau fragments isolated from the Down's line conditioned media. The Dako C-terminal tau antibody (FIG. 4c) did not detect any reactive species from the IPN002 affinity isolation from either CSF or from conditioned media. Full-length Tau was not detected by any of the Tau antibodies from the IPN002 affinity isolation. Because the IPN002 affinity isolated proteins were reactive with IPN001 and IPN002 on Western blot, it was concluded that Tau in CSF is also IPN001 reactive.

The CSF and conditioned media flow-through from the IPN002 affinity resins were then applied sequentially to and eluted from T46 (Tau #428-441) and HT7 (Tau #159-163) to determine if any C-terminal or mid-region tau fragments were present that were not isolated by IPN002. The eluates were probed with the Dako C-terminal antibody (FIG. 4c) but no immunoreactivity was detected. These data suggest that IPN001 and IPN002 immunoreactive tau is more abundant than full length, mid-region only or C-terminal tau fragments.

Figure 5:
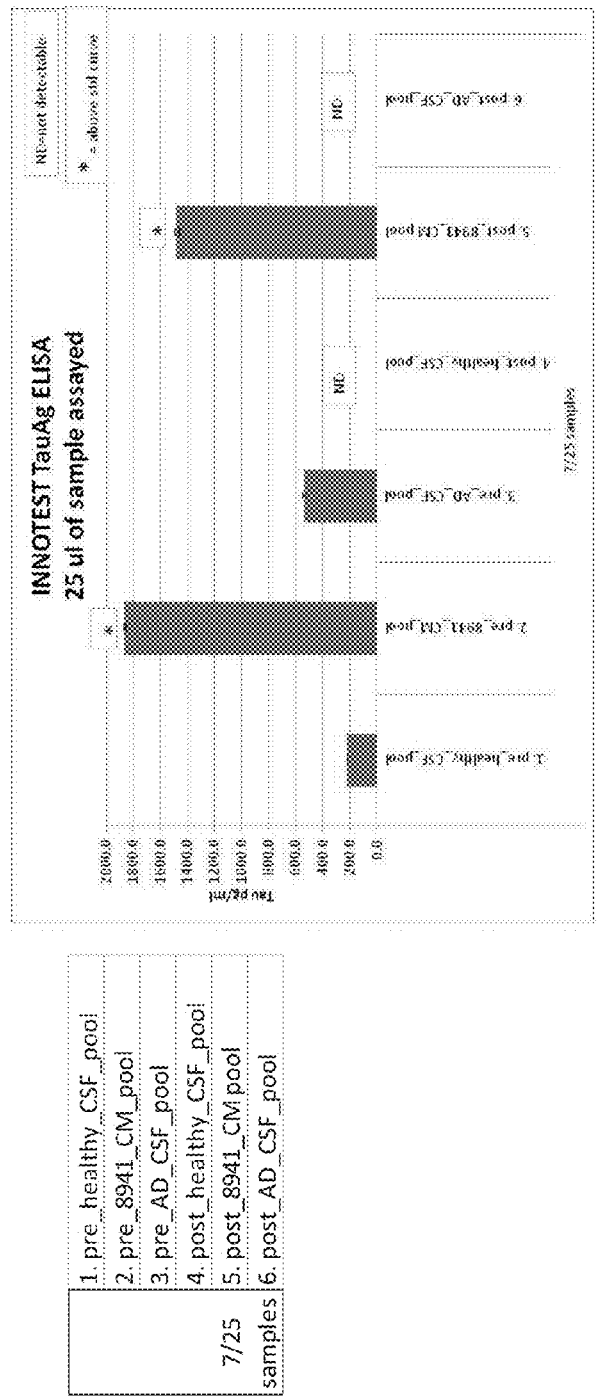
FIG. 5 depicts quantification of CSF and conditioned medium (CM) samples pre- and post-Tau affinity isolation.

Aliquots of the flow-through from each of the CSFs and conditioned media were saved for pre-versus post-isolation comparison to determine if all detectable tau was removed during the isolation, using a commercially available kit commonly used to determine Tau levels in CSF. The data are shown in FIG. 5. This analysis demonstrated that all the detectable tau was removed from the post-CSF samples during the affinity isolation process.

These data provide strong evidence that both IPN001 and IPN002 react with the major tau species present in CSF from both healthy and AD patients.

Example 4

Detection of eTau in Patient Samples

Materials and Methods
Conditioned Media Collection from iPSC-Derived Cortical Neurons iPSC (induced pluripotent stem cells) were generated from healthy age matched controls and Alzheimer's patients using the Yamanaka method (Takahashi et al. (2007) Cell 131(5), 861) as described in Dimos et al. (2008) Science 321:1218. iPSC were differentiated to cortical neurons largely in line with published protocols using the dual SMAD monolayer method (Chambers et al. (2009) Nat. Biotechnol. 27:275) followed by cortical neuron differentiation similar to that described in Shi et al. (2012) Nat. Neurosci. 15:477). iPSC-derived cortical neurons (iPSC-CN), cultured for 108 days, were washed, fresh media added, and conditioned media collected after three days unless otherwise noted. Multiple differentiations from the lines were conducted to ensure reproducibility of the eTau levels. Conditioned media was spun at 15,000 rpm for 15 minutes prior to processing for Western blot or tau ELISA. For the brefeldin A experiment, iPSC-CN cultures were washed with PBS prior to addition of fresh media with and without 1 µM brefeldin A and media conditioned for one hour prior to collection.
Conditioned Media Collection from Human Primary Cortical Neurons Human cortical neuron cultures (HCC) were prepared as described in Wright et al. (2007) Neurobiol. Aging 28:226. Briefly, human fetal cerebral cortical tissue was obtained by Advanced Bioscience Resources (Alameda, Calif.) and complied with federal guidelines for fetal research and with the Uniformed Anatomical Gift Act. The tissue was rinsed in Hank's buffered saline solution (Cellgro) and triturated in the presence of 1 µg/ml DNase (EMD) and passed through a 100 µm cell strainer. After centrifugation the pellet was resuspended in 0.05% trypsin/EDTA (Invitrogen) for 20 min at 37° C. Trypsin was inactivated by adding an equal volume of media containing 10% fetal bovine serum (FBS) and sample gently triturated again in presence of DNase. After centrifugation, cells were resuspended in plating media (Neurobasal containing B27, Invitrogen) and counted. Cells were plated in plates or on coverslips coated with poly-d-lysine with laminin. Three week old HCC were washed, fresh media added and media collected after three days of conditioning. Conditioned media was spun at 15,000 rpm for 15 minutes prior to processing for Western blot.
P301L Mouse ISF and Human CSF Collections Mice were anesthetized using isoflurane (2%, 800 mL/min $O_2$). Bupivacain/epinephrine was used for local analgesia and fynadine or carprophen for peri-/post-operative analgesia. The animals were placed in a stereotaxic frame (Kopf instruments, USA). Push-pull microdialysis probes (phosphatidyl ethanolamine (PEE) membrane, Brainlink, the Netherlands) were inserted into the hippocampus (3 mm exposed surface). Microdialysis sampling was performed 24 and 48 hours after surgery. On the days of the sampling, the probes of the animals were connected with fluorinated ethylene propylene (FEP) tubing to a microperfusion pump (Harvard PHD 2000 Syringe pump, Holliston, Mass. or similar). Microdialysis probes were perfused with artificial CSF (aCSF) containing 147 mM NaCl, 3.0 mM KCl, 1.2 mM $CaCl_2$ and 1.2 mM $MgCl_2$, and 0.15% bovine serum albumin (BSA) at a flow rate of 0.75 µL/min. Microdialysis samples were collected for 60 minute periods. After the stabilization period, basal samples were collected. On the second day of sampling, the above procedure was repeated (Brains Online). The interstitial fluid (ISF) was spun at 15,000 rpm for 15 minutes and cleared supernatants used for eTau Western blots.

10 mls of CSF (Precision Med) from a pool of 10 healthy (Precision Med), 10 AD patients (Precision Med) and 10 PSP patients were collected, spun at 15,000 rpm for 15 minutes, supernatants precleared on IgG affinity resin followed by tau isolation on an IPN002 anti-tau affinity resin, washed, eluted with 50 mM glycine, pH 2.3 with 150 mM NaCl into a tube containing 1M TBS, pH 8.3 to neutralize the pH, concentrated on YM10 filters and prepared for tau Western blots. iPSC-CN conditioned media from a fAD PSEN1 patient was similarly isolated as a positive control to compare banding patterns.
Western Blots Conditioned media were diluted in Laemmli buffer (Sigma). Cultured neurons were rinsed with PBS before incubation in 0.05% trypsin in DMEM (Invitrogen), rinsed and lysed in Laemmli buffer. All samples were boiled, separated on tris-glycine polyacrylamide gels (Invitrogen) and transferred to nitrocellulose using iBlot (Invitrogen). Membranes were incubated in blocking buffer (LiCor), probed with 0.5 µg/ml IPN001 antibody to tau and antibody to β-actin (1:2000; Abcam) in blocking buffer containing 0.1% Tween-20, and anti-mouse 680 and anti-rabbit 800 secondary antibodies (LiCor). Blots were scanned with the Odyssey SA infrared imaging system and analyzed using Odyssey SA software (LiCor).
Tau ELISA Media were collected after a three day conditioning period from iPSC-derived cortical neuron cultures and assayed using an Alphascreen homogeneous assay to measure tau. 10 µg/ml anti-tau AlphaLISA acceptor beads and 1 nM biotinylated-anti-tau antibody were mixed with conditioned media overnight at room temperature. 40 µg/ml streptavidin-donor beads (Perkin Elmer) were added for 30 minutes at room temperature and the plate read on Envision plate reader.

eTau Purification

Conditioned media collected from iPSC-CN from AD patients was spun at 15,000 rpm for 15 minutes, supernatants collected and precleared on an IgG affinity resin. The precleared supernatant was passed through an IPN002 anti-tau antibody resin, washed and eTau eluted with 50 mM sodium citrate, pH 2.3 with 150 mM NaCl into a tube containing 1M TBS, pH 8.3 to neutralize the pH. The eluate was concentrated and buffer exchanged to PBS.

Immunofluorescence

MCC were rinsed with PBS, fixed in 4% paraformaldehyde, blocked with 10% normal donkey serum (Jackson ImmunoResearch) in PBS, permeabilized (unless otherwise specified) with 0.2% Triton-x-100 in PBS for 15 minutes, and stained using IPN001 antibody to tau with donkey-anti-mouse-A488 secondary antibody (Molecular Probes) and DAPI (Invitrogen). Images were acquired using the Leica DMI 600 B microscope at 40× using the LAS AF software (Leica). Confocal images were acquired using the Nikon Eclipse Ti confocal microscope (Nikon).

Results

Figure 7:
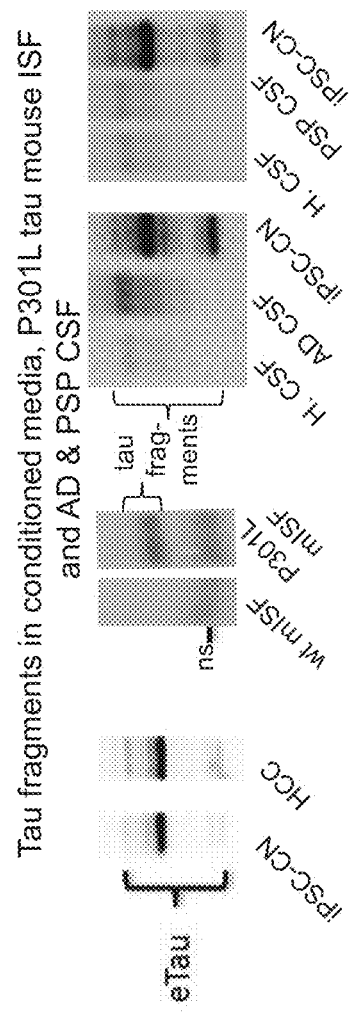
FIG. 7 depicts detection of Tau fragments in conditioned medium, in interstitial fluid (ISF) from P301L tau mice, and in CSF from PSP and AD patients

Assays were conducted to detect eTau fragments in various fluids. The results are depicted in FIG. 7. As shown in FIG. 7, left panel, endogenous tau is secreted from cortical neurons derived from human induced pluripotent stem cells (human iPSC-cortical neurons; iPSC-CN), where the secreted Tau is referred to as extracellular Tau or "eTau." As shown in FIG. 7, second panel from left, eTau is also present in conditioned media from human primary neurons (human cortical cells; "HCC"), confirming that eTau is not an artifact of iPSC-differentiation. These eTau fragments were also detected in neuronal lysates, suggesting that tau is cleaved inside neurons prior to eTau secretion.

As shown in FIG. 7, middle panel, similar tau fragments were detected in interstitial fluid (ISF) from P301L tau mice, where full length tau was not detected in either system. P301L mice are transgenic for a form of human tau having a P301L mutation; P301L mice are models for human tauopathy. See, e.g., Gotz et al. (2001) *J. Biol. Chem.* 276:529; and Lewis et al. (2000) *Nature Genetics* 25:402.

As shown in FIG. 7, right panels, eTau levels are increased in CSF from AD patients, and in multiple lines from familial AD (fAD) patients compared to lines from healthy patients. As shown in FIG. 7, right panels, eTau was also detected in CSF from PSP patients.

Example 5 eTau Induces Neuronal Hyperactivity

Methods

Whole cell patch clamp recording from iPSC-CN cultured on monolayer of normal human astrocytes using micro-pipette (2-5 MOhm) were filled with solution containing (mM): K-methyl-sulfate (140), NaCl (10), CaCl$_2$ (1), Mg-ATP (3); Na-GTP (0.4), EGTA (0.2), HEPES (10), Phosphocreatine (10) with adjusted pH=7.3, and mOsm=305. Neurons were perfused (2 ml/min) with artificial cerebral spinal fluid containing (mM): NaCl (140), KCl (2.5), MgCl$_2$ (2) CaCl$_2$ (2), Hepes (10), D-Glucose (10), sucrose (20), adjusted pH=7.4 mOsm=310. Recordings were made using pClamp-10.3 data acquisition software (Molecular Devices) and MultiClamp 700B amplifier (Axon Instrument; Foster City Calif.). Puff application of eTau, or eTau with inhibitors, tetrodotoxin (TTX) (Tocris), MK801 (Sigma), NBQX (Tocris), or anti-tau antibody, IPN001, was performed using MiniSquirt microperfusion system (AutoMate, Berkeley, Calif.). Off-line data analysis used Clampfit 10.2 analysis software (Molecular Devices). Recordings were conducted at 34-37° C.

Results

To determine whether eTau can alter neuronal function, purified eTau fragment eTau was applied to iPSC-CN or HCC. The results are shown in FIGS. 8A-C.

Figure 8:
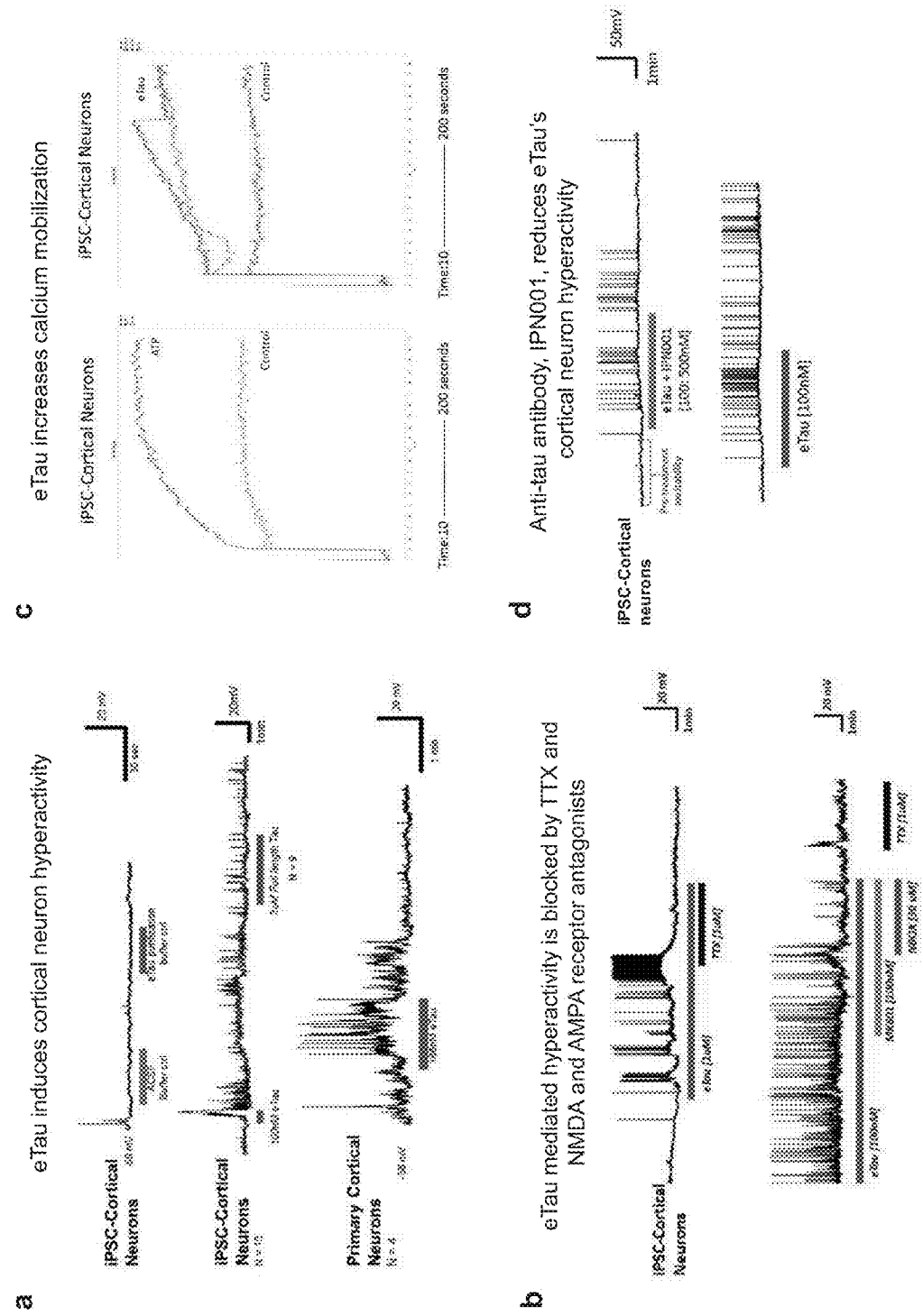
FIGS. 8A-D depict induction of cortical neuron hyperactivity by an extracellular tau (eTau) fragment (FIGS. 8A-C); and reduction of eTau-induced neuronal hyperactivity by anti-Tau antibody IPN001.

As shown in FIG. 8A, addition of a purified eTau fragment mixture onto these neurons promoted hyperactivity. As shown in FIG. 8B, hyperactivity induced by the eTau mixture was inhibited by tetrodotoxin (TTX) and by the NMDA and AMPA glutamate receptor antagonists, MK801 and NBQX, respectively. TTX blocks action potentials in nerves by binding to the voltage-gated, fast sodium channels in nerve cell membranes. These data suggest that eTau-induced neuronal hyperactivity is dependent on action potential-mediated release of glutamate. In contrast, as shown in the middle panel of FIG. 8A, application of full length tau produced no detectable changes in neuronal activity even at substantially higher concentrations, showing that eTau-induced hyperactivity is dependent on tau fragments. These eTau-induced hyperactivity results strongly suggest that calcium mobilization could be occurring in the neurons. To determine whether calcium mobilization occurs in the neurons, the effect of eTau on calcium mobilization was tested. As shown in FIG. 8C, eTau-1a robustly mobilized calcium. This type of neuronal hyperactivity, if sustained in a chronic setting such as in AD, could result in neuronal dysfunction through altered synaptic firing and aberrant neuronal stimulation.

Example 6

Anti-tau antibody reduces eTau-mediated neuronal hyperactivity

Electrophysiological analyses were carried out as described in Example 5. The effect of IPN001 and IPN002 on e-Tau-mediated neuronal hyperactivity was assessed.

As shown in FIG. 8D, IPN001 reduces eTau-mediated neuronal hyperactivity. As shown in FIG. 19B, IPN002 reduces eTau-mediated neuronal hyperactivity.

Example 7

Humanized Anti-Tau Antibodies A3

Humanized variants of IPN002 were generated. Amino acid sequences of the heavy chain VH domains of humanized variants 1-4, and nucleotide sequences encoding the heavy chain VH domain of the humanized variants, are shown in FIGS. 9-12. Amino acid sequences of the light chain VL domain of humanized variants 1-4, and nucleotide sequences encoding the light chain VL domain of the humanized variants, are shown in FIGS. 13-16. Amino acid differences relative to the amino acid sequence of IPN002 are summarized in Tables 4 and 5.

TABLE 4

VH Variants

| Amino Acid Position | IPN002 (Parental antibody) | VH Variant 1 | VH Variant 2 | VH Variant 3 | VH Variant 4 |
|---|---|---|---|---|---|
| 3 | H | H | H | Q | Q |
| 19 | K | R | R | R | R |
| 40 | T | A | A | A | A |
| 42 | D | G | G | G | G |
| 44 | R | G | G | G | G |
| 66 | Q | R | R | R | R |
| 83 | S | S | N | N | N |
| 86 | K | K | R | R | R |
| 87 | S | S | A | A | A |
| 93 | S | S | S | S | A |
| 108 | S | S | T | T | T |

TABLE 5

Vk Variants

| Amino Acid Position | IPN002 (Parental antibody) | Vk Variant 1 | Vk Variant 2 | Vk Variant 3 | Vk Variant 4 |
|---|---|---|---|---|---|
| 3 | L | L | V | V | V |
| 7 | T | S | S | S | S |
| 14 | S | T | T | T | T |
| 17 | D | Q | Q | Q | Q |
| 18 | Q | P | P | P | P |
| 45 | K | Q | Q | Q | Q |
| 48 | V | V | V | V | I |
| 83 | L | V | V | V | V |
| 85 | T | T | T | V | V |
| 104 | L | V | V | V | V |

Single letter amino acid codes are as follows:
G—Glycine (Gly)
P—Proline (Pro)
A—Alanine (Ala)
V—Valine (Val)
L—Leucine (Leu)
I—Isoleucine (Ile)
M—Methionine (Met)
C—Cysteine (Cys)
F—Phenylalanine (Phe)
Y—Tyrosine (Tyr)
W—Tryptophan (Trp)
H—Histidine (His)
K—Lysine (Lys)
R—Arginine (Arg)
Q—Glutamine (Gln)
N—Asparagine (Asn)
E—Glutamic Acid (Glu)
D—Aspartic Acid (Asp)
S—Serine (Ser)
T—Threonine (Thr)

Example 8

Characterization of Humanized IPN002 Variants

The relative tau binding affinities for binding to each of the recombinant tau (383 amino acid recombinant tau) as well as to eTau 1a, eTau1b, eTau2, eTau3 and eTau4 for each of the 16 antibody combinations of VH#1-4 with Vk#1-4 are shown in Table 4, which is presented in FIG. 17. The relative binding affinities for each tau and eTau species range from 121 pM to 1030 pM for each of the VH/Vk antibody combinations.

To obtain absolute affinities as well as $K_{on}$ and $K_{dis}$ for these VH/Vk human antibodies, Octet analysis was conducted using tau (383 amino acid recombinant tau). The $K_D$'s ranged from 42.6 pM to 2120 pM. For all VH/Vk variants, the $K_{on}$ values were high, and $K_{dis}$ values were low for Tau and for each eTau species. The data are provided in Table 5, which is presented in FIG. 18.

A subset of the above-described humanized IPN002 variants was tested in additional analysis. As shown in FIG. 19A, three variants, VH2/Vk1, VH2/Vk2, and VH2/Vk3, were used in a Western blot assay with a variety for samples containing tau. The tau-containing samples included iPSC-CN conditioned media; iPSC-CN lysates; AD brain lysates; and P301L tau mouse brain cortex lysates; and cynomologus monkey brain lysates. The data show that the above-described humanized IPN002 variants are reactive with tau in a variety of samples.

A subset of the above-described humanized IPN002 variants was tested for the ability to reduce eTau-induced neuronal hyperactivity. As shown in FIG. 19B, parental IPN002, and variants VH2/Vk1, VH2/Vk2, and VH2/Vk3 blocked eTau induced hyperactivity.

Example 9

Testing the Immunogenicity of Humanized IPN002 Variants

Humanized anti-tau antibody was assessed for immunogenic potential. An EpiScreen™ assay was used. See, e.g., Jones et al. (2004) J. Interferon Cytokine Res. 24:560; and Jones et al. (2005) J. Thromb. Haemost. 3:991. Time course T cell assays were performed using $CD8^+$-depleted peripheral blood mononuclear cells (PBMC); and T cell proliferation was measured by incorporation of [$^3$H]-thymidine at various time points after addition of test antibody samples.

PBMC were isolated from healthy community donor buffy coats (e.g., from blood drawn within 24 hours of testing). T cell responses to a test antibody (e.g., a humanized IPN002 variant) were compared to a clinical standard antibody.

Purified test antibody (humanized IPN002 variant) was added to PBMC cultures in vitro to a final concentration of 50µg/ml in culture medium, to generate a test sample. A clinical antibody control (positive control), and a culture medium-only control (unstimulated control), were included as control samples. Test samples (PBMC plus test antibody), and control samples, were incubated for 8 days at 37° C. with 5% $CO_2$. On days 5, 6, 7, and 7, the cells in the test and control samples were suspended and transferred to wells of a multi-well culture plate. The test and control samples were pulsed with 0.75 µCi [$^3$H]-thymidine and incubated for a further 18 hours before harvesting onto filter mats. Counts per minute (cpm) for each well were determined using scintillation counting.

For proliferation assays, a threshold of an SI equal to or greater than 2 was used, where samples inducing a proliferative response above this threshold were considered positive. SI (Stimulation Index) is the mean test sample counts divided by the mean of the unstimulated control.

Figure 21:
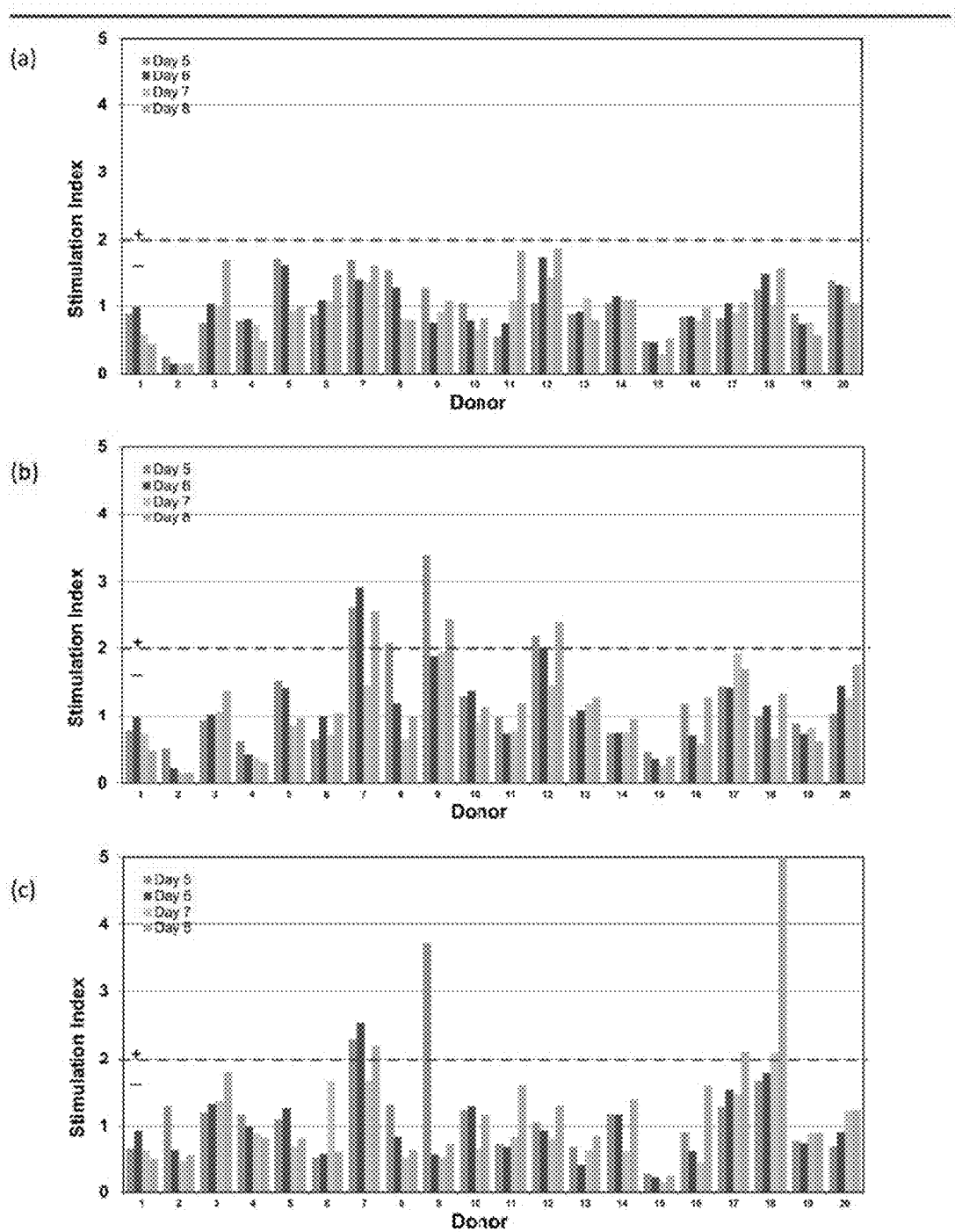
FIGS. 21A-C depict proliferation responses to a humanized anti-Tau antibody (FIG. 21A), a chimeric antibody (FIG. 21B), and humanized A33 (FIG. 21C).

The data are shown in FIGS. 21A-C. Healthy donor T cell proliferation responses to a humanized IPN002 test antibody. PBMC from bulk cultures were sampled an assessed for proliferation on days 5, 6, 7, and 8 after incubation with the test samples. Proliferation responses with an SI≥2.0 (p<0.05), indicated by the dashed horizontal line, that were significant (p<0.05) using an unpaired, two sample student's t test were considered positive.

As shown in FIG. 21A, a test fully humanized IPN002 antibody had low immunogenic potential (below the SI threshold of 2.0). FIG. 21B shows results with a reference chimeric antibody, where the reference chimeric antibody has IPN002 murine heavy and light chain variable regions and human IgG4 constant region; and FIG. 21C shows results with an immunogenic clinical control humanized A33 antibody.

Example 10

IPN002 Reduces the Level of Phosphorylated Tau In Vivo

The effect of IPN002 administration on the level of Tau that is phosphorylated at amino acids 202 and 205 was assessed.

The P301L mouse model was used. P301L mice are transgenic for a form of human tau having a P301L mutation; P301L mice are models for human tauopathy. See, e.g., Gotz et al. (2001) *J. Biol. Chem.* 276:529.

P301L mice (3-4 months old) were treated with: 1) control IgG; 2) PHF1 anti-phosphorylated Tau antibody; or 3) IPN002. IgG control and IPN002 antibodies were injected intraperitoneally at a concentration of 10 mg/kg for 4 weeks; then at 20 mg/kg for a further 4 weeks. PHF1 was administered at 10 mg/kg for the entire 8-week course. On day 60 after the beginning of the antibody treatment regimen, the level of phosphorylated Tau was measured in the hippocampus. The data are depicted in FIG. 22.

Figure 22:
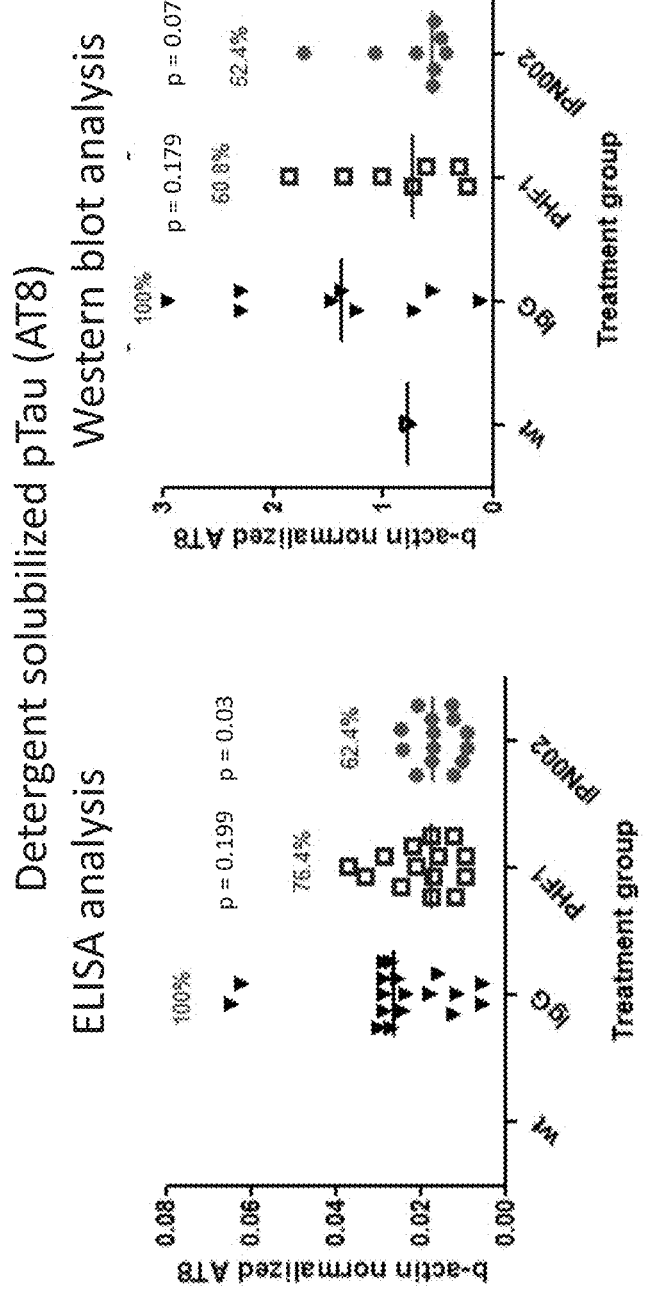
FIG. 22 depicts the effect of IPN002 on phosphorylated Tau levels in vivo.

Tau that is phosphorylated at amino acids 202 and 205 is referred to as "AT8." As shown in FIG. 22, treatment with IPN002 resulted in a statistically significant decrease in insoluble phospho-Tau (AT8) as assessed by ELISA (left panel), and trending toward a decrease as assessed by Western blot analysis (right panel) compared to IgG control treatment. PHF1 treatment showed a trend toward a decrease in insoluble AT8, in support of findings by Chai et al. ((2011) *J. Biol. Chem.* 286:34457) and Boutajangout et al. ((2011) *J. Neurochem.* 118:658).

Example 11

IPN002 Reduces Free Tau Levels in Both ISF and CSF

The effect of IPN002 administration on levels of free tau in CSF and interstitial fluid (ISF) was determined. P301L mice were treated as described in Example 10. The level of free tau present in ISF that is not bound to IPN002 was determined using IPN001. As shown in FIG. 23, IPN002 treatment reduced free Tau levels (not bound to IPN002) (left panel) in ISF in P301L mice treated with IPN002.

To determine whether IPN002 reduces free Tau levels in CSF to the same extent as it does in ISF, P301L mice were treated as described in Example 10, and the effect of IPN002 treatment on the level of free tau (not bound to IPN002) in the CSF of the treated mice was determined. The results are shown in FIG. 24.

In the left panel of FIG. 24, the levels of free tau (unbound to IPN002; referred to as "Free tau (of IPN002)") in CSF of untreated, control IgG-treated, PHF1-treated, and IPN002-treated mice, are shown. As shown in the right panel of FIG. 24, free tau levels in CSF is comparable to free tau levels in ISF of IPN002-treated mice, demonstrating that ISF tau analysis correlates well with the more clinically relevant material, CSF.

Example 12

Anti-Tau Antibody Reduces eTau-Mediated Neuronal Hyperactivity

Electrophysiological analyses were carried out as described in Example 5. The effect of IPN002 on e-Tau-induced neuronal hyperactivity was assessed.

As shown in FIG. 25, IPN002 reduces eTau-mediated neuronal hyperactivity.

Example 13

Tau Fragments are Present in CSF Obtained from Individuals with Likely Chronic Traumatic Encephalopathy (CTE)

CSF samples were obtained from former National Football League linemen, who exhibited behavioral/cognitive deficits, and who were considered likely to have CTE. The CSF samples were assayed for the presence of eTau fragments. eTau fragments were affinity isolated from pooled CSF from healthy individuals and individuals with likely CTE. The isolated eTau fragments were separated using polyacrylamide gel electrophoresis; and the separated fragments were transferred to a membrane. The membrane was probed with IPN001. The results, presented in FIG. 26, show that Tau fragments are present in CSF obtained from individuals with likely CTE.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a tauopathy in an individual, the method comprising administering to the individual a pharmaceutical composition comprising an antibody that specifically binds Tau and a pharmaceutically acceptable excipient suitable for administration to a human, wherein the antibody comprises:

a) a light chain region comprising:

(i) a $V_L$ CDR1 comprising the amino acid sequence of SEQ ID NO:1 or SEQ ID NO:7;

(ii) a $V_L$ CDR2 comprising the amino acid sequence of SEQ ID NO:2 or SEQ ID NO:8;

(iii) a $V_L$ CDR3 comprising the amino acid sequence of SEQ ID NO:3 or SEQ ID NO:9; and (vii) a humanized light chain framework region; and b) a heavy chain region comprising:

(i) a $V_H$ CDR1 comprising the amino acid sequence of SEQ ID NO:4 or SEQ ID NO:10;

(ii) a $V_H$ CDR2 comprising the amino acid sequence of SEQ ID NO:5 or SEQ ID NO:11:

(iii) a $V_H$ CDR3 comprising the amino acid sequence of SEQ ID NO:6 or SEQ ID NO:12; and (iv) a humanized heavy chain framework region.

2. The method of claim 1, wherein the antibody is encapsulated in a liposome.

3. The method of claim 1, wherein the antibody is formulated with an agent that facilitates crossing the blood-brain barrier.

4. The method of claim 1, wherein the antibody is fused, directly or via a linker, to a carrier molecule, a peptide or a protein that promotes the crossing of the blood-brain barrier.

5. The method of claim 1, wherein the antibody is a Fv, scFv, Fab, F(ab')2, or Fab'.

6. The method of claim 1, wherein said administering results in reduction in one or more of:
 a) the amount of free extracellular tau in brain tissue;
 b) the neuron-to-neuron spread of tau;
 c) the amount of intraneuron tau aggregates;
 d) the degree of microglial and/or astrocyte activation;
 e) the amount of phosphorylated or hyperphosphorylated tau;
 f) the amount of total Tau;
 g) the amount of intracellular N-terminal tau fragments; and
 h) neuronal hyperactivity.

7. The method of claim 1, further comprising administering at least one additional agent that treats the tauopathy.

8. The method of claim 1, wherein said administering is intravenous.

9. The method of claim 1, wherein said administering is intrathecal.

10. A pharmaceutical formulation, the formulation comprising: an antibody that specifically binds Tau and a pharmaceutically acceptable excipient suitable for administration to a human, wherein the antibody comprises:
 a) a light chain region comprising:
  (i) a $V_L$ CDR1 comprising the amino acid sequence of SEQ ID NO:1 or SEQ ID NO:7;
  (ii) a $V_L$ CDR2 comprising the amino acid sequence of SEQ ID NO:2 or SEQ ID NO:8;
  (iii) a $V_L$ CDR3 comprising the amino acid sequence of SEQ ID NO:3 or SEQ ID NO:9; and
  (iv) a humanized light chain framework region; and
 b) a heavy chain region comprising:
  (i) a $V_H$ CDR1 comprising the amino acid sequence of SEQ ID NO:4 or SEQ ID NO:10;
  (ii) a $V_H$ CDR2 comprising the amino acid sequence of SEQ ID NO:5 or SEQ ID NO:11;
  (iii) a $V_H$ CDR3 comprising the amino acid sequence of SEQ ID NO:6 or SEQ ID NO:12; and
  (iv) a humanized heavy chain framework region.

11. The pharmaceutical formulation of claim 10, wherein the humanized light chain framework region comprises 1, 2, 3, 4, 5, 6, 7, 8, 9, or 10 of the amino acid substitutions depicted in Table 3.

12. The pharmaceutical formulation of claim 10, wherein the humanized heavy chain framework region comprises 1, 2, 3, 4, 5, 6, 7, 8, 9, 10, 11, or 12 of the amino acid substitutions depicted in Table 2.

13. The pharmaceutical formulation of claim 10, wherein the antibody is encapsulated in a liposome.

14. The pharmaceutical formulation of claim 10, wherein the antibody is formulated with an agent that facilitates crossing the blood-brain barrier.

15. The pharmaceutical formulation of claim 10, wherein the antibody is fused, directly or via a linker, to a carrier molecule, a peptide or a protein, wherein the carrier molecule, peptide, or protein promotes the crossing of the blood-brain barrier.

16. The pharmaceutical formulation of claim 10, wherein the antibody is a Fv, scFv, Fab, F(ab')2, or Fab'.

17. An antibody that specifically binds Tau, wherein the antibody comprises:
 a) a light chain region comprising:
  i) a $V_L$ CDR1 comprising the amino acid sequence of SEQ ID NO:1 or SEQ ID NO:7;
  (ii) a $V_L$ CDR2 comprising the amino acid sequence of SEQ ID NO:2 or SEQ ID NO:8;
  (iii) a $V_L$ CDR3 comprising the amino acid sequence of SEQ ID NO:3 or SEQ ID NO:9; and
  (iv) a humanized light chain framework region; and
 b) a heavy chain region comprising:
  (i) a $V_H$ CDR1 comprising the amino acid sequence of SEQ ID NO:4 or SEQ ID NO:10;
  (ii) a $V_H$ CDR2 comprising the amino acid sequence of SEQ ID NO:5 or SEQ ID NO:11;
  (iii) a $V_H$ CDR3 comprising the amino acid sequence of SEQ ID NO:6 or SEQ ID NO:12; and
  (iv) a humanized heavy chain framework region.

18. The antibody of claim 17, wherein the light chain region and the heavy chain region are present in separate polypeptides.

19. The antibody of claim 17, wherein the light chain region and the heavy chain region are present in a single polypeptide.

20. The antibody of claim 17, wherein the heavy chain region is of the isotype IgG1, IgG2, IgG3, or IgG4.

21. The antibody of claim 17, wherein the antibody is a Fv, scFv, Fab, F(ab')2, or Fab'.

22. The antibody of claim 17, wherein the antibody comprises a covalently linked non-peptide synthetic polymer.

23. The antibody of claim 22, wherein the synthetic polymer is a poly(ethylene glycol) polymer.

24. The antibody of claim 17, wherein the antibody is fused, directly or via a linker, to a carrier molecule, a peptide or a protein, wherein the carrier molecule, peptide, or protein promotes the crossing of the blood-brain barrier.

25. A recombinant expression vector comprising a nucleotide sequence encoding the antibody of 17, wherein the nucleotide sequence is operably linked to a transcriptional control element that is active in a eukaryotic cell.

26. An in vitro host cell genetically modified with the recombinant expression vector of claim 25.

27. A sterile container comprising the pharmaceutical formulation of claim 10.

28. The container of claim 27, wherein the container is a syringe.

29. A method of monitoring progression of a tauopathy in an individual, the method comprising:
 a) determining a first level of a Tau polypeptide in a biological sample obtained from the individual at a first time point;
 b) determining a second level of a Tau polypeptide in a biological sample obtained from the individual at a second time point; and
 c) comparing the second level of Tau with the first level of Tau,
 wherein said determining comprises:
  i) contacting the biological sample with an antibody of claim 17; and
  ii) quantitating binding of the antibody to Tau polypeptide present in the sample.

30. The method of claim 29, wherein the biological sample is cerebrospinal fluid, blood, plasma, serum, urine, or saliva.

31. The method of claim 29, wherein the quantitated Tau polypeptide is total Tau polypeptide.

32. The method of claim 29, wherein the quantitated Tau polypeptide is an N-terminal fragment of a full-length Tau polypeptide.

33. The method of claim 29, wherein the first time point is a time point before initiation of a treatment regimen, and wherein the second time point is a time point after initiation of a treatment regimen.

34. A method of detecting a Tau polypeptide in a living individual in vivo, the method comprising:
   a) administering to the individual an antibody of claim 17; and
   b) detecting binding of the antibody to tau polypeptide in a brain tissue in the individual using an imaging method.

35. The method of claim 34, wherein the antibody comprises a contrast agent suitable for use in the imaging method.

36. The method of claim 34, wherein the imaging method is magnetic resonance imaging or positron emission tomography.

37. An in vitro method of detecting a Tau polypeptide in a biological sample obtained from an individual, the method comprising:
   1) contacting the biological sample with an antibody that specifically binds Tau, wherein the antibody comprises:
      a) a light chain region comprising:
         (i) a $V_L$ CDR1 comprising the amino acid sequence of SEQ ID NO:1 or SEQ ID NO:7;
         (ii) a $V_L$ CDR2 comprising the amino acid sequence of SEQ ID NO:2 or SEQ ID NO:8;
         (iii) a $V_L$ CDR3 comprising the amino acid sequence of SEQ ID NO:3 or SEQ ID NO:9; and
         (iv) a humanized light chain framework region; and
      b) a heavy chain region comprising:
         (i) a $V_H$ CDR1 comprising the amino acid sequence of SEQ ID NO:4 or SEQ ID NO:10;
         (ii) a $V_H$ CDR2 comprising the amino acid sequence of SEQ ID NO:5 or SEQ ID NO:11;
         (iii) a $V_H$ CDR3 comprising the amino acid sequence of SEQ ID NO:6 or SEQ ID NO:12: and
         (iv) a humanized heavy chain framework region; and
   2) detecting binding of the antibody to Tau polypeptide present in the sample.

38. The method of claim 37, wherein the biological sample is blood, serum, plasma, urine, saliva, or cerebrospinal fluid.

39. The method of claim 37, wherein the individual is suspected of having a tauopathy, has been diagnosed as having a tauopathy, or has a genetic predisposition to developing a tauopathy.

40. The method of claim 37, wherein the method is quantitative.

41. The method of claim 37, wherein the Tau polypeptide detected is total Tau polypeptide.

42. The method of claim 37, wherein the Tau polypeptide detected is an N-terminal fragment of a full-length Tau polypeptide.

43. The method of claim 1, wherein the antibody comprises:
   a) a light chain region comprising:
      (i) a $V_L$ CDR1 comprising the amino acid sequence of SEQ ID NO:1;
      (ii) a $V_L$ CDR2 comprising the amino acid sequence of SEQ ID NO:2;
      (iii) a $V_L$ CDR3 comprising the amino acid sequence of SEQ ID NO:3; and
      (vii) a humanized light chain framework region; and
   b) a heavy chain region comprising:
      (i) a $V_H$ CDR1 comprising the amino acid sequence of SEQ ID NO:4;
      (ii) a $V_H$ CDR2 comprising the amino acid sequence of SEQ ID NO:5;
      (iii) a $V_H$ CDR3 comprising the amino acid sequence of SEQ ID NO:6; and
      (iv) a humanized heavy chain framework region.

44. The method of claim 1, wherein the antibody comprises:
   a) a light chain region comprising:
      (i) a $V_L$ CDR1 comprising the amino acid sequence of SEQ ID NO:7;
      (ii) a $V_L$ CDR2 comprising the amino acid sequence of SEQ ID NO:8;
      (iii) a $V_L$ CDR3 comprising the amino acid sequence of SEQ ID NO:9; and
      (vii) a humanized light chain framework region; and
   b) a heavy chain region comprising:
      (i) a $V_H$ CDR1 comprising the amino acid sequence of SEQ ID NO:10;
      (ii) a $V_H$ CDR2 comprising the amino acid sequence of SEQ ID NO:11;
      (iii) a $V_H$ CDR3 comprising the amino acid sequence of SEQ ID NO:12; and
      (iv) a humanized heavy chain framework region.

45. The pharmaceutical formulation of claim 10, wherein the antibody comprises:
   a) a light chain region comprising:
      (i) a $V_L$ CDR1 comprising the amino acid sequence of SEQ ID NO:1;
      (ii) a $V_L$ CDR2 comprising the amino acid sequence of SEQ ID NO:2;
      (iii) a $V_L$ CDR3 comprising the amino acid sequence of SEQ ID NO:3; and
      (iv) a humanized light chain framework region; and
   b) a heavy chain region comprising:
      (i) a $V_H$ CDR1 comprising the amino acid sequence of SEQ ID NO:4;
      (ii) a $V_H$ CDR2 comprising the amino acid sequence of SEQ ID NO:5;
      (iii) a $V_H$ CDR3 comprising the amino acid sequence of SEQ ID NO:6; and
      (iv) a humanized heavy chain framework region.

46. The pharmaceutical formulation of claim 10, wherein the antibody comprises:
   a) a light chain region comprising:
      (i) a $V_L$ CDR1 comprising the amino acid sequence of SEQ ID NO:7;
      (ii) a $V_L$ CDR2 comprising the amino acid sequence of SEQ ID NO:8;
      (iii) a $V_L$ CDR3 comprising the amino acid sequence of SEQ ID NO:9; and
      (iv) a humanized light chain framework region; and
   b) a heavy chain region comprising:
      (i) a $V_H$ CDR1 comprising the amino acid sequence of SEQ ID NO:10;
      (ii) a $V_H$ CDR2 comprising the amino acid sequence of SEQ ID NO:11;
      (iii) a $V_H$ CDR3 comprising the amino acid sequence of SEQ ID NO:12; and
      (iv) a humanized heavy chain framework region.

47. The antibody of claim 17, wherein the antibody comprises:
  a) a light chain region comprising:
    i) a $V_L$ CDR1 comprising the amino acid sequence of SEQ ID NO:1;
    (ii) a $V_L$ CDR2 comprising the amino acid sequence of SEQ ID NO:2;
    (iii) a $V_L$ CDR3 comprising the amino acid sequence of SEQ ID NO:3; and
    (iv) a humanized light chain framework region; and
  b) a heavy chain region comprising:
    (i) a $V_H$ CDR1 comprising the amino acid sequence of SEQ ID NO:4;
    (ii) a $V_H$ CDR2 comprising the amino acid sequence of SEQ ID NO:5;
    (iii) a $V_H$ CDR3 comprising the amino acid sequence of SEQ ID NO:6; and
    (iv) a humanized heavy chain framework region.

48. The antibody of claim 17, wherein the antibody comprises:
  a) a light chain region comprising:
    i) a $V_L$ CDR1 comprising the amino acid sequence of SEQ ID NO:7;
    (ii) a $V_L$ CDR2 comprising the amino acid sequence of SEQ ID NO:8;
    (iii) a $V_L$ CDR3 comprising the amino acid sequence of SEQ ID NO:9; and
    (iv) a humanized light chain framework region; and
  b) a heavy chain region comprising:
    (i) a $V_H$ CDR1 comprising the amino acid sequence of SEQ ID NO:10;
    (ii) a $V_H$ CDR2 comprising the amino acid sequence of SEQ ID NO:11;
    (iii) a $V_H$ CDR3 comprising the amino acid sequence of SEQ ID NO:12; and
    (iv) a humanized heavy chain framework region.

49. The in vitro method of claim 37, wherein the antibody comprises:
  a) a light chain region comprising:
    (i) a $V_L$ CDR1 comprising the amino acid sequence of SEQ ID NO:1;
    (ii) a $V_L$ CDR2 comprising the amino acid sequence of SEQ ID NO:2;
    (iii) a $V_L$ CDR3 comprising the amino acid sequence of SEQ ID NO:3; and
    (iv) a humanized light chain framework region; and
  b) a heavy chain region comprising:
    (i) a $V_H$ CDR1 comprising the amino acid sequence of SEQ ID NO:4;
    (ii) a $V_H$ CDR2 comprising the amino acid sequence of SEQ ID NO:5;
    (iii) a $V_H$ CDR3 comprising the amino acid sequence of SEQ ID NO:6; and
    (iv) a humanized heavy chain framework region.

50. The in vitro method of claim 37, wherein the antibody comprises:
  a) a light chain region comprising:
    (i) a $V_L$ CDR1 comprising the amino acid sequence of SEQ ID NO:7;
    (ii) a $V_L$ CDR2 comprising the amino acid sequence of SEQ ID NO:8;
    (iii) a $V_L$ CDR3 comprising the amino acid sequence of SEQ ID NO:9; and
    (iv) a humanized light chain framework region; and
  b) a heavy chain region comprising:
    (i) a $V_H$ CDR1 comprising the amino acid sequence of SEQ ID NO:10;
    (ii) a $V_H$ CDR2 comprising the amino acid sequence of SEQ ID NO:11;
    (iii) a $V_H$ CDR3 comprising the amino acid sequence of SEQ ID NO:12; and
    (iv) a humanized heavy chain framework region.

* * * * *

UNITED STATES PATENT AND TRADEMARK OFFICE
CERTIFICATE OF CORRECTION

PATENT NO. : 8,980,270 B2
APPLICATION NO. : 14/154954
DATED : March 17, 2015
INVENTOR(S) : Irene Griswold-Prenner et al.

Page 1 of 1

It is certified that error appears in the above-identified patent and that said Letters Patent is hereby corrected as shown below:

In the Specification:
At column 1, line number 6, delete "No." and replace it with --Nos.--.

In the Claims:
At column 110, claim number 1, line number 56, delete "(vii)" and replace it with --(iv)--.

At column 110, claim number 1, line number 62, delete "NO:11:" and replace it with --NO:11;--.

At column 112, claim number 25, line number 40, delete "17," and replace it with --claim 17,--.

At column 113, claim number 37, line number 40, delete "NO:12:" and replace it with --NO:12;--.

At column 113, claim number 43, line number 67, delete "(vii)" and replace it with --(iv)--.

At column 114, claim number 44, line number 19, please delete "(vii)" and replace it with --(iv)--.

Signed and Sealed this
Third Day of November, 2015

Michelle K. Lee
*Director of the United States Patent and Trademark Office*